(12) United States Patent
Wang et al.

(10) Patent No.: US 11,801,315 B2
(45) Date of Patent: Oct. 31, 2023

(54) RADIOLIGANDS FOR MYELIN

(71) Applicant: CASE WESTERN RESERVVE UNIVERSITY, Cleveland, OH (US)

(72) Inventors: Yanming Wang, Beachwood, OH (US); Chunying Wu, Beachwood, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 17/014,803

(22) Filed: Sep. 8, 2020

(65) Prior Publication Data

US 2021/0128756 A1 May 6, 2021

Related U.S. Application Data

(63) Continuation of application No. 16/083,747, filed as application No. PCT/US2017/021623 on Mar. 9, 2017, now Pat. No. 10,765,763.

(60) Provisional application No. 62/445,555, filed on Jan. 12, 2017, provisional application No. 62/305,769, filed on Mar. 9, 2016.

(51) Int. Cl.
| | | |
|---|---|---|
| *A61K 51/00* | (2006.01) | |
| *A61M 36/14* | (2006.01) | |
| *A61K 51/04* | (2006.01) | |
| *G01N 33/58* | (2006.01) | |

(52) U.S. Cl.
CPC .......... *A61K 51/04* (2013.01); *A61K 51/0453* (2013.01); *G01N 33/58* (2013.01); *G01N 2800/285* (2013.01); *G01N 2800/52* (2013.01)

(58) Field of Classification Search
CPC .... A61K 51/04; A61K 51/0453; G01N 33/58; G01N 2800/285; G01N 2800/52
USPC ........................................................ 424/1.89
See application file for complete search history.

(56) References Cited

U.S. PATENT DOCUMENTS

| | | |
|---|---|---|
| 2008/0108840 A1 | 5/2008 | Kung et al. |
| 2010/0172836 A1 | 7/2010 | Benedum et al. |
| 2011/0189090 A1 | 8/2011 | Wang et al. |
| 2012/0328521 A1 | 12/2012 | Olbrich et al. |
| 2014/0079635 A1 | 3/2014 | Wang |

OTHER PUBLICATIONS

Kniess et al. Med. Chem. Commun. 2015, 6, 1714-1754. (Year: 2015).*
Bejot et al. Bioorg. Med. Chem. 20 (2012) 324-329. (Year: 2012).*
Sirjon et al. "An Efficient F18 labeling method for PET study: Huisgen 1,3-dipolar cycloaddition of bioactive substances and F18-labeled compounds in Tetrahedron Letters", 2007, vol. 48, pp. 3953-3957.
Glaser, et al., "Click Labeling" with 2-[18F]Fluoroethylazide for Positron Emission Tomography; Bioconjugate Chem. 2007, 18, 989-993.
Uthaiwan Sirion, et al.; "An efficient F-18 labeling method for PET study: Huisgen 1,3-dipolar cycloaddition of bioactive substances and F-18 labeled compounds"; ScienceDirect-Tetrahedron Letters vol. 48, Issue 23, Jun. 4, 2007, pp. 3953-3957; https://doi.org/10.1016/j.tetlet.2007.04.048.

* cited by examiner

Primary Examiner — Michael G. Hartley
Assistant Examiner — Sean R Donohue
(74) Attorney, Agent, or Firm — TAROLLI, SUNDHEIM, COVELL & TUMMINO, LLP

(57) ABSTRACT

A radioligand for labeling myelin includes a fluorescent trans-stilbene derivative.

17 Claims, 17 Drawing Sheets

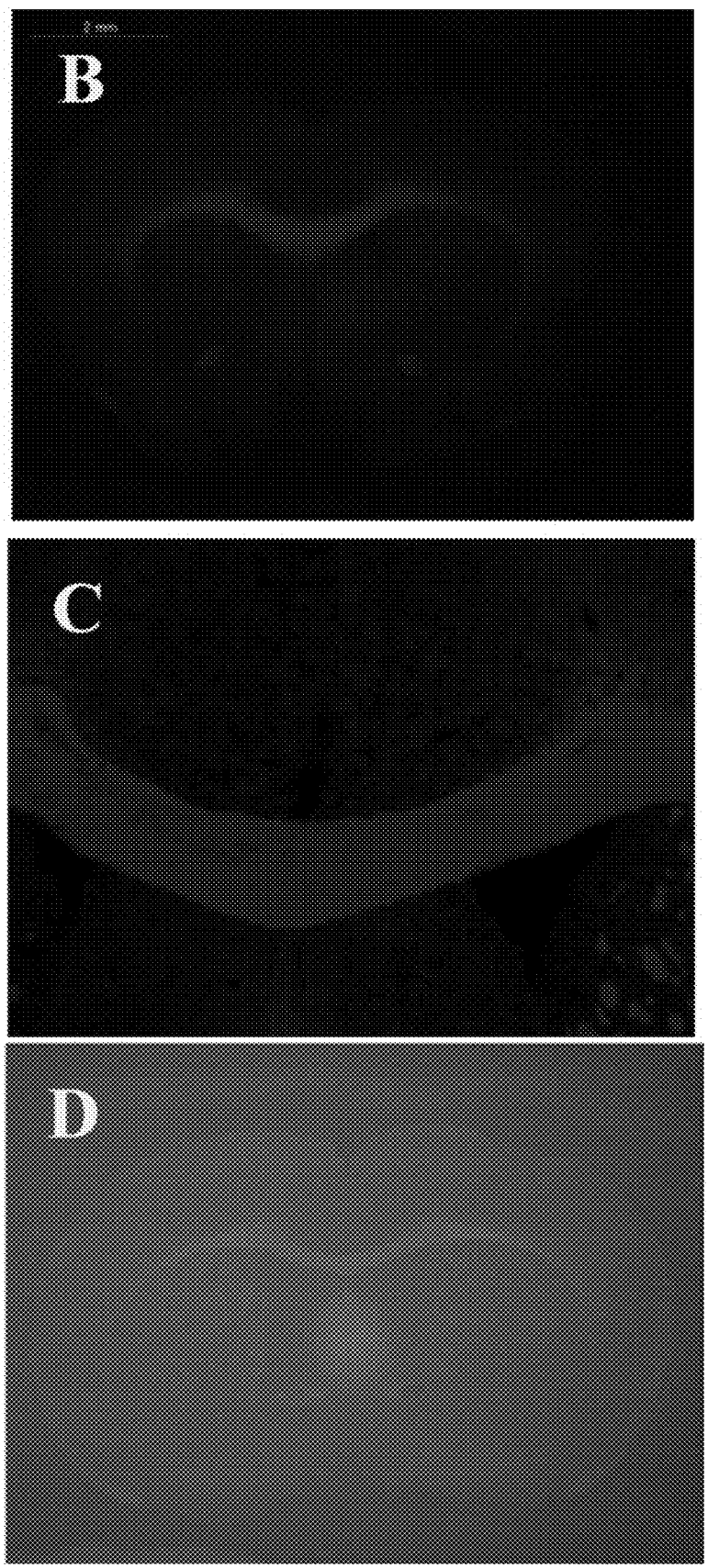
Figs. 3B-D

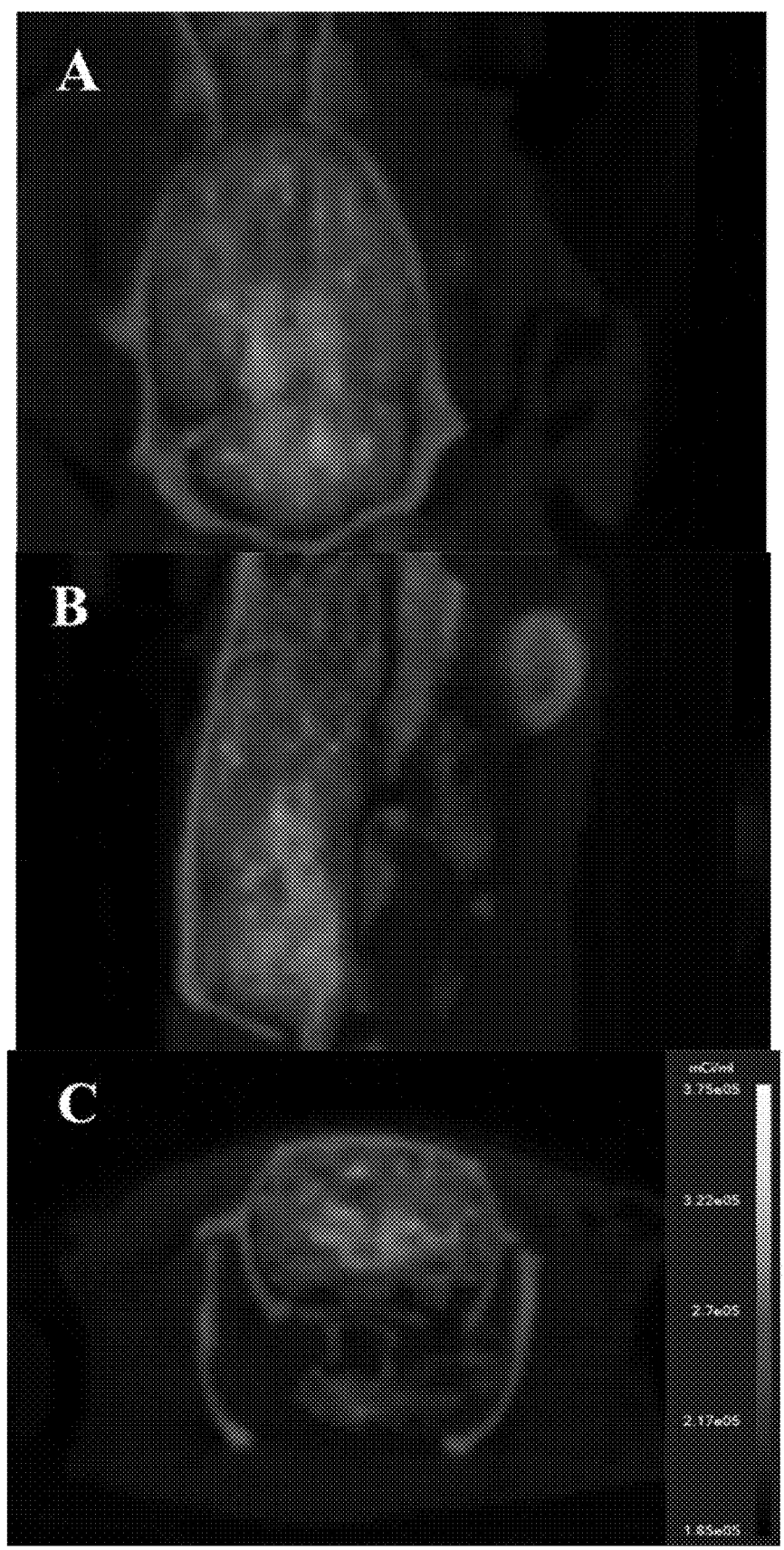
Figs. 5A-C

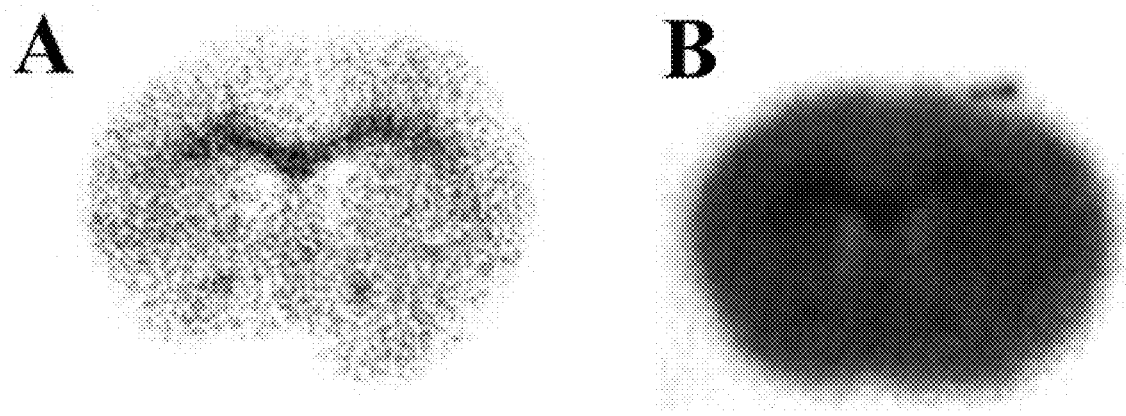
Figs. 6A-B
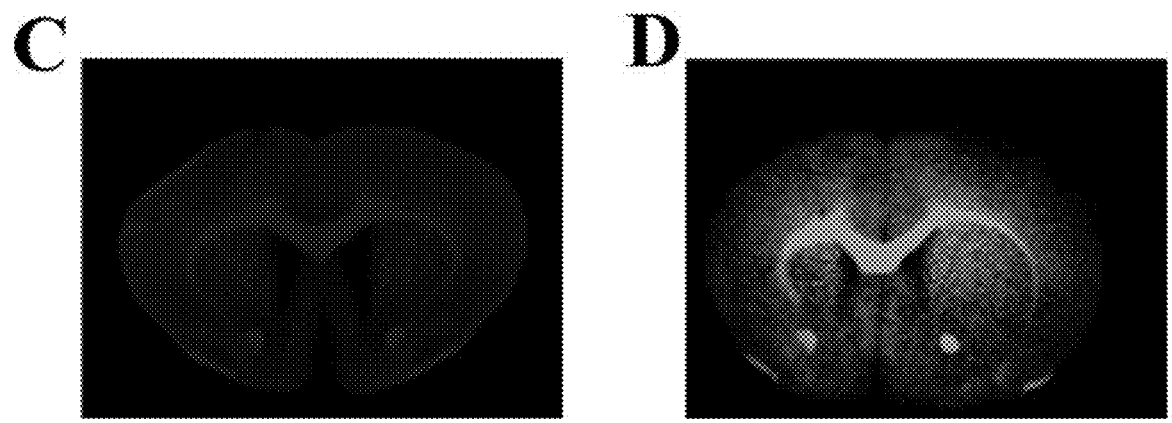
Figs. 6C-D
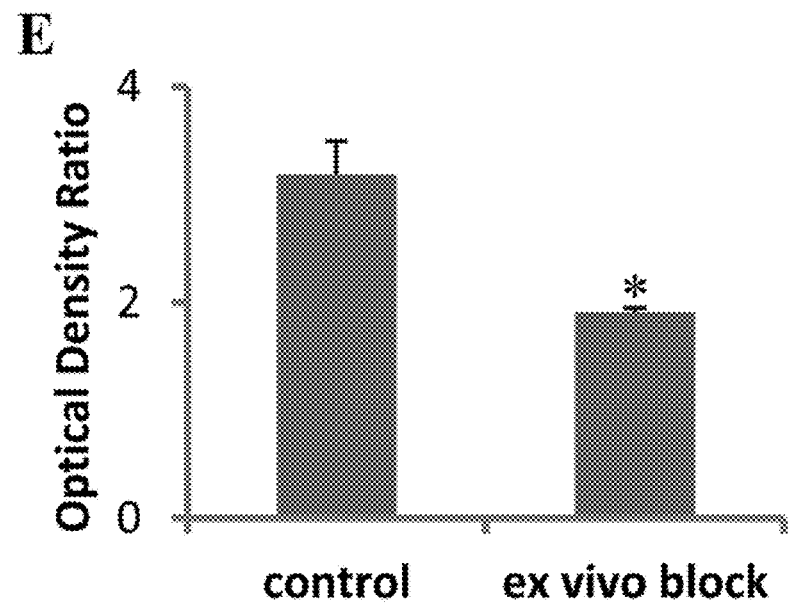
Fig. 6E

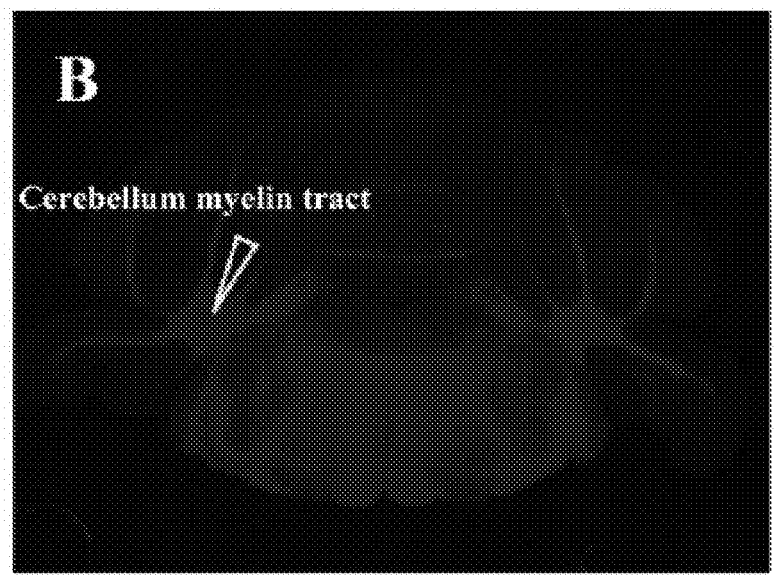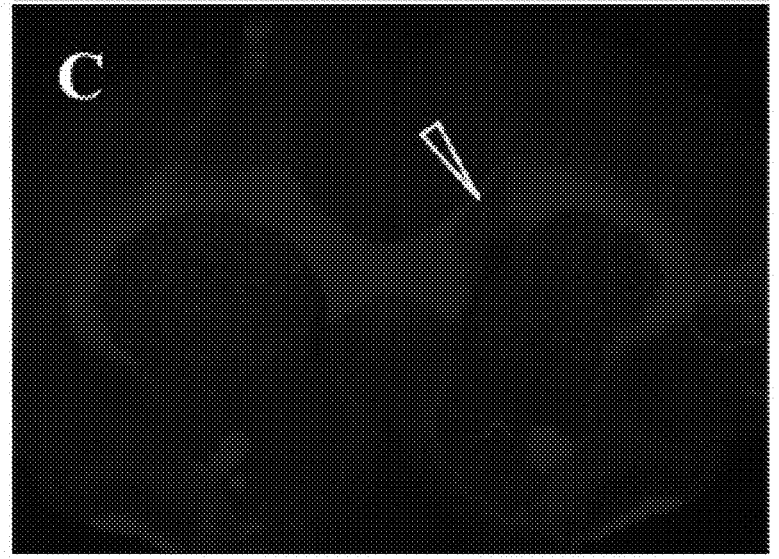
Figs. 8B-D

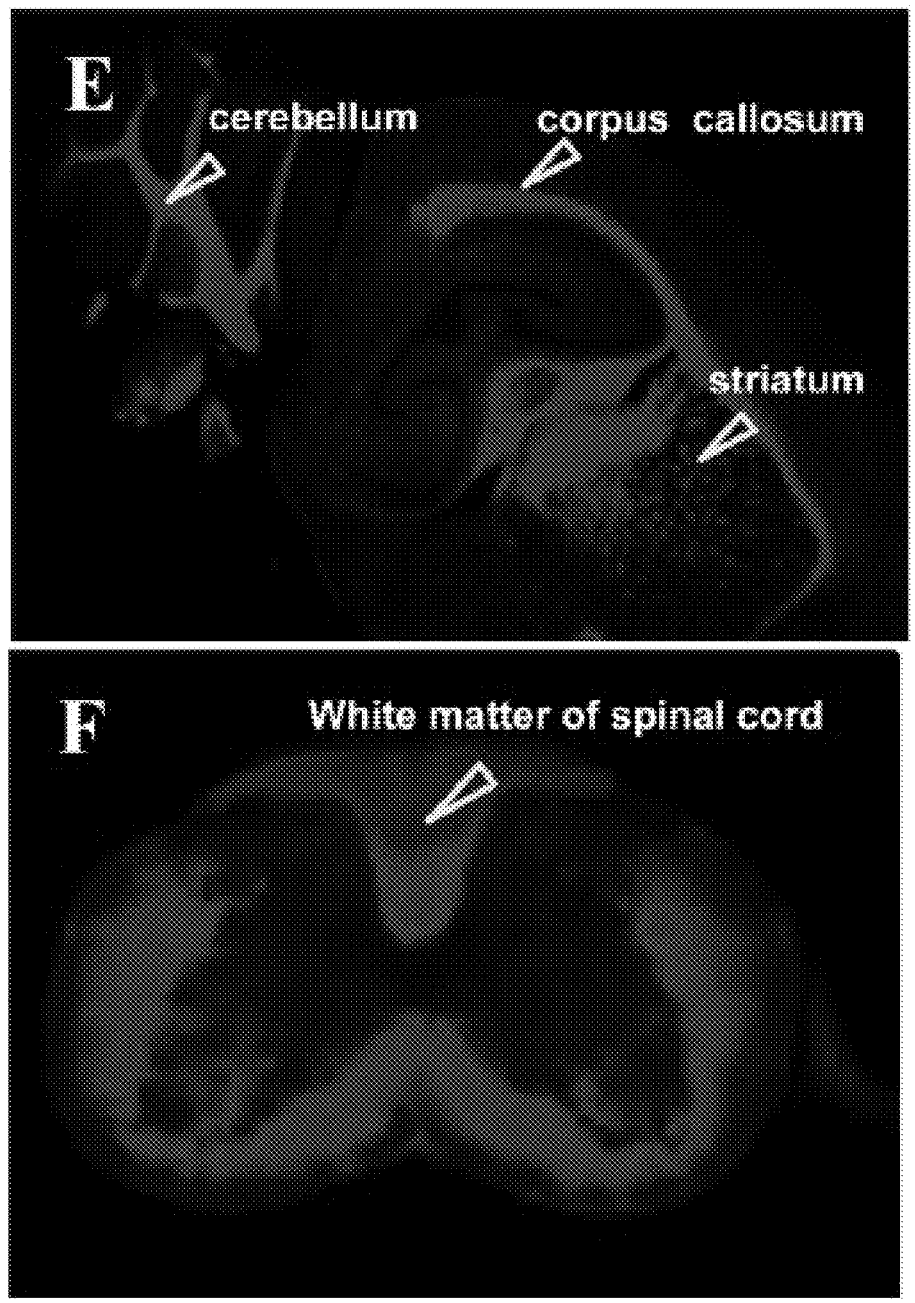
Figs. 8E-F

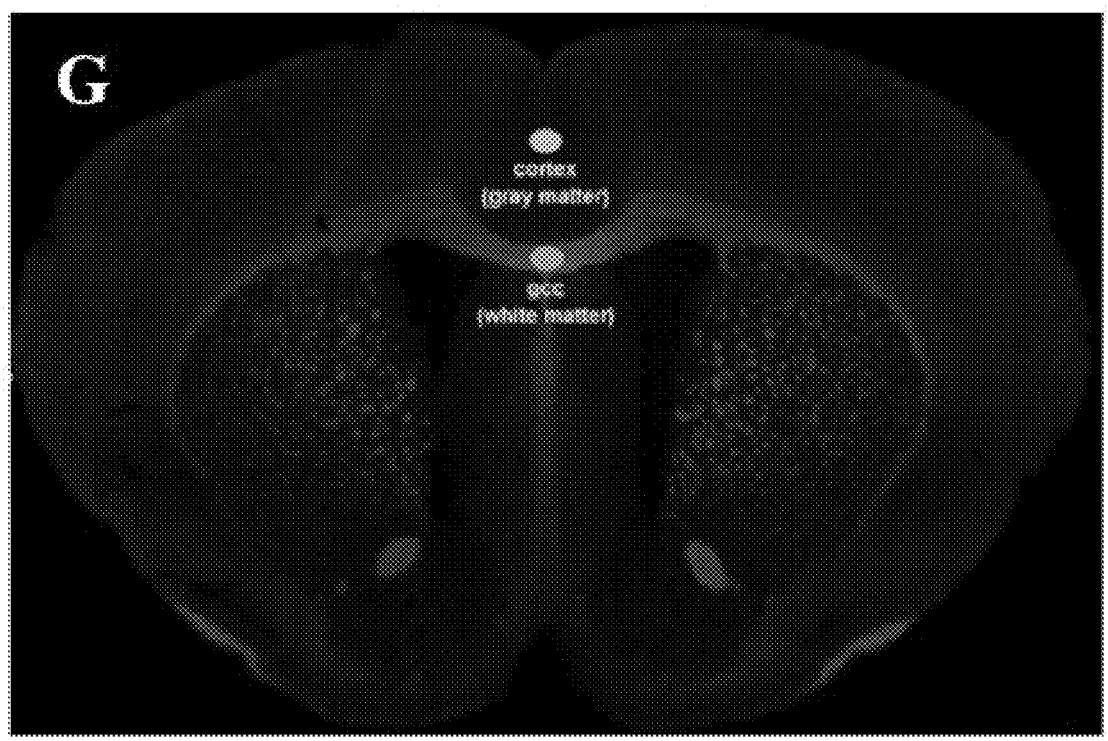
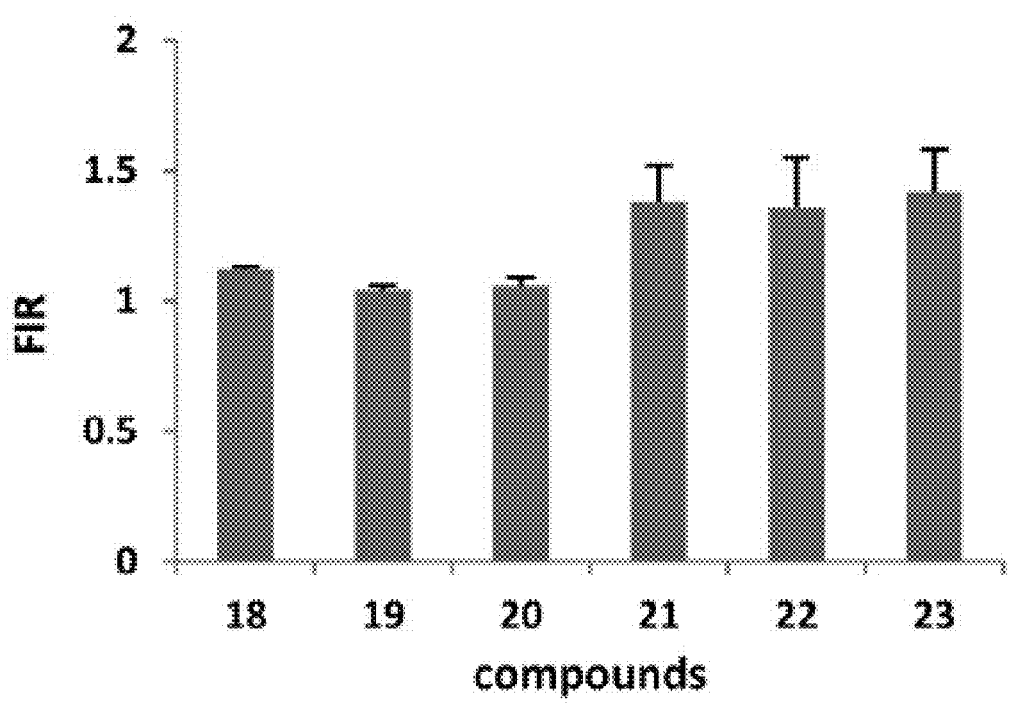
Figs. 8G-H

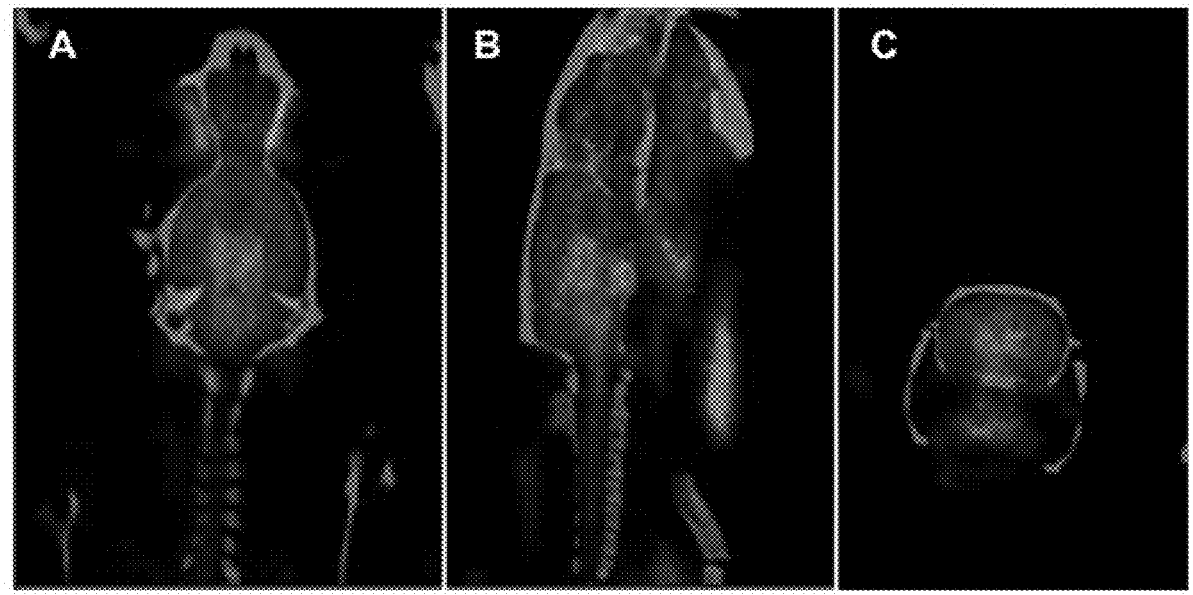
Figs. 9A-C
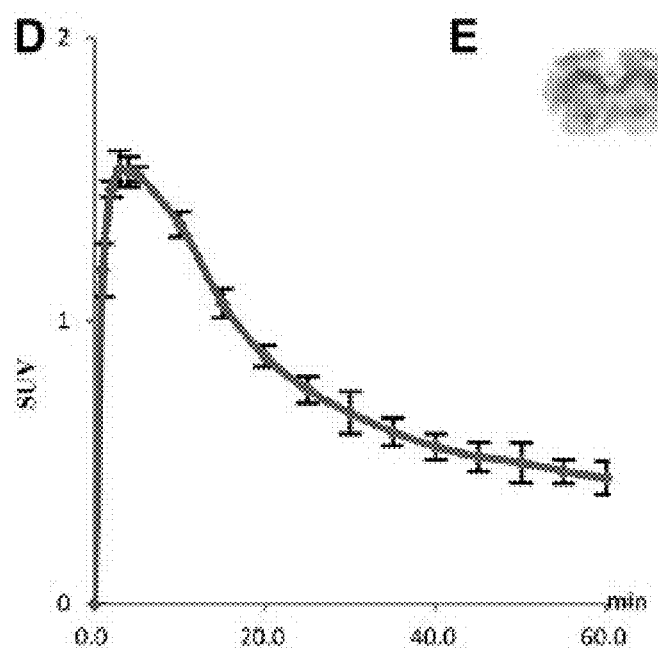
Figs. 9D-E

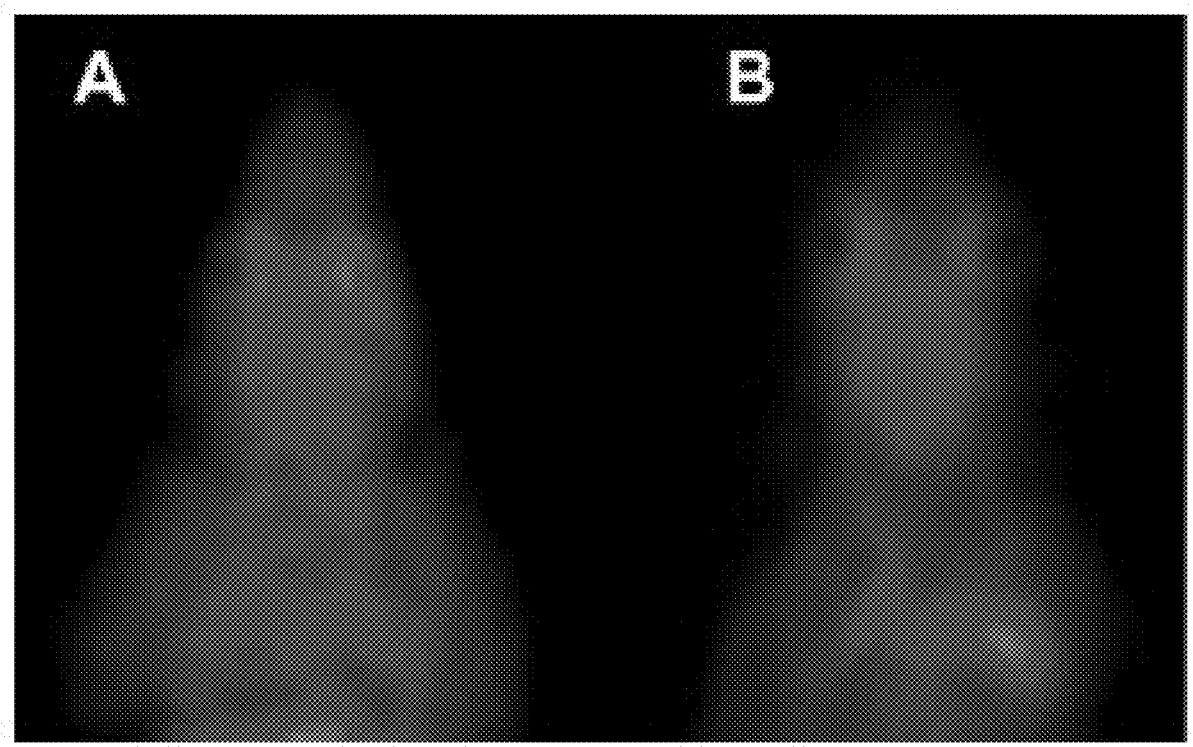
Figs. 10A-B
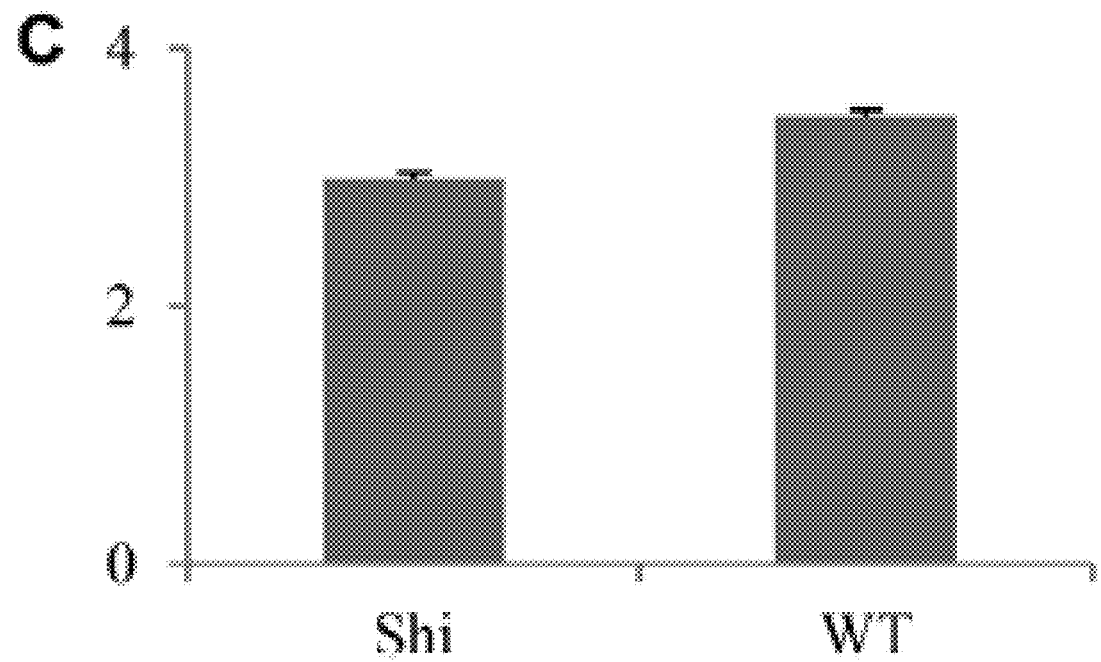
Fig. 10C

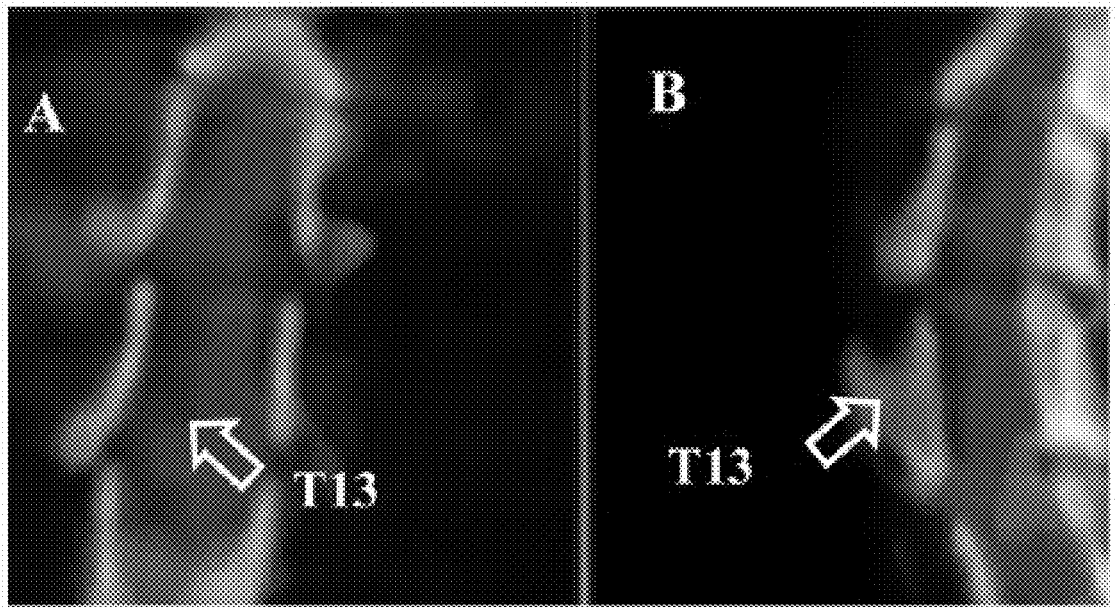
Figs. 11A-B
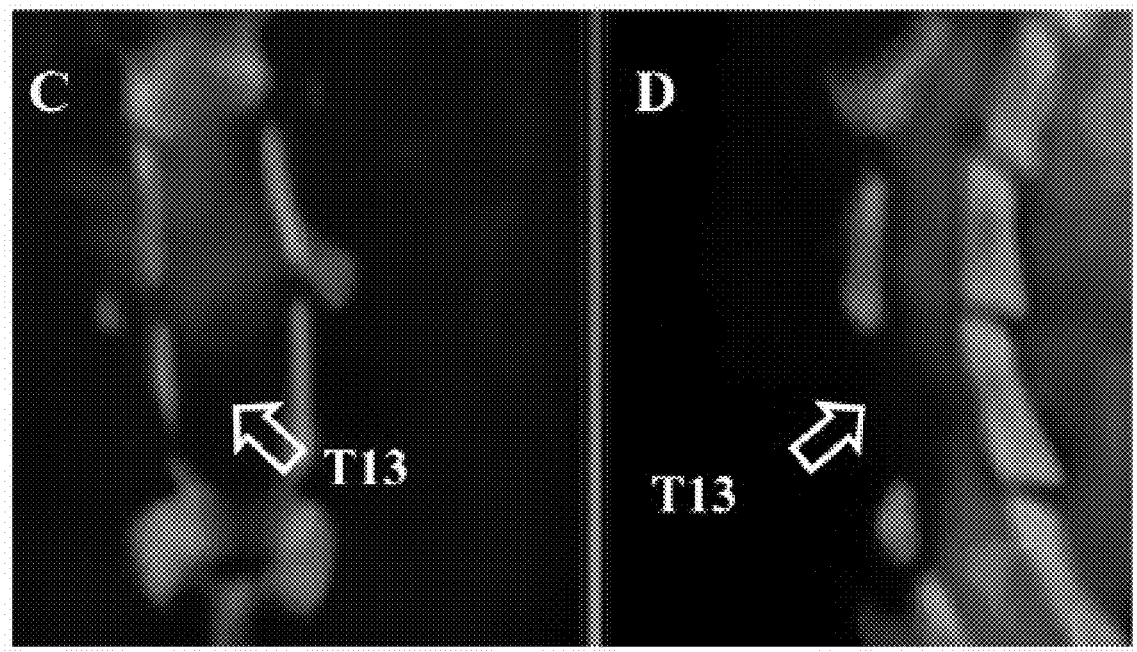
Figs. 11C-D

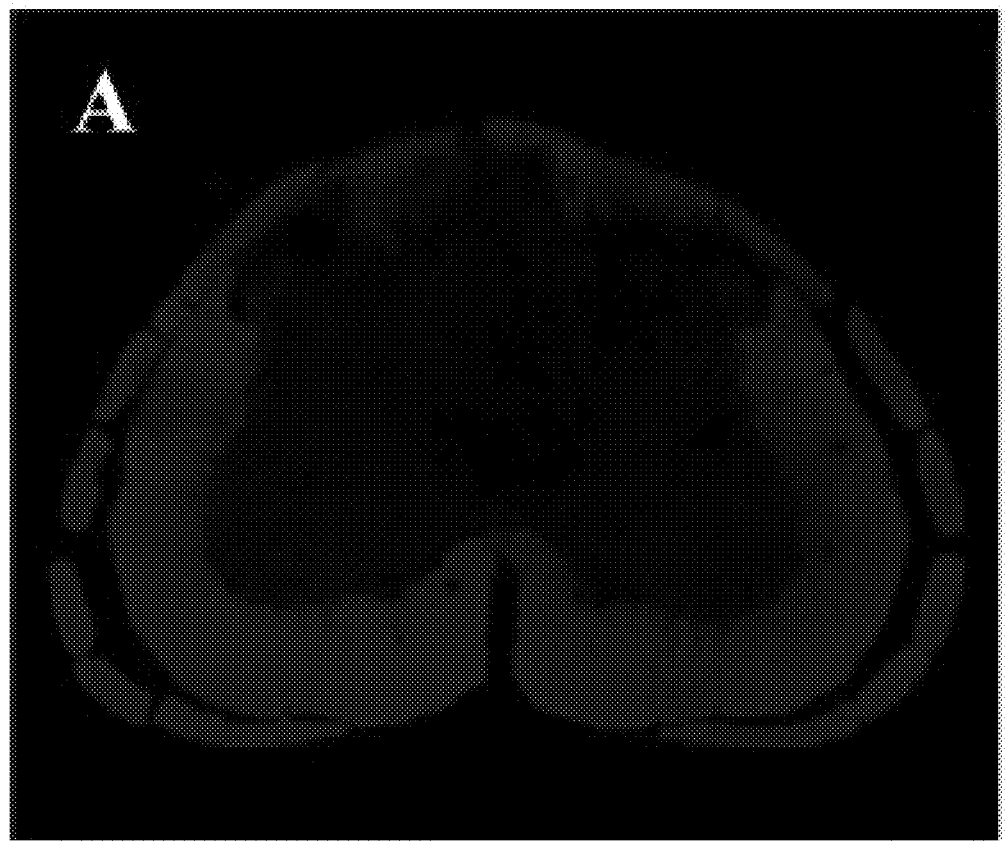
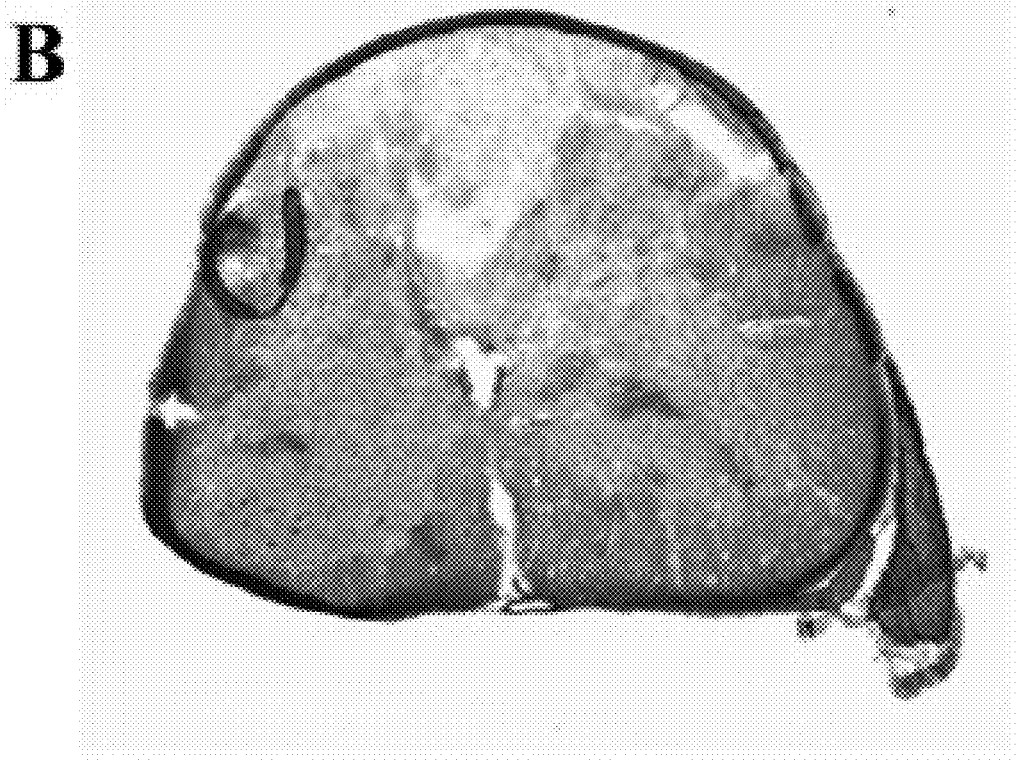
Figs. 12A-B

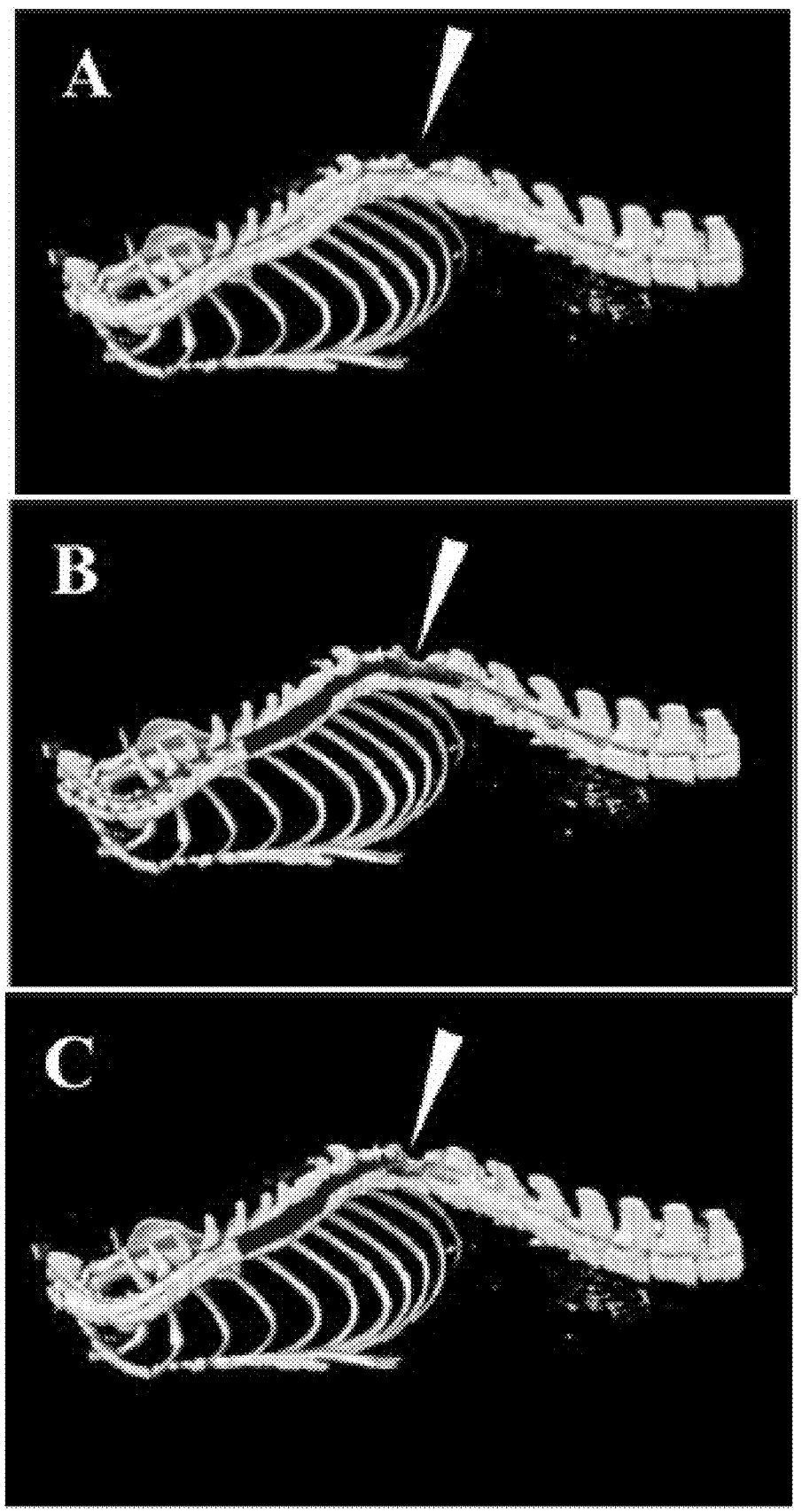
Figs. 13A-C

RADIOLIGANDS FOR MYELIN

RELATED APPLICATION

This application claims priority from U.S. Provisional Application Nos. 62/305,769, filed Mar. 9, 2016 and 62/445,555 filed Jan. 12, 2017, the subject matter of which are incorporated herein by reference in their entirety.

GOVERNMENT FUNDING

This invention was made with government support under Grant No. NS061837 awarded by the National Institute of Health (NIH). The United States government has certain rights to the invention.

TECHNICAL FIELD

Embodiments described herein relate to radioligands and to methods of their use, and particularly relates to radioligands that readily enter the brain and selectively localize in the myelinated regions.

BACKGROUND

Myelin is a specialized membrane that ensheathes neuronal axons, promoting efficient nerve impulse transmission (Morell and Quarles (1999) Basic Neurochemistry: molecular, cellular, and medical aspects. In Siegel GJ, ed. Myelin Formation, Structure, and Biochemistry. Lippincott-Raven Publishers, 79-83). Due to its important biological functions in the normal central nervous system (CNS) and its vulnerability in disease, several techniques have been developed to visualize and characterize myelin histopathology. These can be broadly divided into those based upon antibody immunohistochemistry (IHC) (Horton and Hocking (1997) Cereb. Cortex 7:166-177) and more traditional histochemical procedures. The classic histochemical stains include luxol fast blue MBN (Kluver and Barrera (1953) J Neurosci Methods 153: 135-146; Presnell and Schreibman (1997) Humanson's Animal Tissue Techniques, $5^{th}$ ed.; Kiernan (1999) Histological and Histochemical Methods: Theory and practice, $3^{rd}$ ed.; Bancroft and Gamble (2002), Theory and Practice of Histological Techniques, 5 ed. and Sudan Black B (Lison and Dagnelie (1935) Bull. d'Histologie Appliquee 12: 85-91). Traditional chromogenic methods also include the Palweigert method ((Weigert (1884) Fortschr Deutsch Med 2: 190-192, (1885) Fortschr Deutsch Med 3:236-239; Clark and Ward (1934) Stain Technol 54:13-16), the Weil stain (Weil (1928) Arch Neurol Psychiatry 20:392-393; Berube et al. (1965) Stain Technol 40:53-62)), the Loyez method (Cook (1974) Manual of Histological Demonstration Methods, $5^{th}$ ed.), and a method based on horse serum followed by subsequent reaction with diaminobenzidine (McNally and Peters (1998) J Histochem Cytochem 46:541-545). In addition, modified silver stains including the Gallyas method (Pistorio et al. (2005) J Neurosci Methods 153: 135-146) and Schmued's gold chloride technique (Schmued and Slikker (1999) Brain Res 837:289-297) have also been used as simple, high-resolution histochemical markers of myelin. More recently, fluoromyelin (Kanaan et al. (2005) Am J Physiol Regul Integr Comp Physiol 290:R1105-1114) and NIM (Xiang et al. (2005) J Histochem Cytochem 53:1511-1516) were introduced as novel myelin dyes, which enable quick and selective labeling of myelin in brain tissue sections. Although these myelin-staining techniques are widely used in vitro, none can be applied in vivo due to impermeability of the blood-brain barrier (BBB). The lack of in vivo radioligands has limited the progress of myelin imaging and hindered efficacy evaluation of novel myelin repair therapies during their development.

SUMMARY

Embodiments described herein relate to radioligands for use in the detection and quantification of myelin in a subject. The radioligands include a fluorescent trans-stilbene derivative having the following formula:

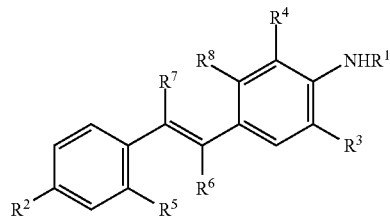

wherein $R^1$ is a H, a lower alkyl group, or a radiolabeled triazole group;

$R^2$ is H, or NHR', where R' is H, a lower alkyl group, or a radiolabeled triazole group;

$R^3$ and $R^4$ are same or different and are each independently H, NHR", where R" is H or a lower alkyl group, or a radiolabeled lower alkyl group, alkylene group, alkenyl group, alkynyl group, or alkoxy group;

$R^5$ and $R^6$ are H or are linked to form a cyclic ring, wherein the cyclic ring is aromatic, alicyclic, heteroaromatic, or heteroalicyclic;

$R^7$ and $R^8$ are H or are linked to form a cyclic ring, wherein the cyclic ring is aromatic, alicyclic, heteroaromatic, or heteroalicyclic;

wherein at least one of $R^1$, $R^2$, $R^3$, or $R^4$ includes a radiolabel selected from the group consisting of $^{18}$F, $^{123}$I, $^{125}$I, and $^{99m}$Tc; or a pharmaceutically acceptable salt thereof. For example, the at least one radiolabel can be $^{18}$F.

Other embodiments described herein relate to a method of detecting myelin in a subject's tissue. The myelin can be associated with nerves of the central system and/or the peripheral system. The tissue can include brain tissue, spinal tissue, and other tissue associated with the peripheral nervous system. In some aspects, the tissue can be myelinated tissue at a surgical site.

The method includes administering to the subject a radioligand that includes a fluorescent trans-stilbene derivative having the following formula:

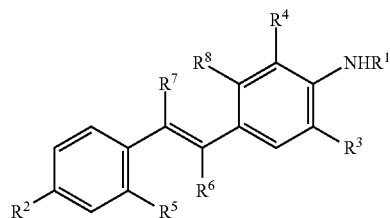

wherein $R^1$ is a H, a lower alkyl group, or a radiolabeled triazole group;

$R^2$ is H, or NHR', where R' is H, a lower alkyl group, or a radiolabeled triazole group;

R³ and R⁴ are same or different and are each independently H, NHR", where R" is H or a lower alkyl group, or a radiolabeled lower alkyl group, alkylene group, alkenyl group, alkynyl group, or alkoxy group;

R⁵ and R⁶ are H or are linked to form a cyclic ring, wherein the cyclic ring is aromatic, alicyclic, heteroaromatic, or heteroalicyclic;

R⁷ and R⁸ are H or are linked to form a cyclic ring, wherein the cyclic ring is aromatic, alicyclic, heteroaromatic, or heteroalicyclic;

wherein at least one of $R^1$, $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof.

Following, administration of the radioligand, the radioligand can be detected to determine the location, distribution, and/or amount of the radioligand that is bound to and/or labels the myelin.

Other embodiments described herein relate to a method of detecting a myelination related disorder in a subject. The method includes administering to the subject a radioligand that includes a fluorescent trans-stilbene derivative having the following formula:

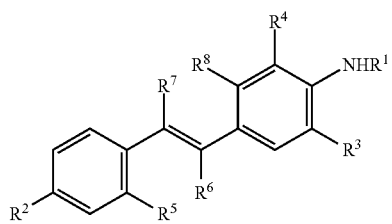

wherein $R^1$ is a H, a lower alkyl group, or a radiolabeled triazole group;

$R^2$ is H, or NHR', where R' is H, a lower alkyl group, or a radiolabeled triazole group;

R³ and R⁴ are same or different and are each independently H, NHR", where R" is H or a lower alkyl group, or a radiolabeled lower alkyl group, alkylene group, alkenyl group, alkynyl group, or alkoxy group;

R⁵ and R⁶ are H or are linked to form a cyclic ring, wherein the cyclic ring is aromatic, alicyclic, heteroaromatic, or heteroalicyclic;

R⁷ and R⁸ are H or are linked to form a cyclic ring, wherein the cyclic ring is aromatic, alicyclic, heteroaromatic, or heteroalicyclic;

wherein at least one of $R^1$, $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof.

The distribution and/or amount of the radioligand bound to and/or labeling myelin in the subject's neural tissue is then detected, measured, and/or quantified and compared to a control. A decreased distribution and/or amount of the radioligand compared to the control can be indicative of a decrease in myelination of the neural tissue.

In some aspects, the myelination related disorder includes a neurodegenerative autoimmune disease. In certain aspects, the neurodegenerative disease can be multiple sclerosis.

Still other embodiments relate to a method of monitoring the efficacy of a remyelination therapy in a subject. The method includes administering to a subject undergoing remyelination therapy a radioligand that includes a fluorescent trans-stilbene derivative having the following formula:

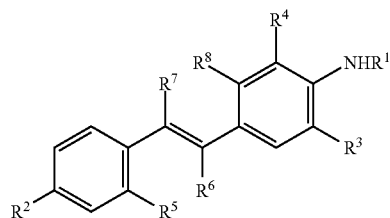

wherein $R^1$ is a H, a lower alkyl group, or a radiolabeled triazole group;

$R^2$ is H, or NHR', where R' is H, a lower alkyl group, or a radiolabeled triazole group;

R³ and R⁴ are same or different and are each independently H, NHR", where R" is H or a lower alkyl group, or a radiolabeled lower alkyl group, alkylene group, alkenyl group, alkynyl group, or alkoxy group;

R⁵ and R⁶ are H or are linked to form a cyclic ring, wherein the cyclic ring is aromatic, alicyclic, heteroaromatic, or heteroalicyclic;

R⁷ and R⁸ are H or are linked to form a cyclic ring, wherein the cyclic ring is aromatic, alicyclic, heteroaromatic, or heteroalicyclic;

wherein at least one of $R^1$, $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof.

The distribution and/or amount of the radioligand bound to and/or labeling myelin in the subject's neural tissue is detected, measured, and/or quantified and compared to a control. An increased distribution and/or amount of the radioligand compared to the control can be indicative of efficacy of the remyelination therapy.

BRIEF DESCRIPTION OF THE DRAWINGS

The foregoing and other features and advantages of the present invention will become apparent to those skilled in the art to which the present invention relates upon reading the following description with reference to the accompanying drawings.

FIGS. 5(A-C) illustrate images showing representative (A) coronal, (B) sagittal, and (C) axial microPET/CT fusion images of the rat brain following i.v. administration of [$^{18}F$]32, showing high uptakes of [18F]32 in the white matter region of the brain.

FIGS. 6(A-E) illustrate film autoradiography. (A) Ex vivo autoradiography showing [$^{18}F$]32 binds to myelinated corpus callosum (CC) in mouse brain (coronal) and was consistent with histological staining of myelinated regions (C). (B) After pretreatment with nonlabeled CIC, ex vivo autoradiographic visualization of CC was significantly decreased. Distinct staining of CIC was observed when the same section was viewed under fluorescent microscope (D). (E) Statistical analysis of optical density ratio of gcc to cortex on the film showed there is significant difference between control and ex vivo or in vitro block studies. *: p<0.05.

FIGS. 9(A-E) illustrate images and plots showing representative (A) coronal, (B) sagittal, and (C) axial microPET/CT fusion images of the rat brain following iv administration of [$^{18}$F]21, showing high uptake in the white matter region of the brain. (D) Quantitative analysis of average radioactivity concentration of target compound [$^{18}$F]21 in the whole brain of rats (n=3) in terms of SUV as a function of time. (E) In situ autoradiography showing [18F]21 binds to myelinated corpus callosum in mouse brain (coronal).

FIGS. 10(A-C) illustrates representative coronal microPET images of the shiverer mouse brain (A) and WT mouse brain (B) following iv administration of [$^{18}$F]21, showing higher brain uptake in the control than that in the shiverer mouse. (C) Quantitative analysis of total uptake of [$^{18}$F]21 in terms of SUV at 40-60 min post-injection in shiverer mice [Shi] and control mouse [WT], showing significant higher uptake in WT mouse brain (p=0.00028, two-tailed t test).

FIGS. 12(A-B) illustrate in situ histological staining of the SCI (T13) tissue section with reference compound 21 after microPET/CT imaging showing a demyelinated lesion at dorsal portion (A), which is consistent with LFB and cresyl violet staining using adjacent sections (B).

DETAILED DESCRIPTION

Figure 1:
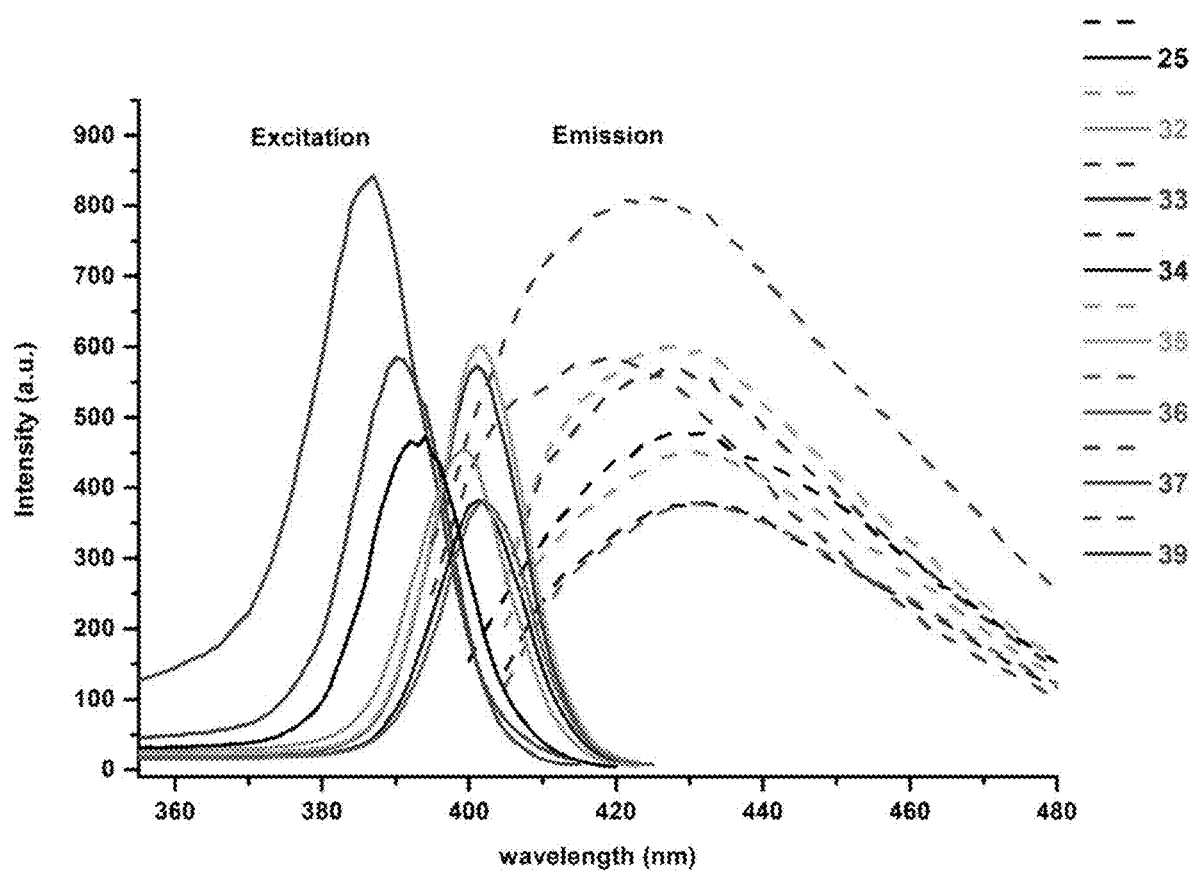
FIG. 1 illustrates a plot showing excitation (Em 420±10 nm; solid) and emission (Ex 390±10 nm; dashed) spectra of the compounds 25, 32-37 and 39.

The definitions provided herein are to facilitate understanding of certain terms used frequently herein and are not meant to limit the scope of the application.

The term "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

The term "pharmaceutically acceptable salts" or complexes refers to salts or complexes that retain the desired biological activity of the parent compound and exhibit minimal, if any, undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

A radioligand exhibits "specific binding" or "selective binding" to myelin if it associates more frequently with, more rapidly with, for a longer duration with, or with greater affinity to, myelin than with tissues not containing myelin. "Non-specific binding" refers to binding of the radioligand to non-myelin containing tissue. For relative binding values, such as specific binding or nonspecific binding, each sample should be measured under similar physical conditions (i.e., temperature, pH, and solvent). Generally, specific binding is characterized by a relatively high affinity of a radioligand to a receptor and a relatively low to moderate capacity. Typically, binding is considered specific when the affinity constant Ka is at least $10^6$ M$^{-1}$. A higher affinity constant indicates greater affinity, and thus typically greater specificity. "Non-specific" binding usually has a low affinity with a moderate to high capacity. Non-specific binding usually occurs when the affinity constant is below $10^6$ M$^{-1}$.

The phrase "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

The phrase "remyelination" refers to the spontaneous, therapeutic, or experimentally induced repair, regeneration, or otherwise enhanced constitution or functionality of the insulating material ensheathing neuronal axons.

The phrase "molecular imaging" refers to a non-invasive technique for in vivo imaging of biological targets at molecular level. Molecular imaging can involve the targeting of a biomarker with a radioligand.

The phrase "radioligand" refers to a compound that specifically binds to a biomarker (e.g., myelin), allowing for the imaging and studying of the marker. As used herein, the phrase "biomarker" refers to a biological substance that is specific to a certain biological process or mechanism.

The term "subject" refers to an animal, such as a mammal including a small mammal (e.g., mouse, rat, rabbit, or cat) or a larger mammal (e.g., dog, pig, or human). In particular aspects, the subject is a large mammal, such as a human.

The terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal, one or more individuals diagnosed with a myelination related disease.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "cyclic" refers to alicyclic or aromatic substituents that may or may not be substituted and/or heteroatom containing, and that may be monocyclic, bicyclic, or polycyclic.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

This application relates to radioligands that upon administration to a subject or tissue of the subject can specifically or selectively bind to, localize with, and/or label myelinated regions of the nervous system, including the central nervous system and peripheral nervous system, and upon specifically or selectively binding to, localizing with, and/or labeling can be imaged, using, for example, fluorescence and/or positron emission tomography (PET) imaging, to detect, measure, and/or quantify the amount, level, and/or distribution of myelin in the tissue being imaged. The radioligands can bind to myelin membrane and do not bind to a component of degenerating myelin fragments. The radioligands can also be readily visualized using conventional visualization techniques to indicate myelinated regions of the brain, central nervous system, and peripheral nervous system. The radioligands described herein can be used in a method of detecting or quantifying a level of myelination in vivo in a subject, a method of detecting a myelination related disorder in a subject, a method of monitoring the remyelination effects of an agent in a subject, a method of screening the myelination effects of an agent in a subject, surgical methods where the presence or location of nerves is desired, and multi-modal imaging applications of myelin.

The radioligand can be detected in vivo using positron emission tomography (PET) as well as by fluorescent imaging. PET is a functional imaging technique that can detect chemical and metabolic change at the molecular level. Another example of an in vivo imaging modality that can be used to detect a radioligand is MicroPET. MicroPET is a high resolution positron emission tomography scanner designed for imaging small laboratory animals. In some aspects of the invention, the in vivo imaging modality is single-photon emission computerized tomography (SPECT).

In an embodiment of the application, the radioligands can exhibit excitation wavelengths in a range of about 370 nm to about 400 nm and emission wavelengths in a range of about 410 nm to about 440 nm. Thus, the radioligands can be used in a method for irradiating and imaging myelin with light of the wavelength range from about 370 nm to about 440 nm. For example, a radioligand described herein can have excitation peaked at about 390 nm and emission peaked at about 420 nm.

In some aspects, the radioligands can meet the requirements that generally apply to diagnostic pharmaceuticals. As these substances may be applied at higher doses and for a longer diagnostic period, they can have a low-toxicity. In addition, the radioligands described herein can be of low molecular weight, lipophilic, and readily penetrate the blood-brain barrier in sufficient amounts to be detectable by positron emission tomography imaging and bind to myelin fibers with high affinity and specificity without being rapidly degraded. In some embodiments, the radioligands can have a lipophilicity of about 2.5 to about 5.4 or about 2.7 to about 4.0 to enhance crossing of the blood brain barrier upon systemic administration of the radioligand to the subject. The radioligands are also sufficiently stable in chemical and photophysical respect, at least for as long as the diagnostic period lasts.

The radioligand can include a fluorescent trans-stilbene derivative or a pharmacophore thereof (e.g., coumarin pharmacophore) that is less than about 700 daltons and has a relatively high binding affinity (Kd) (e.g., at least about 1.0 nM) to isolated myelin fractions but a relatively low binding affinity (Kd) to isolated non-myelin fractions. The terms "fluorescent trans-stilbene" or "fluorescent trans-stilbene derivative" or "fluorescent trans-stilbene compound" are meant encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

In some embodiments, the radioligand can include a fluorescent trans-stilbene derivative having the following formula:

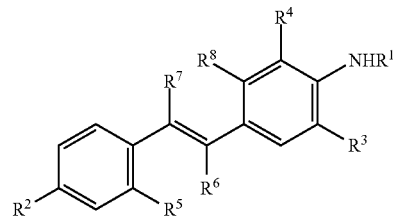

wherein $R^1$ is a H, a lower alkyl group, or a radiolabeled triazole group;

$R^2$ is H, or NHR', where R' is H, a lower alkyl group, or a radiolabeled triazole group;

$R^3$ and $R^4$ are same or different and are each independently H, NHR", where R" is H or a lower alkyl group, or a radiolabeled lower alkyl group, alkylene group, alkenyl group, alkynyl group, or alkoxy group;

$R^5$ and $R^6$ are H or are linked to form a cyclic ring, wherein the cyclic ring is aromatic, alicyclic, heteroaromatic, or heteroalicyclic;

$R^7$ and $R^8$ are H or are linked to form a cyclic ring, wherein the cyclic ring is aromatic, alicyclic, heteroaromatic, or heteroalicyclic;

wherein at least one of $R^1$, $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof. For example, the at least one radiolabel can be $^{18}F$.

In other embodiments, the radioligand can include a fluorescent stilbene derivative having the following formula:

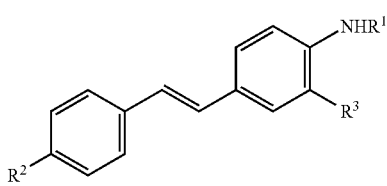

wherein $R^1$ is a H, a lower alkyl group, or a radiolabeled triazole group;

$R^2$ is H, or NHR', where R' is H, a lower alkyl group, or a radiolabeled triazole group;

$R^3$ is H, or a radiolabeled lower alkyl group, alkylene group, alkenyl group, alkynyl group, or alkoxy group;

wherein at least one of $R^1$, $R^2$, or $R^3$ includes a radiolabel selected from the group consisting of $^{18}F$, $^{123}I$, $^{125}I$, and $^{99m}Tc$; or a pharmaceutically acceptable salt thereof. For example, the at least one radiolabel can be $^{18}F$.

In other embodiments, the radioligand can include a fluorescent stilbene derivative having the following formula:

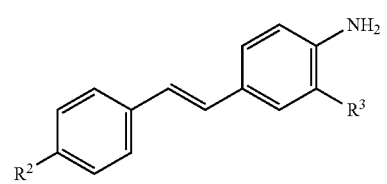

wherein $R^2$ is H, or NHR', where R' is H, a lower alkyl group, or a radiolabeled triazole group;

$R^3$ is H, or a radiolabeled lower alkyl group, alkylene group, alkenyl group, alkynyl group, or alkoxy group;

wherein at least one of $R^2$ or $R^3$ includes a radiolabel selected from the group consisting of $^{18}F$, $^{123}I$, $^{125}I$, and $^{99m}Tc$; or a pharmaceutically acceptable salt thereof. For example, the at least one radiolabel can be 18F.

In other embodiments, the radioligand can include a fluorescent stilbene derivative having the following formula:

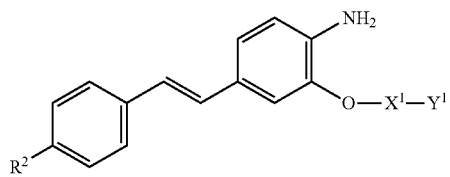

wherein $R^2$ is H, or NHR', where R' is H, a lower alkyl group, or a radiolabeled triazole group;

$X^1$ is a lower alkyl group, alkylene group, alkenyl group, alkynyl group, or alkoxy group;

$Y^1$ is a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments, the radioligand can include a fluorescent stilbene derivative having the following formula:

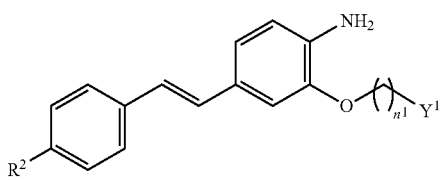

$R^2$ is H, or NHR', where R' is H, a lower alkyl group, or a radiolabeled triazole group;

$n^1$ is 1 to 6;

$Y^1$ is a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments, the radioligand can include a fluorescent stilbene derivative having the following formula:

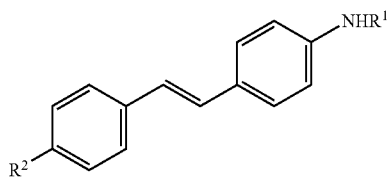

wherein $R^1$ is a H, a lower alkyl group, or a radiolabeled triazole group;

$R^2$ is H, or NHR', where R' is H, a lower alkyl group, or a radiolabeled triazole group;

wherein at least one of $R^1$ or $R^2$ includes a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments, the radioligand can include a fluorescent stilbene derivative having the following formula:

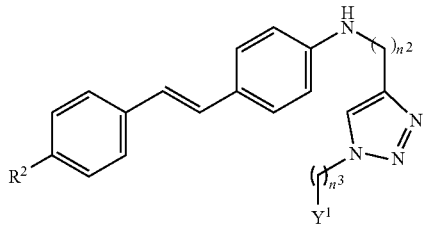

wherein $R^2$ is H, or NHR', where R' is H or a lower alkyl group;

$n^2$ is 1 to 6;

$n^3$ is 1 to 6;

$Y^1$ is a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments, the radioligand can include a fluorescent coumarin derivative that is a pharmacophore of trans-stilbene. The fluorescent coumarin derivative can have the following formula:

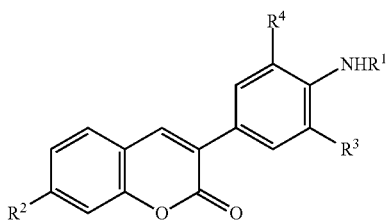

wherein $R^1$ is a H, a lower alkyl group, or a radiolabeled triazole group;
$R^2$ is H, or NHR', where R' is H, a lower alkyl group, or a radiolabeled triazole group;
$R^3$ and $R^4$ are same or different and are each independently H, NHR", where R" is H or a lower alkyl group, or a radiolabeled lower alkyl group, alkylene group, alkenyl group, alkynyl group, or alkoxy group;
wherein at least one of $R^1$, $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments the radioligand is fluorescent coumarin derivative having the following formula:

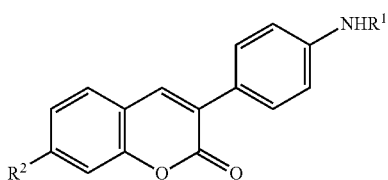

wherein $R^1$ is a H, a lower alkyl group, or a radiolabeled triazole group;
$R^2$ is H, or NHR', where R' is H, a lower alkyl group, or a radiolabeled triazole group;
wherein at least one of R or $R^2$ includes a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In other embodiments the radioligand can include a fluorescent coumarin derivative having the following formula:

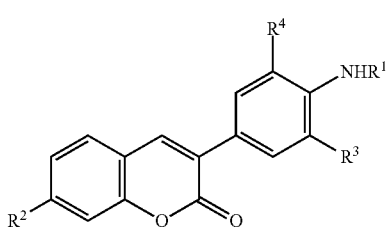

wherein $R^2$ is H, or NHR', where R' is H, a lower alkyl group, or a radiolabeled triazole group;
$R^3$ and $R^4$ are same or different and are each independently H, NHR", where R" is H or a lower alkyl group, or a radiolabeled lower alkyl group, alkylene group, alkenyl group, alkynyl group, or alkoxy group;
wherein at least one of $R^2$, $R^3$, or $R^4$ includes a radiolabel selected from the group consisting of $^{18}F$, $^{123}I$, $^{125}I$, and $^{99m}Tc$; or a pharmaceutically acceptable salt thereof. For example, the radiolabel can be $^{18}F$.

In further embodiments, the radioligand can be selected from the following structures:

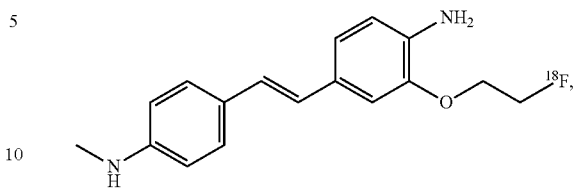

or pharmaceutically acceptable salts thereof.

The foregoing formulae represent the general structures of radiolabeled fluorescent trans-stilbene compounds found to be effective radioligands for labeling myelin in vivo as well as in vitro as described in the examples below. They are characterized by their ability to be administered to a mammal or subject parenterally and selectively localize to myelinated regions in the brain, central nervous system, and peripheral nervous system via direct binding to myelin membranes and not bind to degenerating myelin fragments.

By way of example, the radioligands can be administered to white matter and grey matter samples of mouse brain and the fluorescent intensity of the samples can be measured by fluorescent microscopy staining. The fluorescent intensity ratio (FIR) in the same region of interest (ROI) between white matter and grey matter can be calculated. The FIR of the fluorescent trans-stilbene derivatives described herein can be at least about 1.4, 1.5, 1.6, 1.7, 1.8, 1.9, or 2.0.

The radioligands described herein are unique in that they exhibit negligible toxicities as demonstrated in both preclinical and clinical settings, making them suitable candidates for clinical imaging modalities and translational studies. For example, the radioligands can be used for positron emission tomography to detect and quantify myelin contents in vivo.

Typically, the radioligand can be formulated into a pharmaceutical composition prior to use. When a composition described herein is applied to a subject, it is formulated to be compatible with its intended route of application. Examples of routes of application include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, DMSO, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid or cyclodextrin; buffers such as acetates, citrates or phosphates and agents for the adjustment of tonicity such as sodium chloride or dextrose. pH can be adjusted with acids or bases, such as hydrochloric acid or sodium hydroxide.

In one example, a radioligand solution includes a 10 mM radioligand solution. A radioligand solution can also contain saline, DMSO, and HCL. One skilled in the art can utilize the radioligand with pharmaceutical carriers and/or excipients in varying concentrations and formulations depending on the desired use.

In certain embodiments, the radioligands described herein can be contacted with or administered to a subject's brain tissue, central nervous system, and/or peripheral nervous system and utilized for labeling and detecting myelinated regions of the subject's brain tissue, central nervous system, and/or peripheral nervous system. The radioligand may be administered to the subject's nervous or neural tissue either in vivo or in vitro after a tissue sample has been removed from the body. Myelinated regions of the subject's brain are typically found in the white matter of the brain in the myelin sheaths of neuronal axons. Myelin is an outgrowth of glial cells, more specifically oligodendrocytes, which serve as an electrically insulating phospholipid layer surrounding axons of many neurons. For purposes of the present invention, a subject's brain tissue is typically a mammal's brain tissue, such as a primate, e.g., chimpanzee or human; cow; dog; cat; a rodent, e.g., guinea pig, rat, mouse; rabbit; or a bird; reptile; or fish.

In some embodiments, the radioligands described herein can be used for the in vivo detection and localization of myelinated regions of an animal's brain, central nervous system, and/or peripheral nervous system. The radioligand can be administered to the subject or animal as per the examples contained herein, but typically through intravenous injection. "Administered", as used herein, means provision or delivery radioligands in an amount(s) and for a period of time(s) effective to label myelin in an animal's brain, central nervous system, and/or peripheral nervous system. The administration of a compound or composition described herein to a subject may be systemically or locally. For example, a radioligand described herein may be administered systemically, (e.g., parenterally or intravenously) to the subject such that it is delivered throughout the body. Parenteral route includes intravenous, intramuscular, intraperitoneal, intrasternal, and subcutaneous injection or infusion.

An example of a dosing regimen is to administer about 40 to about 50 mg/kg by weight to the animal. In one example at 5 min, the brain concentration of radioligand can range between about 4% to 24% ID/g to ensure sufficient detection of the myelinated regions of the brain, central nervous system, and/or peripheral nervous system.

In some embodiments, the radioligands can be used in analytical, diagnostic, or prognostic applications related to myelin detection. For example, researchers studying normal brains can employ radioligands and methods described herein to examine the morphology and distribution of myelinated tissue in a subject. The radioligands and methods are also applicable in intraoperative nerve labeling, spinal imaging, non-invasive in vivo measurement of myelination levels, and preclinical and basic neuroscience bench research aimed at the study of the function and process of myelination, and the dysfunction and repair of myelin. In some embodiments, researchers studying normal nervous system tissue can employ this method to examine the morphology and distribution of myelinated tissue in an animal.

"Distribution" as used herein is the spatial property of being scattered about over an area or volume. In this case the "distribution of myelinated tissue" is the spatial property of myelin being scattered about over an area or volume included in the animal's brain, central nervous system, or peripheral nervous system tissue. Researchers interested in neurotoxicology and neuropathology can also use this method in several ways. One way is to infer demyelination by the absence of the radioligand labeling compared to normal control tissue (e.g., normal brain). A second way is to study morphological changes in the myelin such as a fragmented or beaded appearance of the myelin sheath.

In yet another embodiment, one skilled in the art can assess and quantify changes in myelin content in vivo. Myelin in a subject's tissue (e.g., brain) can be visualized and quantified using fluorescence or PET imaging. For quantitative analysis, the images are analyzed on a region of interest basis. The radioligand may be visualized any time post administration depending on the application. In one example, at 2 min post administration, signals of the radioligand in proportion to the myelin content in a subject's brain is recorded. In another example, signals are recorded at about 2, 4, 6, 8, 10, 15, 20, 25, 30, 40, 50, 60, 70, 80, 90, 100, 110 and/or 120 min post-administration.

In other embodiments, myelin in an animal's brain, central nervous system, and/or peripheral nervous system can be visualized and quantified using an fluorescence or PET imaging modality. The radioligand may be visualized any time post administration depending on the application as typical radioligands embodied described herein have a low clearance rate due to specific binding in the myelinated regions (e.g., at 60 min, the brain concentration of probe can be <50% of 5 min value to ensure that half time retention in normally myelinated brain is 60 min or longer).

For directly monitoring myelin changes in the white matter of a subject, radioligands described herein can readily penetrate the blood-brain barrier (BBB) and directly bind to the myelinated white matter in proportion to the extent of myelination. Radioligands described herein can be used in conjunction with PET as imaging markers to directly assess the extent of total lesion volumes associated with demyelination. This can provide a direct clinical efficacy endpoint measure of myelin changes and identify effective therapies aimed at protection and repair of axonal damages.

In some embodiments, the radioligand can include an additional imaging moiety that allows the radioligand to be detected by other imaging modalities, such as magnetic resonance imaging. This allows the radioligand to be used in a multi-modal imaging system and provide more sensitive and specific detection of myelin or myelination in tissue of a subject.

The additional imaging moiety can include a magnetic resonance contrast agent that is conjugated, coupled, or bound to an atom of the radioligand and facilitates detection of the radioligand by magnetic resonance imaging. In some aspects, the magnetic resonance contrast agent can include a chelating group, such as a Gd chelating ligand to improve the MRI contrast properties of the radioligand. In one example, as disclosed in U.S. Pat. No. 7,351,401, which is herein incorporated by reference in its entirety, the chelating group can be of the form W-L or V-W-L, wherein V is selected from the group consisting of —COO—, —CO—, —CH$_2$O— and —CH$_2$NH—; W is —(CH$_2$)n where n=0, 1, 2, 3, 4, or 5; and L is:

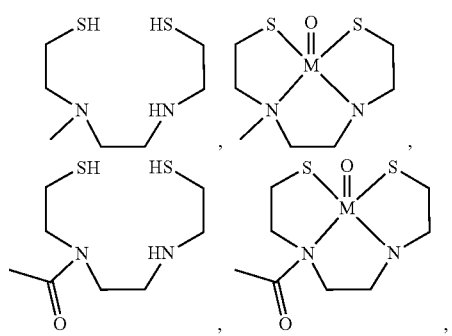

-continued

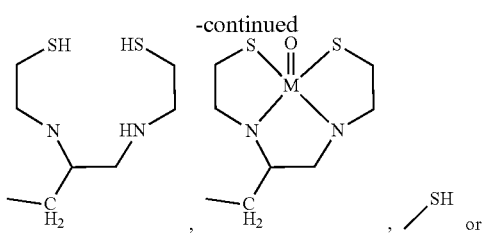

wherein M is selected from the group consisting of Tc and Re; or

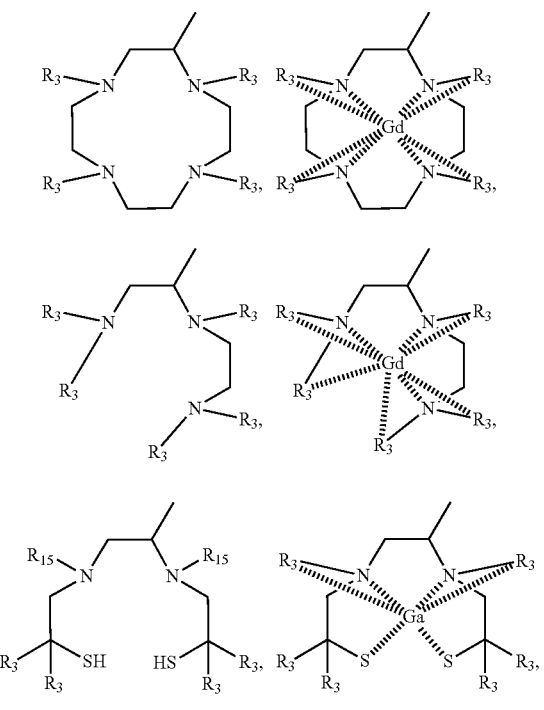

wherein each R₃ is independently is selected from one of:

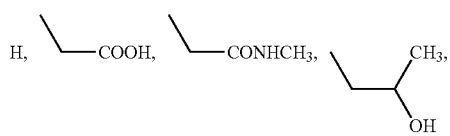

-continued

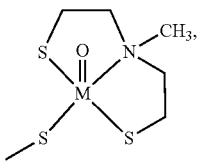

or a myelin binding, chelating compound (with or without a chelated metal group) or a water soluble, non-toxic salt thereof of the form:

wherein each $R_3$ independently is selected from one of:

The chelating group can be coupled to at least one atom of the radioligand through a carbon chain link. The carbon chain link can comprise, for example about 2 to about 10 methylene groups and have a formula of, for example, $(CH_2)_n$ wherein n=2 to 10.

The radioligands can also be used to diagnose a myelination related disorder in an animal through the use of in vivo myelin labeling. Thus, in certain embodiments, solutions containing the radioligands describe herein can be used in the detection of myelin related disorders in an animal.

Methods of detecting a myelin related disorder include the steps of labeling myelin in vivo in the animal's brain tissue with a radioligand described herein, visualizing a distribution of the radioligand in the animal's brain tissue as described above and in the examples, and then correlating the distribution of the radioligand with a myelin related disorder in the animal. In one example of detecting a myelin related disorder, the methods described herein can be used to compare myelinated axonal regions of the brain in the normal tissues of control populations to those of a suspect animal. If the suspect animal has a myelin related disorder, myelin may be virtually absent in lesioned areas thus indicating the presence of a myelin related disorder.

Myelination disorders can include any disease, condition (e.g., those occurring from traumatic spinal cord injury and cerebral infarction), or disorder related to demyelination, remyelination, or dysmyelination in a subject. A myelin related disorder as used herein can arise from a myelination related disorder or demyelination resulting from a variety of neurotoxic insults. Demyelination is the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Barre Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the detection of neurodegenerative autoimmune diseases in an animal and more specifically the detection of multiple sclerosis in an animal.

Another embodiment relates to a method of monitoring the efficacy of a remyelination therapy in an animal. Remyelination is the repair of damaged or replacement of absent myelin in an animal's brain tissue. The methods described include the steps of labeling myelin in vivo in the animal's brain tissue with a radioligand described herein, then detecting a distribution of the radioligand in the animal's brain tissue, and then correlating the distribution of the radioligand as detected in the animal's brain with the efficacy of the remyelination therapy. It is contemplated that the labeling step can occur before, during, and after the course of a therapeutic regimen in order to determine the efficacy of the therapeutic regimen. One way to assess the efficacy of a remyelination therapy is to compare the distribution of the radioligand before remyelination therapy with the distribution of the radioligand after remyelination therapy has commenced or concluded.

Remyelination therapy as used herein refers to any therapy leading to a reduction in severity and/or frequency of symptoms, elimination of symptoms and/or underlying cause, prevention of the occurrence of symptoms and/or their underlying cause, and improvement or remediation of damage related to demyelination. For example, a remyelination therapy can include administration of a therapeutic agent, therapies for the promotion of endogenous myelin repair, or a cell based therapy (e.g., a stem-cell based therapy).

In another embodiment, methods are provided for screening for a myelination response in an animal's brain tissue to an agent. The method includes the initial step of administering an agent to the animal. Myelin in the animal's brain tissue is labeled in vivo with a radioligand as described herein. A distribution of the radioligand in the animal's brain tissue is then detected using a PET imaging. Finally, the distribution of the radioligand with the myelination response in the animal's brain tissue is correlated to the agent. One way to assess the myelination response in the animal's brain tissue is to compare the distribution of the radioligand in an animal's brain tissue, which has been treated with a suspect agent with the distribution of the radioligand in the brain tissue of a control population. "Control Population" as used herein is defined as a population or a tissue sample not exposed to the agent under study but otherwise as close in all characteristics to the exposed group as possible.

The radioligands described herein can also be used to determine if an agent of interest has the potential to modulate demyelination, remyelination, or dysmyelination of axonal regions of an experimental animal's brain tissue.

Example 1

This Example describes the design, synthesis, radiolabeling, and microPET imaging studies of a series of fluorescent trans-stilbene radioligands.

Methods

All chemicals and reagents were used as received without further purification. Glassware was dried in an oven at 130° C. and purged with a dry atmosphere prior to use. Unless otherwise mentioned, reactions were performed open to air. Reactions were monitored by TLC and visualized by a dual short/long wavelength UV lamp. Flash column chromatography was performed using 230-400 mesh silica gel (Fisher). NMR spectra were recorded on a Varian Inova 400 spectrometer and a 500 MHz Bruker Ascend Avance III HD at room temperature. Chemical shifts for $^1$H and $^{13}$C NMR were reported as δ, part per million (ppm), and referenced to an internal deuterated solvent central line. Multiplicity and coupling constants (I) were calculated automatically on MestReNova 10.0, a NMR processing software from Mestrelab Research. The purity of the newly synthesized compounds as determined by analytical HPLC was >95% on C-18 reversed-phase HPLC (Phenomenex, 10×250 mm), eluent: acetonitrile:$H_2O$=60:40, flow rate of 3.0 mL/min. HRMS-ESI mass spectra were acquired on an Agilent Q-TOF. Fluorescence was measured with a Cary Eclipse spectrophotometer using 1×1 cm quartz cuvette in a 10 mM acetonitrile solution.

General Method for Synthesis

3-Hydroxy-4-nitrobenzaldehyde (1) or 4-hydroxy-3-nitrobenzaldehyde (2) (1.5 g, 8.9 mmol) was deprotonated with $K_2CO_3$, (2.48 g, 17.9 mmol) in 20 mL DMF followed by dropwise adding alkylene glycol ditosylate (a-b, 1 equiv) dissolved in 10 mL DMF at 80° C. The reaction mixtures were heated with continuous stirring for additional 6 h. After completion of the reactions, the mixtures were cooled to room temperature, after 30 min, 200 mL ice cold water added, and extracted with 3×50 mL ethyl acetate. The organic phases were combined and washed with 20% sodium bicarbonate (50 mL), 50 mL brine, dried over $MgSO_4$, and evaporated under reduced pressure. The crude products were purified by flash column chromatography in an ethyl acetate-hexane mixture.

2-(5-Formyl-2-nitrophenoxy)ethyl 4-Methylbenzenesulfonate (3)

This dull yellow crystalline solid was eluted in 40% EtOAc:hexane, yield 1.2 g, (60%). $^1$H NMR (400 MHz, chloroform-d) δ 10.07 (s, 1H), 7.95 (d, J=8.1 Hz, 1H), 7.84

(d, J=8.4 Hz, 2H), 7.62 (dd, J=8.1, 1.5 Hz, 1H), 7.56 (d, J=1.5 Hz, 2H), 7.41 (dq, J=7.9, 0.7 Hz, 2H), 4.45 (d, J=1.4 Hz, 4H), 2.49 (s, 3H). $^{13}$C NMR (101 MHz, chloroform-d) δ 190.2, 151.6, 145.5, 139.7, 132.5, 130.2, 128.2, 126.3, 123.6, 113.9, 67.6, 67.3, 21.9.

2-(2-(5-Formyl-2-nitrophenoxy)ethoxy)ethyl 4-Methylbenzene-sulfonate (4)

The off white crystalline compound was eluted in 30% EtOAc:hexane, yield 1.0 g, (40%). $^1$H NMR (400 MHz, chloroform-d) δ 10.02 (s, 1H), 7.90 (d, J=8.2 Hz, 1H), 7.76 (d, J=8.3 Hz, 2H), 7.59 (d, J=1.5 Hz, 1H), 7.54 (d, J=8.1 Hz, 1H), 7.31 (dt, J=8.0, 0.7 Hz, 1H), 4.32-4.21 (m, 2H), 4.20-4.11 (m, 2H), 3.87-3.80 (m, 2H), 3.78-3.71 (m, 2H), 2.41 (s, 3H). $^{13}$C NMR (101 MHz, chloroform-d) δ 190.5, 152.5, 145.1, 139.8, 133.1, 130.0, 128.1, 126.1, 122.9, 114.5, 70.1, 69.5, 69.4, 21.9.

3-(2-Fluoroethoxy)-4-nitrobenzaldehyde (5)

3-Hydroxy-4-nitro-benzaldehyde (1, 1.0 g, 6.0 mmol) was deprotonated with K$_2$CO$_3$ (1.65 g, 12.0 mmol) in 10 mL dry DMF followed by reaction with 1-fluoro-2-iodoethane (0.8 mL, 9.0 mmol, 2.14 g/mL) at 80° C. The reaction was monitored by TLC, and after 6 h no starting material was detected. The reaction mixture was cooled to room temperature, 100 mL ice cold water was added, and the compound was precipitated out, filtered under vacuum, and washed with water and diethyl ether. A yellow amorphous compound was obtained [yield 0.90 g, (70%)] and used without further purification for the next reaction. $^1$H NMR (400 MHz, chloroform-d) δ 10.05 (s, 1H), 7.94 (d, J=7.6 Hz, 1H), 7.69-7.54 (m, 2H), 4.82 (d, J=47.5 Hz, 2H,), 4.45 (d, J=27.0 Hz, 2H,). $^{13}$C NMR (101 MHz, CDCl$_3$) δ 190.3, 139.8, 126.7 (2C), 123.6 (2C), 114.0, 81.4 (d, J$_{C-F}$=173 Hz), 69.4 (d, J$_{C-F}$=21 Hz). $^{19}$F NMR (376 MHz, CDCl$_3$) δ −90.90-−91.16 (C-F coupling) −100.01 (F-decoupling).

2-(4-Formyl-2-nitrophenoxy)ethyl 4-Methylbenzenesulfonate (6)

The white crystalline compound was eluted in 40% EtOAc:hexane, yield 0.45 g (65%). $^1$H NMR (400 MHz, chloroform-d) δ 9.93 (s, 1H), 8.32 (d, J=2.1 Hz, 1H), 8.01 (dd, J=8.8, 2.4 1H), 7.78 (d, J=8.3 Hz, 2H), 7.32 (dd, J=8.4, 0.8 Hz, 2H), 7.18 (d, J=8.7 Hz, 1H), 4.57-4.30 (m, 4H), 2.45 (s, 3H). $^{13}$C NMR (101 MHz, chloroform-d) δ 188.8, 155.6, 145.6, 134.9, 132.3, 130.3, 129.8, 128.1, 127.5, 114.9, 67.7, 67.2, 21.9.

4-(2-Fluoroethoxy)-3-nitrobenzaldehyde (7)

The off white amorphous compound was precipitated out and was used without further purification, yield 1.1 g (86%). $^1$H NMR (400 MHz, chloroform-d) δ 9.95 (s, 1H), 8.36 (dd, J=2.1, 0.8 Hz, 1H), 8.08 (ddd, J=8.7, 2.0, 0.6 Hz, 1H), 7.27-7.25 (m, 1H), 4.94-4.86 (m, 1H), 4.81-4.73 (m, 1H), 4.55-4.40 (m, 2H). $^{13}$C NMR (101 MHz, chloroform-d) δ 188.9, 156.2, 134.8, 129.8, 127.7, 115.0, 82.2, 80.4, 69.5, 69.3. $^{19}$F NMR (376 MHz, chloroform-d) δ −90-−91.13 (m), −100.01 (s).

tert-Butyl (4-((Diethoxyphosphoryl)methyl)phenyl)carbamate (9)

Compound 9 was synthesized according to our earlier published method. To a 100 mL round-bottom flask with a magnetic stir bar, diethyl 4-aminobenzylphosphonate (8, 5.0 g, 20.56 mmol), di-tert-butyl dicarbonate (4.50 g, 21.0 mmol), THF (25 mL), and water (10 mL) were added. The reaction was stirred at room temperature open to air overnight. After completion of the reaction, THF was evaporated under vacuum, and the resulting residue was diluted with water and extracted with ethyl acetate (50 mL×3) three times. The organic layers were combined and washed twice with water (50 mL×2) and once with brine (50 mL). The organic layer was dried over MgSO$_4$, filtered, and evaporated under reduced pressure. The resulting white amorphous compound was obtained [yield 6.5 g (95%)] and used without further purification. $^1$H NMR (400 MHz, chloroform-d) δ 7.30 (br d, J=8.4 Hz, 2H), 7.17-7.19 (m, 2H), 6.87 (br s, 1H), 4.04-3.91 (m, 4H), 3.07 (d, $^2$J$_H$, p=21.2 Hz, 2H), 1.49 (s, 9H), 1.22 (td, $^3$J$_H$, H=6.8 Hz, $^4$J$_H$, p=0.4 Hz, 6H). $^{13}$C NMR (100 MHz, chloroform-d) δ 152.8, 137.4, 130.1, 125.5, 118.4, 80.3, 62.0, 32.9 (d, J$_{c,p}$=138 Hz, 1C), 28.8, 16.3.

General Method for Alkylation of tert-Butyl (4-((Diethoxyphosphoryl)methyl)phenyl)carbamate (10-14)

To an oven-dried 100 mL round-bottom flask purged with argon gas and fitted with a magnetic stirrer were added sodium hydride (0.150 g, 5.82 g, 95%) and tert-butyl (4-((diethoxyphosphoryl)methyl)phenyl)-carbamate (9, 1.0 g, 2.9 mmol). The mixture was purged with argon gas, and dry THF (25 mL) at 0° C. was added. Iodo-alkane (4.0 equiv) was added dropwise after 30 min at 0° C. under argon gas. The reaction was stirred under argon and allowed to reach room temperature overnight. After completion, the reaction was quenched with water, and THF was removed by vacuum. The residue was dissolved in dichloromethane (DCM) and water, and the aqueous layer was extracted three times with DCM (30 mL×3). The organic layers were combined and washed twice with water (50 mL×2) and once with brine (50 mL). The organic layer was dried over MgSO$_4$ and then filtered and concentrated to yield the desired products 10-14 as sticky oil. This was purified over a silica flash column using hexane:ethyl acetate as eluent as required with derivatives.

tert-Butyl (4-((Diethoxyphosphoryl)methyl)phenyl) (methyl)-carbamate (10)

This dark yellow sticky oil was used without further purification, yield 0.80 g, (76%). $^1$H NMR (400 MHz, chloroform-d) δ 7.24-7.25 (m, 2H), 7.16 (d, J=8.0 Hz, 2H), 4.07-3.94 (m, 4H), 3.22 (s, 3H), 3.11 (d, $^3$J$_H$, p=21.6 Hz, 2H), 1.42 (s, 9H), 1.23 (t, J=7.2, 6H). $^{13}$C NMR (100 MHz, chloroform-d) δ 154.5, 142.4, 129.7, 128.4, 125.4, 80.1, 61.9, 37.1, 33.0 (d, $^2$J$_{C,P}$=138 Hz, 1C), 28.1, 16.3.

tert-Butyl (4-((diethoxyphosphoryl)methyl)phenyl) (ethyl)-carbamate (11)

This clear sticky oil was eluted in 30% EtOAc:hexane, yield 0.65 g (40%). $^1$H NMR (400 MHz, chloro-form-d) δ 7.28-7.23 (m, 2H), 7.11 (d, J=8.0 Hz, 2H), 4.00 (dqd, J=8.3, 7.1, 3.7 Hz, 4H), 3.64 (q, J=7.1 Hz, 2H), 3.13 (d, J$_{H,P}$=21.6 Hz, 2H), 1.40 (s, 9H), 1.23 (td, J=7.1, 0.4 Hz, 6H), 1.11 (t, J=7.1 Hz, 3H). $^{13}$C NMR (101 MHz, chloroform-d) δ 141.0, 129.9, 129.8, 129.0, 128.9, 126.9, 79.7, 62.0, 61.9, 44.6, 33.1 (d, J$_{C,P}$=138 Hz, 1C), 28.1, 16.2, 16.2, 13.6.

tert-Butyl (4-((Diethoxyphosphoryl)methyl)phenyl) (propyl)-carbamate (12)

This clear sticky oil was eluted in 30% EtOAc:hexane, yield 0.400 g, (25%). $^1$H NMR (400 MHz, chloroform-d) δ 7.23 (d, J=2.5 Hz, 1H), 7.21 (d, J=2.6 Hz, 1H), 7.08 (d, J=8.0 Hz, 2H), 3.97 (dqd, J=8.3, 7.1, 3.9 Hz, 4H), 3.57-3.47 (m, 2H), 3.10 (d, $J_{H,P}$=21.6 Hz, 2H), 1.54-1.45 (m, 2H), 1.37 (s, 9H), 1.22-1.17 (m, 6H), 0.83 (t, J=7.4 Hz, 3H). $^{13}$C NMR (101 MHz, chloroform-d) δ 141.3, 141.2, 130.0, 129.9, 128.0, 127.1, 127.0, 127.0, 79.8, 62.1, 62.0, 51.5, 33.2 (d, $J_{C,P}$=138 Hz, 1C), 28.2, 21.5, 16.3, 16.2, 11.0.

tert-Butyl (4-((Diethoxyphosphoryl)methyl)phenyl) (isopropyl)-carbamate (13)

This yellow Oil was eluted in 25% EtOAc:hexane, yield 0.41 g (25%). $^1$H NMR (400 MHz, chloroform-d) δ 7.24 (dd, J=7.8, 2.0 Hz, 2H), 6.97 (d, J=8.0 Hz, 2H), 4.56-4.41 (m, 1H), 4.02-3.89 (m, 4H), 3.12 (d, $J_{H,P}$=21.6 Hz, 2H), 1.31 (s, 9H), 1.18 (td, J=7.1, 0.6 Hz, 6H), 1.03 (dd, J=6.8, 0.8 Hz, 6H). $^{13}$C NMR (101 MHz, chloroform-d) δ 130.1, 130.0, 129.8, 129.8, 129.7, 79.4, 62.0, 62.0, 33.2 (d, $J_{C,P}$=138 Hz, 1C), 28.1, 21.2, 16.2, 16.2.

tert-Butyl sec-Butyl(4-((diethoxyphosphoryl)methyl) phenyl)-carbamate (14)

This clear oil was eluted in 30% EtOAc:hexane, yield 0.20 g (15%). $^1$H NMR (400 MHz, chloroform-d) δ 7.29-7.25 (m, 2H), 7.08-6.98 (m, 2H), 4.21 (d, J=10.3 Hz, 1H), 4.06-3.92 (m, 4H), 3.14 (d, $J_{H,P}$=21.6 Hz, 2H), 1.54 (dt, J=13.5, 7.5 Hz, 1H), 1.35 (s, 9H), 1.28 (d, J=7.1 Hz, 1H), 1.26-1.17 (m, 6H), 1.05 (d, J=6.9 Hz, 3H), 0.95 (t, J=7.4 Hz, 3H). $^{13}$C NMR (101 MHz, CDCl$_3$) δ 154.9, 138.1, 129.9, 129.8, 129.7, 129.6, 129.6, 129.5, 129.5, 79.3, 62.0, 61.9, 54.3, 33.2 (d, $J_{C,P}$=138 Hz, 1C), 28.2, 28.1, 19.1, 16.2, 16.1, 11.2.

General Method for the Synthesis of 16-22 (Scheme 3)

To an oven-dried 100 mL round-bottom flask purged with argon and fitted with a magnetic stirrer was added sodium hydride (2.0 eq., 60% dispersion in mineral oil). The flask was purged with argon, and dry DMF 2.0 mL was added. The compound (10-15, 1.1 equiv) was dissolved in dry DMF (2.0 mL) and transferred via syringe in a NaHDMF mixture to a flask. The mixture was stirred under argon at 0° C. for 1 h. 3 or 6 (1.0 equiv) was dissolved in dry DMF (2 mL) and added to the reaction mixture via syringe under argon at 0° C. The reaction was stirred for 2 h at 0° C. in the dark under argon. The reaction was quenched with water (25 mL) and extracted with ethyl acetate (30 mL×3) three times. The organic layers were combined and washed with water (25 mL×2) twice and once with brine (25 mL). The organic layer was dried over MgSO$_4$, filtered, and concentrated to give sticky oil as crude product. This was purified by dissolving in a minimal amount of DCM and made slurry with silica gel and dried under vacuum. The compound was eluted in 10-15% ethyl acetate:hexane in a flash column.

(E)-2-(5-(4-((tert-Butoxycarbonyl)(methyl)amino styryl)-2-nitrophenoxy)ethyl-4-methylbenzene-sulfonate (16)

This yellow amorphous compound was eluted in 15% EtOAc:hexane, yield 0.140 g (40%). $^1$H NMR (400 MHz, chloroform-d) δ 7.88 (d, J=8.5 Hz, 1H), 7.84-7.80 (m, 2H), 7.50 (d, J=8.5 Hz, 2H), 7.37-7.33 (m, 2H), 7.29 (d, J=8.4 Hz, 2H), 7.22-7.19 (m, 1H), 7.18-7.16 (m, 1H), 7.11 (d, J=1.7 Hz, 1H), 6.99 (d, J=16.3 Hz, 1H), 4.41 (q, J=2.1 Hz, 4H), 3.29 (s, 3H), 2.44 (s, 3H), 1.48 (s, 9H). $^{13}$C NMR (101 MHz, chloroform-d) δ 145.4, 144.5, 144.2, 132.8, 130.2, 128.2, 127.4, 126.7, 125.9, 125.6, 119.4, 113.0, 67.8, 37.3, 28.5, 21.9.

(E)-2-(5-(4-((tert-Butoxycarbonyl)(ethyl)amino) styryl)-2-nitrophenoxy)ethyl-4-methylbenzene-sulfonate (17)

The yellow sticky solid product was eluted in a silica flash column with 15% EtOAc:hexane. The yellow amorphous product yield 0.125 (40%). $^1$H NMR (400 MHz, chloroform-d) δ 7.87 (d, J=8.5 Hz, 1H), 7.84-7.80 (m, 2H), 7.50 (d, J=8.5 Hz, 2H), 7.38-7.33 (m, 2H), 7.24 (d, J=8.5 Hz, 2H), 7.22-7.19 (m, 1H), 7.18-7.16 (m, 1H), 7.11 (d, J=1.7 Hz, 1H), 7.00 (d, J=16.3 Hz, 1H), 4.48-4.35 (m, 4H), 3.70 (q, J=7.1 Hz, 2H), 2.44 (s, 3H), 1.46 (s, 9H), 1.17 (t, J=7.1 Hz, 3H). $^{13}$C NMR (101 MHz, chloroform-d) δ 152.3, 145.4, 144.1, 143.1, 133.5, 132.7, 132.5, 130.1, 128.1, 127.4, 127.1, 126.7, 126.0, 119.3, 112.9, 80.50, 67.7, 67.6, 45.0, 28.5, 21.8, 14.1.

(E)-2-(5-(4-((tert-Butoxycarbonyl)(propyl)amino) styryl)-2-nitrophenoxy)ethyl-4-methylbenzene-sulfonate (18)

The yellow crystalline compound was eluted on a silica flash column in 15% EtOAc:hexane. Yield 0.165 g (35%). $^1$H NMR (400 MHz, chloroform) δ 7.87 (d, J=8.5 Hz, 1H), 7.85-7.79 (m, 2H), 7.50 (d, J=8.4 Hz, 2H), 7.35 (dt, J=7.9, 0.7 Hz, 2H), 7.23 (d, J=8.4 Hz, 2H), 7.21-7.19 (m 1H), 7.18-7.16 (m 1H), 7.11 (d, J=1.7 Hz, 1H), 7.00 (d, J=16.2 Hz, 1H), 4.46-4.37 (m, 4H), 3.67-3.57 (m, 2H), 2.44 (s, 3H), 1.60 (s, 1H), 1.57 (s, 1H), 1.45 (s, 9H), 0.89 (t, J=7.4 Hz, 3H). $^{13}$C NMR (101 MHz, chloroform-d) δ 152.3, 145.4, 144.1, 133.5, 132.7, 132.5, 130.1, 128.1, 127.4, 127.3, 126.7, 126.0, 119.3, 112.9, 80.5, 67.7, 67.6, 51.6, 28.5, 21.9, 21.8, 11.3.

(E)-2-(5-(4-((tert-Butoxycarbonyl)(isopropyl)amino) styryl)-2-nitrophenoxy)ethyl-4-methylbenzene-sulfonate (19)

The yellow amorphous compound was eluted on a silica flash column in 15% EtOAc:hexane, yield 0.065 g (30%). $^1$H NMR (500 MHz, chloroform) δ 7.87 (dd, J=8.5, 2.0 Hz, 1H), 7.84-7.79 (m, 2H), 7.53-7.48 (m, 2H), 7.35 (d, J=7.8 Hz, 2H), 7.23-7.17 (m, 2H), 7.14-7.09 (m, 3H), 7.06-7.00 (m, 1H), 4.57-4.46 (m, 1H), 4.42 (h, J=4.3, 3.7 Hz, 4H), 2.44 (s, 3H), 1.39 (s, 9H), 1.13 (dd, J=6.9, 2.0 Hz, 6H). $^{13}$C NMR (126 MHz, chloroform-d) δ 154.9, 152.4, 145.4, 144.1, 140.2, 138.8, 134.8, 132.8, 132.6, 130.5, 130.2, 128.2, 127.3, 126.7, 126.5, 119.5, 113.1, 80.1, 67.8, 67.8, 28.6, 21.9, 21.8.

(E)-2-(5-(4-((tert-Butoxycarbonyl)(sec-butyl)amino) styryl)-2-nitrophenoxy)ethyl-4-methylbenzene-sulfonate (20)

The yellow sticky solid was eluted in 10% EtOAc:hexane, yield 0.040 g (15%). 1H NMR (400 MHz, chloroform-d) δ 7.88 (d, J=8.5 Hz, 1H), 7.85-7.80 (m, 2H), 7.53-7.49 (m, 2H), 7.37-7.33 (m, 2H), 7.23-7.20 (m, 1H), 7.18 (d, J=1.9

Hz, 1H), 7.15-7.10 (m, 3H), 7.02 (d, J=16.3 Hz, 1H), 4.45-4.38 (m, 4H), 4.23 (d, J=7.0 Hz, 1H), 2.44 (s, 3H), 1.67-1.58 (m, 1H), 1.40 (s, 9H), 1.37-1.32 (m, 1H), 1.12 (d, J=6.8 Hz, 3H), 0.98 (t, J=7.4 Hz, 3H). 13C NMR (101 MHz, chloroform-d) δ 152.3, 145.4, 144.0, 134.6, 132.7, 132.5, 130.2, 130.1, 130.1, 128.1, 127.2, 126.7, 126.4, 119.4, 113.0, 80.1, 67.7, 67.7, 66.8, 55.2, 28.7, 28.5, 21.8, 19.7, 11.6.

(E)-2-(2-Nitro-5-(4-nitrostyryl)phenoxy)ethyl-4-methylbenzenesulfonate (21)

A yellow amorphous precipitate formed after quenching with water and was then washed several times with water and diethyl ether. The yellow amorphous product yield was 0.150 g (75%). H NMR (400 MHz, DMSO-d6) δ 8.31-8.25 (m, 2H), 7.93 (d, J=8.4 Hz, 1H), 7.91-7.86 (m, 2H), 7.79-7.74 (m, 2H), 7.65 (d, J=16.5 Hz, 1H), 7.60-7.52 (m, 2H), 7.42 (t, J=8.2 Hz, 3H), 4.50-4.34 (m, 4H), 2.39 (s, 3H). $^{13}$C NMR (101 MHz, DMSO) δ 151.7, 147.4, 145.7, 143.7, 143.2, 139.1, 132.6, 131.7, 131.1, 130.8, 128.5, 128.4, 128.2, 128.1, 126.5, 126.5, 124.8, 124.8, 124.7, 120.4, 113.6, 69.2, 67.6, 21.8.

(E)-2-(5-(4-((tert-Butoxycarbonyl)(methyl)amino) styryl)-2-nitrophenoxy)ethyl-4-methylbenzene-sulfonate (22)

The yellow crystalline compound was purified over a silica flash column in 20% EtOAc:hexane, yield 0.240 g (50%). $^1$H NMR (500 MHz, chloroformd) δ 7.96 (s, 1H), 7.82 (d, J=8.1 Hz, 2H), 7.62 (dd, J=8.6, 2.2 Hz, 1H), 7.46 (d, J=8.3 Hz, 2H), 7.37 (d, J=8.1 Hz, 2H), 7.27 (s, 2H), 7.07-7.02 (m, 2H), 6.97 (d, J=16.3 Hz, 1H), 4.45-4.33 (m, 4H), 3.29 (s, 3H), 2.46 (s, 3H), 1.49 (s, 9H). $^{13}$C NMR (126 MHz, chloroform-d) δ 154.5, 150.3, 145.1, 143.6, 133.2, 132.3, 131.5, 129.9, 129.3, 127.8, 126.6, 125.4, 125.0, 122.9, 115.3, 80.5, 67.4, 67.4, 37.0, 28.2, 21.6.

Synthesis of (E)-2-(2-(2-Nitro-5-(4-nitrostyryl)phenoxy)ethoxy)-ethyl-4-methylbenzene-sulfonate 23 (Scheme 4)

To an oven-dried 100 mL round-bottom flask purged with argon and fitted with a magnetic stirring bar was added sodium hydride (0.80 g, 2.0 mmol, 60% dispersion in mineral oil). The flask was purged with argon, and dry DMF 2.0 mL was added. The diethyl (4-nitrobenzyl) phosphonate (15, 0.30 g, 1.1 mmol) was dissolved in dry DMF (2.0 mL), and the NaH-DMF mixture was transferred via syringe to a flask. The mixture was then stirred under argon at 0° C. for 1 h. The tosylated 4-nitrobenzaldehyde (4, 0.360 g 1.0 mmol) was dissolved in dry DMF (2 mL) and added to the reaction mixture via syringe under argon at 0° C. The reaction was stirred again for 2 h at 0° C. in the dark under argon. The reaction was quenched with 25 mL of ice cold water, and the compound precipitated out. It was then filtered under vacuum, washed with water several times followed by diethyl ether, and used for the next step without further purification. The yellow amorphous compound was dried under high vacuum, yield 0.390 g (80%). $^1$H NMR (400 MHz, DMSO-d6) δ 8.31-8.25 (m, 2H), 7.95 (d, J=8.4 Hz, 1H), 7.92-7.87 (m, 2H), 7.79-7.74 (m, 2H), 7.68 (d, J=16.5 Hz, 1H), 7.64-7.55 (m, 2H), 7.42 (dd, J=9.1, 3.0 Hz, 3H), 4.30 (t, J=4.6 Hz, 2H), 4.19-4.09 (m, 2H), 3.79-3.62 (m, 4H), 2.37 (s, 3H). $^{13}$C NMR (101 MHz, DMSO) δ 151.8, 146.7, 144.8, 143.1, 142.6, 138.5, 132.3, 131.2, 130.4, 130.1, 127.8, 127.6, 125.9, 124.2, 119.4, 113.1, 70.0, 69.1, 68.5, 68.2, 21.1.

(E)-2-(2-(2-Fluoroethoxy)ethoxy)-1-nitro-4-(4-nitrostyryl)benzene (24)

Compound (23, 0.15 g, 0.28 mmol) and Kryptofix 2.2.2. ($K_{222}$, 0.33 g, 0.85 mmol) with CsF (0.09 g, 0.57 mmol) as the source of fluoride-19 were mixed together in a 100 mL round-bottom flask in dry acetonitrile (20 mL), and the reaction was purged with argon. The reaction mixture was heated at 80° C. for 4 h and monitored by TLC. Once the reaction was complete, acetonitrile was evaporated under reduced pressure, and the reaction was quenched with ice cold water. The dark brown precipitate was filtered under vacuum and washed with water several times and diethyl ether once. The light brown amorphous product yield was 0.090 g, and 84% was used with further purification. $^1$H NMR (400 MHz, chloroform-d) δ 8.26 (d, J=8.3 Hz, 2H), 7.92 (d, J=8.0 Hz, 1H), 7.68 (d, J=8.5 Hz, 2H), 7.29 (d, J=1.6 Hz, 1H), 7.25-7.18 (m, 3H), 4.60 (dt, J=47.8, 4.0 Hz, 2H), 4.37 (t, J=4.7 Hz, 2H), 3.99 (t, J=4.6 Hz, 2H), 3.88 (dt, J=30.1, 3.8 Hz, 3H). $^{13}$C NMR (101 MHz, chloroform-d) δ 170.4, 156.3, 153.2, 136.1, 135.6, 134.5, 131.1, 131.1, 131.0, 130.5, 127.7, 127.6, 126.7, 124.5, 119.4, 117.5, 113.6, 105.3, 94.6, 86.6 (d, JC-F=164 Hz), 70.1 (JC-F, J=43 Hz). 19F NMR (376 MHz, chloroform-d) δ −100.01.

(E)-4-(4-Aminostyryl)-2-(2-(2-fluoroethoxy)ethoxy) aniline (25)

To a 100 mL round-bottom flask with a magnetic stirring bar was added tin(II) chloride (0.285 g, 1.5 mmol). (E)-2-(2-(2-fluoroethoxy)-ethoxy)-1-nitro-4-(4-nitrostyryl)benzene (24, 0.050 g, 0.15 mmol) was added to the tin(II) chloride solution of ethyl acetate (15 mL) and ethanol (10 mL). The reaction mixture was refluxed under a water-cooled condenser in an oil bath at 70° C. and stirred overnight open to air. The reaction was monitored via TLC and after completion of the reaction was cooled to room temperature, and the solvent was removed by vacuum. The compound was dissolved in aq $Na_2CO_3$ (20%) until bubbles stopped forming and was washed with ethyl acetate 3 times (30 mL×3), water (50 mL×2), followed by brine (50 mL). The organic layer was dried over the $MgSO_4$, filtered, and concentrated to give the crude 25. The crude product was dissolved in minimal DCM and purified on silica by flash column chromatography with a mobile phase of EtOAc: hexane, and 25 was eluted in 10-15% EtOAc:hexane yielding a sticky brown solid, yield 0.02 g, (49%). $^1$H NMR (400 MHz, chloroform-d) δ 7.28-7.24 (m, 2H), 6.95 (d, J=1.8 Hz, 1H), 6.90 (dd, J=8.0, 1.8 Hz, 1H), 6.78 (s, 2H), 6.66-6.63 (m, 2H), 6.62 (d, J=1.9 Hz, 1H), 4.68-4.61 (m, 1H), 4.57-4.49 (m, 1H), 4.27-4.15 (m, 2H), 3.90-3.86 (m, 2H), 3.86-3.80 (m, 2H), 3.79-3.72 (m, 3H). $^{13}$C NMR (101 MHz, chloroform-d) δ 146.2, 145.3, 136.1, 128.61, 128.4, 127.1, 125.3, 125.0, 120.4, 115.1, 115.0, 110.1, 81.8 (d, JC-F=171 Hz), 69.4 (d, JC-F=21.0 Hz). 19F NMR (376 MHz, chloroform-d) δ −89.8--90.7 (m), −100.0.

General Method for the Synthesis of 26-31 (Scheme 5, Step (i))

To an oven-dried 100 mL round-bottom flask with a magnetic stirring bar was added sodium hydride (NaH, 2.0 equiv, 60%). The flask was purged with argon, and 2.0 mL dry DMF was added. The solution was stirred under argon in an ice bath (0° C.). Boc-N-R1-diethyl benzoylphosphonate and diethyl (4-nitrobenzyl)phosphonate (10-15, 1.2 equiv) in 2.0 mL dry DMF were added to the solution of NaH. This sodium hydride and intermediate (10-15) mixture was stirred at 0° C. under argon for 1 h. Then 2.0 mL dry DMF solution of fluorinated nitrobenzaldehyde was transferred via syringe to the reaction mixture under argon at 0° C. The reaction was continued for another 2 h at 0° C. under argon and monitored via TLC. Once completed, the reaction was quenched with ice cold water (50 mL) and extracted with ethyl acetate (50 mL×3) three times. The organic layer was washed twice with water (50 mL×2) and once with brine (50 mL). The organic layer was dried over $MgSO_4$, filtered, and concentrated to give a yellow crude solid/oil. The solid was dissolved in 2 mL ethyl acetate and loaded onto a silica column and eluted with ethyl acetate and hexane.

tert-Butyl (E)-(4-(3-(2-Fluoroethoxy)-4-nitrostyryl) phenyl)-(methyl)carbamate (26)

This yellow amorphous compound was purified on a silica flash column in 15% EtOAc:hexane, yield 0.080 g, (30%). $^1$H NMR (400 MHz, chloroform-d) δ 7.91-7.86 (m, 1H), 7.47 (d, J=8.1 Hz, 2H), 7.27 (d, J=8.1 Hz, 2H), 7.19 (d, J=7.2 Hz, 1H), 7.14 (d, J=2.9 Hz, 2H), 7.00 (d, J=16.4 Hz, 1H), 4.91-4.85 (m, 1H), 4.80-4.71 (m, 1H), 4.41 (dt, J=26.9, 3.7 Hz, 2H), 3.27 (s, 3H), 1.46 (s, 9H). $^{13}$C NMR (101 MHz, chloroform-d) δ 152.8, 144.4, 144.1, 133.0, 132.8, 132.6, 128.0, 127.3, 126.8, 126.7, 126.1, 125.6, 119.2, 113.2, 81.8 (d, $J_{C-F}$=171 Hz), 69.4 (d, $J_{C-F}$=21 Hz), 37.3, 28.5. $^{19}$F NMR (376 MHz, chloroform-d) δ -91.0 (m), -100.01 (s).

tert-Butyl (E)-Ethyl(4-(3-(2-fluoroethoxy)-4-nitrostyryl)phenyl)-carbamate (27)

The yellow sticky solid was purified on a silica flash column in 15% EtOAc:hexane, yield 0.110 g, (70%). $^1$H NMR (400 MHz, chloroform-d) δ 7.91 (d, J=8.4 Hz, 1H), 7.50 (d, J=8.4 Hz, 2H), 7.24 (s, 1H), 7.24-7.21 (m, 2H), 7.21-7.19 (m, 1H), 7.18-7.16 (m, 2H), 7.02 (d, J=16.3 Hz, 1H), 4.93-4.87 (m, 1H), 4.82-4.76 (m, 1H), 4.48-4.38 (m, 2H), 3.70 (q, J=7.1 Hz, 2H), 1.46 (s, 9H), 1.17 (t, J=7.1 Hz, 3H). $^{13}$C NMR (101 MHz, chloroform-d) δ 152.7, 144.0, 143.1, 133.6, 132.5, 127.4, 127.1, 126.7, 126.2, 119.1, 113.2, 81.8 (d, $J_{C-F}$=171 Hz), 69.4 (d, $J_{C-F}$=21 Hz), 45.0, 28.5, 14.1. $^{19}$F NMR (376 MHz, chloroform-d) δ -91.0 (m), -100.01 (s).

tert-Butyl (E)-(4-(3-(2-Fluoroethoxy)-4-nitrostyryl) phenyl)-(propyl)carbamate (28)

This yellow amorphous compound was purified on a silica flash column in 15% EtOAc:hexane, yield 0.150 g, (50%). $^1$H NMR (400 MHz, chloroform-d) δ 7.89 (d, J=8.5 Hz, 1H), 7.48 (d, J=8.5 Hz, 2H), 7.22 (s, 1H), 7.21-7.18 (m, 2H), 7.16-7.13 (m, 2H), 7.00 (d, J=16.3 Hz, 1H), 4.91-4.86 (m, 1H), 4.79-4.74 (m, 1H), 4.47-4.43 (m, 1H), 4.40-4.36 (m, 1H), 3.63-3.57 (m, 2H), 1.57 (d, J=7.4 Hz, 1H), 1.53 (d, J=5.8 Hz, 1H), 1.43 (s, 9H), 0.87 (t, J=7.4 Hz, 3H). $^{13}$C NMR (101 MHz, chloroform-d) δ 152.8, 144.0, 143.3, 133.6, 132.6, 127.4, 127.3, 126.7, 126.3, 119.2, 113.3, 81.8 (d, $J_{C-F}$=171 Hz), 69.4 (d, $J_{C-F}$=21 Hz), 51.7, 28.5, 22.0, 11.4. $^{19}$F NMR (376 MHz, chloroform-d) δ -91.0 (m), -100.01 (s).

tert-Butyl (E)-(4-(3-(2-Fluoroethoxy)-4-nitrostyryl) phenyl)-(isopropyl)carbamate (29)

This yellow crystalline compound was purified on a silica flash column in 15% EtOAc:hexane, yield 0.165 g, (40.0%). $^1$H NMR (400 MHz, chloroform-d) δ 7.91 (d, J=8.4 Hz, 1H), 7.51 (d, J=8.3 Hz, 2H), 7.24-7.20 (m, 1H), 7.19-7.17 (m, 2H), 7.14-7.09 (m, 2H), 7.05 (d, J=16.3 Hz, 1H), 4.93-4.86 (m, 1H), 4.78 (d, J=4.1 Hz, 1H), 4.57-4.49 (m, 1H), 4.48-4.37 (m, 2H), 1.39 (s, 9H), 1.13 (d, J=6.8 Hz, 6H). $^{13}$C NMR (101 MHz, chloroform-d) δ 152.8, 143.9, 134.8, 132.6, 130.5, 127.3, 126.7, 126.7, 119.2, 113.3, 81.8 (d, $J_{C-F}$=171 Hz), 69.4 (d, $J_{C-F}$=21 Hz), 48.9, 28.6, 21.8. $^{19}$F NMR (376 MHz, chloroform-d) δ -91.0 (m), -100.01 (s).

tert-Butyl (E)-sec-Butyl(4-(3-(2-fluoroethoxy)-4-nitrostyryl)-phenyl)carbamate (30)

This yellow crystalline, compound was purified on a silica flash column in 15% EtOAc:hexane, yield 0.105 g (55%). $^1$H NMR (500 MHz, chloroform-d) δ 7.96 (dd, J=8.5, 1.9 Hz, 1H), 7.60-7.52 (m, 2H), 7.35-7.25 (m, 2H), 7.24 (s, 1H), 7.21-7.15 (m, 2H), 7.10 (dd, J=16.3, 1.9 Hz, 1H), 4.89 (dt, J=47.3, 3.0 Hz, 2H), 4.49 (dt, J=26.9, 3.1 Hz, 2H), 4.28 (h, J=7.3 Hz, 1H), 1.67 (dt, J=9.9, 4.8 Hz, 2H), 1.46 (s, 9H), 1.18 (dd, J=6.9, 1.9 Hz, 3H), 1.04 (td, J=7.4, 1.8 Hz, 3H). $^{13}$C NMR (126 MHz, chloroform-d) δ 155.1, 152.7, 143.9, 140.5, 138.9, 134.6, 132.5, 130.1, 127.2, 126.6, 126.6, 119.2, 113.3, 81.8 (d, $J_{C-F}$=171 Hz), 69.4 (d, $J_{C-F}$=21 Hz), 55.2, 28.7, 28.5, 19.6, 11.6. $^{19}$F NMR (376 MHz, chloroform-d) δ -90.93 (tt, J=47.3, 26.9 Hz), -100.01.

(E)-2-(2-Fluoroethoxy)-1-nitro-4-(4-nitrostyryl)benzene (31)

The yellow amorphous, precipitate was washed with water and diethyl ether, yield 0.280 g, (80%). $^1$H NMR (400 MHz, DMSO-d6) δ 8.29 (d, J=8.8 Hz, 2H), 7.96 (d, J=8.5 Hz, 1H), 7.90 (d, J=8.6 Hz, 2H), 7.66 (s, 2H), 7.59 (d, J=16.4 Hz, 1H), 7.43 (d, J=8.5 Hz, 1H), 4.80 (d, J=47.4 Hz, 2H), 4.52 (d, J=29.8 Hz, 2H). $^{13}$C NMR (101 MHz, DMSO) δ 151.5, 143.1, 142.6, 131.2, 130.5, 127.8, 125.9, 124.2, 119.7, 113.2, 81.8 (d, $J_{C-F}$=171 Hz), 69.4 (d, $J_{C-F}$=21 Hz). $^{19}$F NMR (376 MHz, DMSO) δ -89.76, -89.84.

General Method for the Boc-Deprotection and Reduction (32-39, Scheme 5, Step (ii))

To a 100 mL round-bottom flask fitted with a stirring bar was added tin(II) chloride (10 equiv). The compound to be reduced (26-31, 38) was dissolved in ethyl acetate (25 mL) and ethanol (15 mL) and added to tin(II) chloride. The mixture was fitted with a water condenser, heated to 80° C. for 6 h open to air in the dark. The reaction were monitored through TLC, and after completion, solvent was removed by vacuum. The residue was quenched by aq $Na_2CO_3$ (20%) until bubbles stopped forming. The compound was extracted in ethyl acetate (30 mL×3) three times and washed with aq $Na_2CO_3$ (20%) 2 times (30 mL×2) and once with water (50 mL) followed by brine (50 mL). It was then dried over $Na_2SO_4$, and solvent was removed by reducing the pressure. The crude product was dissolved in a minimal DCM slurry on silica and purified on silica by flash column chromatography using 10-15% EtOAc:hexane.

(E)-4-(4-Amino-3-(2-fluoroethoxy)styryl)-N-methylaniline (32)

The brown amorphous compound was purified on a silica flash column and eluted with 20% EtOAc:hexane, yield 0.02 g, (55%). ¹H NMR (400 MHz, chloroform-d) δ 7.38 (d, J=8.6 Hz, 2H), 7.00 (dd, J=4.2, 2.4 Hz, 2H), 6.87 (d, J=1.9 Hz, 2H), 6.75 (d, J=8.4 Hz, 1H), 6.68-6.60 (m, 2H), 4.93-4.75 (m, 2H), 4.40-4.29 (m, 2H), 2.91 (s, 3H). ¹³C NMR (101 MHz, chloroform-d) δ 148.9, 146.3, 129.4, 127.6, 127.5, 125.9, 125.0, 120.9, 115.6, 112.8, 112.8, 112.7, 112.7, 110.0, 81.2 (d, $J_{C-F}$=181 Hz), 68.1 (d, $J_{C-F}$=21 Hz), 30.9. ¹⁹F NMR (376 MHz, chloroform-d) δ −90.53--91.75 (m), −100.01. HR-MS (ESI) m/z calculated for ($C_{17}H_{19}FN_2O$) [M+H]⁺ 287.1554, found 287.1550. HPLC purity: 96.26%, retention time 10.07 min.

(E)-4-(4-Amino-3-(2-fluoroethoxy)styryl)-N-ethyl-aniline (33)

The brown amorphous compound was purified on a silica flash column and eluted with 20% EtOAc:hexane, yield 0.045 g (64%). ¹H NMR (400 MHz, chloroform-d) δ 7.34-7.29 (m, 2H), 6.97-6.93 (m, 2H), 6.81 (d, J=1.6 Hz, 2H), 6.70 (d, J=8.4 Hz, 1H), 6.63-6.56 (m, 2H), 4.91-4.70 (m, 2H), 4.38-4.24 (m, 2H), 3.88 (s, 2H), 3.18 (q, J=7.2 Hz, 2H), 1.26 (t, J=7.1 Hz, 3H). ¹³C NMR (101 MHz, chloroform-d) δ 146.6, 145.8, 135.7, 128.9, 127.1, 126.7, 125.4, 124.3, 120.4, 115.1, 113.1, 109.5, 81.8 (d, $J_{C-F}$=171 Hz), 67.7 (d, $J_{C-F}$=20 Hz), 38.3, 14.7. ¹⁹F NMR (376 MHz, chloroform-d) δ −91.36 (tt, J=47.6, 28.1 Hz), −100.01. HR-MS (ESI) m/z calculated for ($C_{18}H_{21}FN_2O$) [M+H]⁺ 301.1711, found 301.1706. HPLC purity: 100.0%, retention time 13.12 min. C-18 reversed-phase HPLC (Phenomenex, 10×250 mm), eluent: acetonitrile:H₂O=60:40, flow rate of 3.0 mL/min.

(E)-4-(4-Amino-3-(2-fluoroethoxy)styryl)-N-propylaniline (34)

The brown amorphous compound was purified on a silica flash column and eluted with 20% EtOAc:hexane, yield 0.070 g, (70%). H NMR (400 MHz, chloroform-d) δ 7.31 (d, J=8.6 Hz, 2H), 6.95 (dt, J=4.2, 2.2 Hz, 2H), 6.81 (d, J=2.0 Hz, 2H), 6.70 (d, J=8.4 Hz, 1H), 6.58 (d, J=8.6 Hz, 2H), 4.90-4.80 (m, 1H), 4.77-4.69 (m, 1H), 4.38-4.25 (m, 2H), 3.84 (s, 3H), 3.11 (t, J=7.1 Hz, 2H), 1.65 (h, J=7.3 Hz, 2H), 1.01 (t, J=7.4 Hz, 3H). ¹³C NMR (101 MHz, chloroform-d) δ 147.9, 146.1, 136.0, 129.2, 127.4, 127.1, 125.7, 124.7, 120.7, 115.4, 112.9, 109.8, 82.1 (d, $J_{C-F}$=171 Hz, 1C), 68.0 (d, $J_{C-F}$=20 Hz, 1C), 45.9, 22.8, 11.8. ¹⁹F NMR (376 MHz, chloroform-d) δ −91.36 (tt, J=47.7, 28.2 Hz), −100.01. HR-MS (ESI) m/z calculated for (C19H23FN2O) [M+H]⁺ 315.1867, found 315.1866. HPLC purity: 100.0%, retention time 17.37 min. C-18 reversed-phase HPLC (Phenomenex, 10×250 mm), eluent: acetonitrile:H₂O=60:40, flow rate of 3.0 mL/min.

(E)-4-(4-Amino-3-(2-fluoroethoxy)styryl)-N-isopropylaniline (35)

The yellow amorphous compound was purified on a silica flash column and eluted with 20% EtOAc:hexane, yield 0.10 g (90%). ¹H NMR (400 MHz, chloroform-d) δ 7.30 (d, J=8.7 Hz, 2H), 6.95 (dq, J=4.3, 1.8 Hz, 2H), 6.81 (d, J=1.8 Hz, 2H), 6.69 (d, J=8.4 Hz, 1H), 6.56 (d, J=8.6 Hz, 2H), 4.89-4.81 (m, 1H), 4.77-4.72 (m, 1H), 4.41-4.26 (m, 2H), 3.87 (s, 2H), 3.65 (p, J=6.3 Hz, 1H), 1.22 (d, J=6.3 Hz, 6H). ¹³C NMR (400 MHz, chloroform-d) δ 146.6, 145.8, 135.7, 128.9, 127.1, 126.7, 125.4, 124.3, 120.4, 115.1, 113.1, 109.5, 81.8 (d, $J_{C-F}$=171 Hz,), 67.7 (d, $J_{C-F}$=20 Hz,), 44.0, 22.8. ¹⁹F NMR (376 MHz, chloroform-d) δ −91.36 (tt, J=47.6, 28.1 Hz), −100.01. HRMS (ESI) m/z calculated for (C19H23FN2O) [M+H]⁺ 315.1867, found 315.1867. HPLC purity: 100.0%, retention time 16.22 min. C-18 reversed-phase HPLC (Phenomenex, 10×250 mm), eluent: acetonitrile:H2O=60:40, flow rate of 3.0 mL/min.

(E)-4-(4-Amino-3-(2-fluoroethoxy)styryl)-N-(sec-butyl)aniline (36)

This brown amorphous compound was purified on a silica flash column and eluted with 20% EtOAc:hexane, yield 0.040 g (70%). ¹H NMR (400 MHz, chloroform-d) δ 7.33-7.27 (m, 2H), 6.95 (dt, J=4.4, 2.0 Hz, 2H), 6.80 (d, J=2.5 Hz, 2H), 6.69 (d, J=8.4 Hz, 1H), 6.58-6.53 (m, 2H), 4.88-4.83 (m, 1H), 4.77-4.70 (m, 1H), 4.36-4.32 (m, 1H), 4.30-4.24 (m, 1H), 3.82 (s, 3H), 3.42 (q, J=6.3 Hz, 1H), 1.69-1.57 (m, 1H), 1.53-1.44 (m, 1H), 1.18 (d, J=6.3 Hz, 3H), 0.97 (d, J=7.4 Hz, 3H). ¹³C NMR (101 MHz, chloroform-d) δ 147.1, 146.1, 136.0, 129.3, 127.5, 126.9, 125.8, 124.6, 120.7, 115.4, 113.3, 109.9, 82.1 (d, JC-F=171 Hz), 68.1 (d, JC-F=20 Hz), 50.0, 29.8, 20.4, 10.5. 19F NMR (376 MHz, chloroform-d) δ −91.39 (tt, J=47.5, 27.9 Hz), −100.01. HR-MS (ESI) m/z calculated for (C20H25FN2O) [M+H]⁺ 329.2024, found 329.2020. HPLC purity: 100.0%, retention time 23.37 min. C-18 reversed-phase HPLC (Phenomenex, 10×250 mm), eluent: acetonitrile:H₂O=60:40, flow rate of 3.0 m/min.

(E)-4-(4-Aminostyryl)-2-(2-fluoroethoxy)aniline (37)

This dark red amorphous compound was purified on a silica flash column and eluted with 20% EtOAc:hexane, yield 0.085 g (64%). ¹H NMR (400 MHz, chloroform-d) δ 7.31 (d, J=8.5 Hz, 2H), 6.97 (dq, J=3.2, 1.8 Hz, 2H), 6.84 (s, 2H), 6.71 (d, J=8.5 Hz, 1H), 6.70-6.66 (m 2H), 4.90-4.71 (m 2H), 4.38-4.25 (m 2H), 3.82 (s, 4H). ¹³C NMR (101 MHz, chloroform-d) δ 146.2, 145.8, 136.3, 129.0, 128.7, 127.5, 125.6, 120.9, 115.5, 109.9, 82.2 (d, JC-F=171 Hz), 68.1 (d, JC-F=20 Hz). ¹⁹F NMR (376 MHz, chloroform-d) δ −90.99--91.82 (m), −100.01. HR-MS (ESI) m/z calculated for (C16H17FN2O) [M+H]⁺ 273.1398, found 273.1396. HPLC purity: 100.0%, retention time 7.07 min. C-18 reversed-phase HPLC (Phenomenex, 10×250 mm), eluent: acetonitrile:H₂O=60:40, flow rate of 3.0 mL/min.

tert-Butyl (E)-(4-(4-(2-Fluoroethoxy)-3-nitrostyryl)phenyl)-(methyl)carbamate (38)

Following the general method of Wittig-Horner reaction as described above, compound 38 was synthesized as a yellow sticky solid, which was purified on silica flash column in 15% EtOAc:hexane, yield 0.265 g (75%). ¹H NMR (400 MHz, chloroformd) δ 7.92 (d, J=2.2 Hz, 1H), 7.58 (dd, J=8.7, 2.3 Hz, 1H), 7.42-7.38 (m, 2H), 7.24-7.18 (m, 2H), 7.04 (d, J=8.7 Hz, 1H), 6.94 (d, J=12.2 Hz, 2H), 4.83-4.77 (m, 1H), 4.74-4.67 (m, 1H), 4.40-4.28 (m, 2H), 3.24 (s, 3H), 1.43 (s, 9H). ¹³C NMR (101 MHz, chloroform-d) δ 154.3, 150.6, 143.4, 133.2, 131.4, 131.3, 131.0, 129.1, 128.9, 127.0, 126.4, 125.2, 125.0, 122.78, 115.3, 81.2 (d, JC-F=181 Hz), 69.0 (d, JC-F=21 Hz), 36.9, 28.1. ¹⁹F NMR (376 MHz, chloroform-d) δ −90.96 (tt, J=47.3, 27.1 Hz), −100.01.

(E)-4-(4-(2-Fluoroethoxy)-3-nitrostyryl)-N-methyl-aniline (39)

Following the general method of Boc-deprotection and reduction as described above, compound 39 was synthesized as an off-white amorphous compound, which was purified through precipitation out of EtOAc:hexane (2:3), yield 0.050 g (30%). $^1$H NMR (500 MHz, chloroform-d) δ 7.33 (d, J=8.0 Hz, 2H), 6.90 (s, 1H), 6.85 (s, 1H), 6.80 (s, 1H), 6.76 (s, 1H), 6.67 (s, 1H), 6.59 (d, J=8.1 Hz, 2H), 4.81 (s, 1H), 4.72 (s, 1H), 4.25 (d, J=27.1 Hz, 2H), 3.84 (s, 4H), 2.86 (s, 3H). $^{13}$C NMR (126 MHz, DMSO) δ 149.3, 144.5, 138.0, 131.4, 127.2, 126.3, 125.0, 123.4, 114.9, 112.5, 111.7, 110.9, 82.4 (d, JC-F=166 Hz), 67.8 (d, $J_{C-F}$=19 Hz). 29.6. $^{19}$F NMR (376 MHz, chloroform-d) δ −90.96 (tt, J=47.3, 27.1 Hz), −100.01. HR-MS (ESI) m/z calculated for (C17H19FN2O) [M+H]$^+$ 287.1554, found 287.1552. HPLC purity: >99%, retention time 10.25 min. C-18 reversed-phase HPLC (Phenomenex, 10×250 mm), eluent: acetonitrile:H$_2$O=60:40, flow rate of 3.0 mL/min.

Animal Preparation and Studies

All animal experiments were performed in accordance with guidance protocol approved by the Institutional Animal Care and Use Committee (IACUC) of Case Western Reserve University (Protocol 2013-0016, 2013-0017). The animals were subjected to minimal stress during tail vein injections. The 8 week old wild-type C57BL/6 mice (Jackson Laboratory, Bar Harbor, MN) were used for all of the in vitro and ex vivo tissue staining, and SD rats (Harlan Laboratory, Indianapolis, IN) were used for microPET/CT imaging studies. The rats were fasted overnight prior to imaging, but had access to water. Their diet was then replenished after microPET/CT imaging.

In Vitro Tissue Staining and Assay of Fluorescent Intensity

Wild-type mice (20-22 g, 8 weeks old) were deeply anesthetized and perfused transcardially with precooled saline (4° C., 10 mL/min for 1 min followed by 7 mL/min for 6 min) followed by fixation with precooled 4% PFA in PBS (4° C., 10 mL/min for 1 min followed by 7 mL/min for 6 min). Brain tissues were then removed, postfixed by immersion in 4% PFA overnight, dehydrated in 10%, 20%, and 30% sucrose solution, embedded in a freezing compound (OCT, Fisher Scientific, Suwanee, GA), and sectioned at 20 μm with a cryostat (Thermo HM525, Thermo Fisher Scientific Inc., Chicago, IL, USA). Brain sections were collected from AP (1.0) to AP (−0.1) and in 12 sections were mounted in order on the bottom of 12 superfrost slides (Fisher Scientific) with one section on each slide. Sections 13-24 were mounted in order on the middle of each slide, and sections 25-36 were mounted in order on the top of each slide. Sections were then incubated with tested compounds (1 mM, 5% DMSO in 1×PBS (pH 7.0), 6 sections per compound) for 25 min at room temperature in the dark. Excess compounds were washed by briefly rinsing the slides in PBS (1×) and coverslipped with fluoromount-G mounting media (Vector Laboratories, Burlingame, CA). Sections were then examined under a microscope (Leica DM4000B, Leica Microsystem Inc., Buffalo Grove, IL, USA) equipped for fluorescence (DFC7000T), and images of the stained mouse whole brain sections were acquired with the same exposure time. ImageJ software was then used to quantify pixel intensity values on 6 sections of each tested compound. A ROI was selected on the genus of the corpus callosum (gcc, white matter), and the same size ROI was applied on the midline between gcc and the edge of the section (see FIG. 2A), which is considered as gray matter. Images were analyzed by two experienced individuals. The FIR of white matter to gray matter were then calculated.

Ex Vivo Imaging

Wild-type mice were administered with the newly synthesized compounds (40 mg/kg) via tail vein injection, and 30 min later, the mice were perfused transcardially with saline followed by 4% PFA in PBS. Brain tissues were then removed, postfixed by immersion in 4% PFA overnight, dehydrated in 30% sucrose solution, cryostat sectioned at 100 μm, and mounted on superfrost slides, and images were acquired directly using a Leica fluorescent microscope.

Radiosynthesis

No carrier-added (n.c.a.) [$^{18}$F] fluoride was produced by a cyclotron (Eclipse High Production, Siemens) via the nuclear reaction $^{18}$O (p,n) $^{18}$F. At the EOB, the activity of aqueous [$^{18}$F] fluoride (50-100 mCi) was transferred to the GE Tracerlab Fxn synthesizer with high helium pressure. After delivery, the radioactive solution was passed through a Sep-Pak light QMA cartridge (Waters, WAT023525, 130 mg, 37-55 μm, preconditioned with 5 mL of water followed by 10 mL of air in syringe) and was eluted with K$_2$CO$_3$ solution (6 mg, 0.043 mmol, in 0.6 mL water) followed by K$_{222}$ solution (12 mg, 0.032 mmol, in 1 mL acetonitrile). The solvent was evaporated under a steam of helium at 85° C. for 5 min, and the residue was vacuumed at 55° C. for another 3 min to get the anhydrous K222/[$^{18}$F] complex. A solution of the tosylated precursors (3-5 mg, 0.0062-0.011 mmol, in 0.8 mL acetonitrile) was added to the above dried complex, and the mixture was heated at 110° C. for 10 min. Ethyl acetate (3 mL) and hexane (2 mL) were added to the reaction vessel, and the mixture was passed through a preconditioned Sep-Pak silica cartridge (Waters, WAT 020520, 690 mg, 55-105 μm, preconditioned with 5 mL of ether). The solvent was removed under a steam of helium at 70° C., and the residue was added to a tin chloride solution (30 mg, 0.16 mmol, in 1 mL ethanol and 0.5 mL HCl (1 M). The resulting mixture was heated at 115° C. for 10-20 min. A NaOH solution (0.8 mL, 1 M) and water (15 mL) were then added, and the resulting mixture was passed through a preconditioned Sep-Pak C-18 cartridge (Waters, WAT020515, 360 mg, 55-105 μm, preconditioned with 5 mL of ethanol followed by 10 mL of water, then dried by 10 mL of air in a syringe). The cartridge was washed with another 20 mL of water, and the crude products were eluted with 1 mL acetonitrile which was further purified by semipreparative HPLC (Phenomenex C-18, 10×250 mm, acetonitrile:H$_2$O=60:40, flow rate of 5 mL/min, tR=6-14 min). The radioactive fraction containing the desired products was collected, diluted with water, loaded onto a Sep-Pak C-18 cartridge, and eluted with 1 mL ethanol. After evaporation, the residue was redissolved in 5% ethanol in saline solution and filtered (0.22 μm) into a sterile injection bottle for animal use. RCP and specific activity (SA) were determined by analytical HPLC (Phenomenex C-18, 4.6×250 mm, acetonitrile:H$_2$O=65:35, flow rate of 1 mL/min, tR=6-10 min). SA was calculated by area of the UV peak of purified F-18 compound and titrated with the standard curve of the nonradioactive reference compound of known concentration.

MicroPET/CT Image Acquisition and Analysis

MicroPET/CT imaging was performed using a Siemens Inveon microPET/CT scanner in the Case Center for Imaging Research. For better anatomic localization, CT coregistration was applied. Before microPET imaging, CT scout views were taken to ensure the brain tissues were placed in the coscan field of view (FOV) where the highest image resolution and sensitivity are achieved. Under anesthesia, radiotracers (1-2 mCi) were administered via tail vein injection and immediately followed by a dynamic PET acquisition up to 60 min. Once microPET acquisition was done, the rat was moved into the CT field and a two-bed CT scan was performed. A two-dimensional ordered subset expectation maximization (OSEM) algorithm was used for image reconstruction using CT for the attenuation correction. For quantitative analysis, the resultant PET images were registered to the CT images which enabled us to accurately define the ROI and quantify the radioactivity concentrations. In this study, the whole brain of rat was used as ROI, and the radioactivity concentrations were determined in terms of SUV.

In Situ Autoradiography

Ex vivo Wild-type mice were euthanized at 10 min post i.v. injection of [$^{18}$F]32 (3.0 mCi). The brains were rapidly removed, placed in optimal cutting temperature (OCT) embedding medium and frozen at −20° C. After reaching equilibrium at this temperature, the brains were coronally cryostat sectioned at 60 μm on a cryostat and mounted on superfrost slides. After drying by air at room temperature, the slides were put in a cassette and exposed to film to obtain images.

Ex Vivo Block

For ex vivo blocking studies, mice were pretreated with CIC, a compound which has proved to bind to myelin with high affinity and specificity (i.v. 160 mg/kg) 3 h before injection of [$^{18}$F]32 (3.0 mCi). Mice were then euthanized, and brains were removed and sectioned. After drying by air, the slides were put in a cassette and exposed to film to obtain images.

Biostability of [$^{18}$F]32 in Wild-Type Mice

The in vivo biostability of [$^{18}$F]32 in plasma was analyzed using radio-HPLC. Briefly, mice (n=3) were sacrificed at 5, 30, and 60 min postinjection of [18F]32 (0.8-1.0 mCi) through tail vein. Blood was collected into VACUETTE blood collection tubes which were precoated with K3EDTA (containing 4.0 mg of K3EDTA, Greiner Bio One, Germany). The samples were centrifuged at 3000 rpm for 5 min at 4° C. to separate plasma. The supernatant plasma samples were mixed with ice-cold methanol and centrifuged again at 10,000 rpm for 3 min to further remove proteins and other biological matrix. The supernatant was then analyzed by radio-HPLC using acetonitrile/water (60:40, v/v) as mobile phase at a flow rate of 1.0 mL/min. The percentage of parent compound was then calculated.

Results

Chemistry

The design of the fluorinated radioligands is based on the structure of MeDAS, a lead myelin-specific radioligand that we previously developed for PET imaging of myelination. Structure-activity relationship studies suggested that fluorine could be introduced through alkylation of the amino groups, which are responsible for binding to myelin. Once various fluorinated alkyl groups are introduced to MeDAS, the derivatives produced may have different lipophilicity and permeability across the blood-brain barrier (BBB). Thus, the newly synthesized fluorinated analogs, even though they share the same pharmacophore as MeDAS, may display distinctly different physicochemical and biological properties. Thus, we conducted a systematic evaluation of the in vitro and in vivo properties of binding to myelin.

Our previous structure-activity relationship studies suggested that the two amino groups can be modified but cannot be replaced, as they both are responsible for myelin binding. Thus, we introduced fluorine to MeDAS via an aliphatic ether side chain in the beta-position to the amino group. Introduction of fluorine often reduces the lipophilicity of compounds. We thus synthesized a series of fluorinated MeDAS analogs by alkylating the other amino group opposite to the fluorinated alkyl amino group.

The lipophilicity of these compounds was calculated using ALOGPS 2.1 program (Virtual Computational Chemistry Laboratory). As shown in Table 1, the calculated lipophilicity (cLogP) of these newly synthesized compounds ranges from 2.7 to 5.4. Such a range provides a good spectrum of lipophilicity for us to navigate the in vitro and in vivo binding properties.

TABLE 1

| Entry | Structure | clogP |
| --- | --- | --- |
| MeDAS | 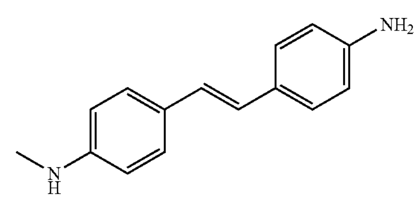 [SMILES: CNc1ccc(/C=C/c2ccc(N)cc2)cc1] | 3.39 |
| 25 | 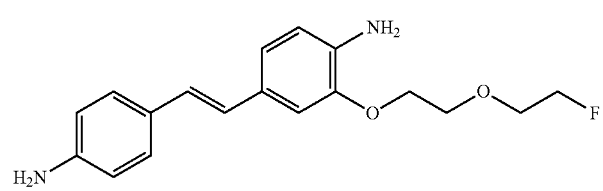 [SMILES: Nc1ccc(/C=C/c2ccc(N)c(OCCOCCF)c2)cc1] | 2.78 |
| 32 | 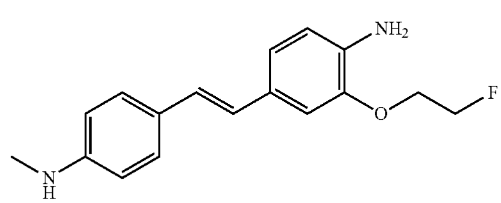 [SMILES: CNc1ccc(/C=C/c2ccc(N)c(OCCF)c2)cc1] | 3.65 |

TABLE 1-continued
| Entry | Structure | clogP |
|---|---|---|
| 33 | 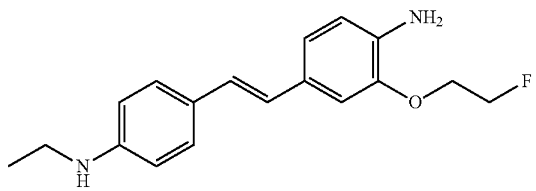 [SMILES: CCNc1ccc(/C=C/c2ccc(N)c(OCCF)c2)cc1] | 4.23 |
| 34 | 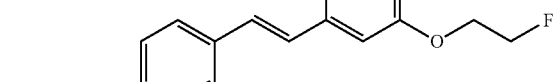 | 4.68 |
| 35 | 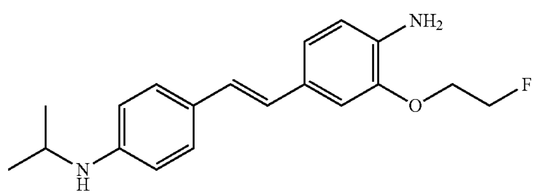 [SMILES: CC(C)Nc1ccc(/C=C/c2ccc(N)c(OCCF)c2)cc1] | 4.48 |
| 36 | 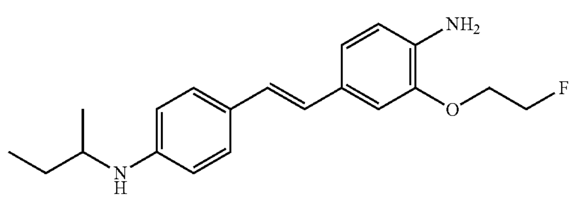 [SMILES: CCC(C)Nc1ccc(/C=C/c2ccc(N)c(OCCF)c2)cc1] | 5.27 |
| 37 | 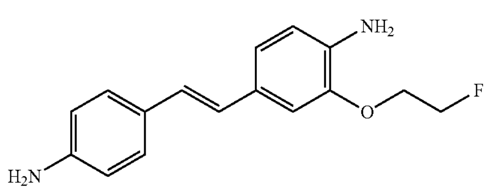 [SMILES: Nc1ccc(/C=C/c2ccc(N)c(OCCF)c2)cc1] | 2.75 |
| 39 | 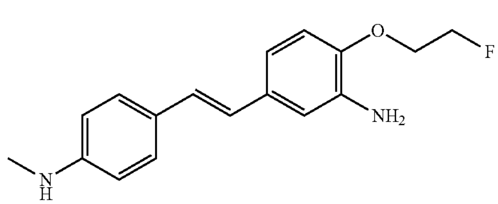 [SMILES: CNc1ccc(/C=C/c2ccc(OCCF)c(N)c2)cc1] | 3.63 |

As shown in Scheme 1, various tosylated nitrobenzaldehydes (3, 4, 6) and fluorinated nitrobenzaldehydes (5, 7) were first prepared from 3-hydroxy-4-nitrobenzaldehyde (1) and 4-hydroxy-3-nitrobenzaldehdye (2) in 50-90% yield.

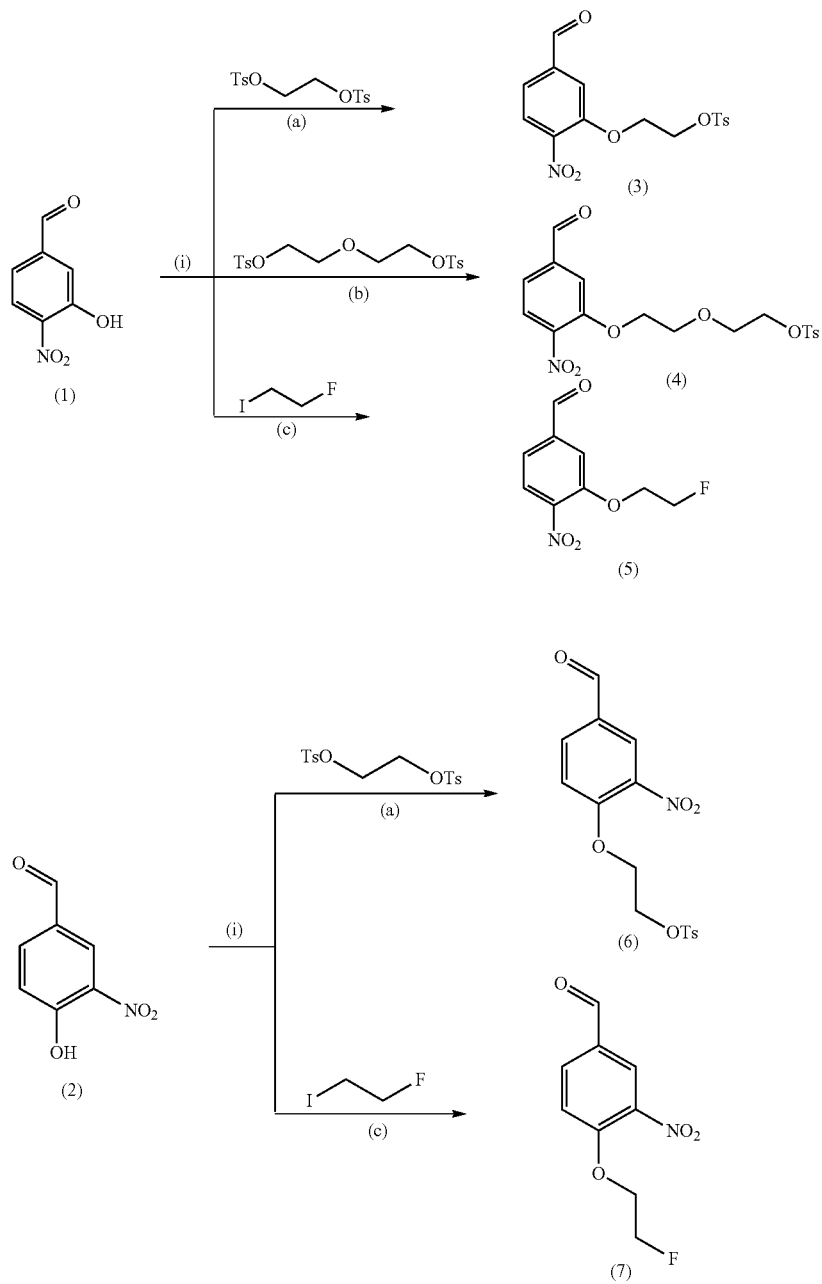

Scheme 1. Synthesis of Tosylated and Fluorinated Nitrobenzaldehyde Derivative (3-7)[a]

[a]Reagents and conditions:
(i) $K_2CO_3$, DMF, 80° C., 6 h, yield 50-90%

For the synthesis of fluorinated MeDAS analogs except compound 25, we started with p-aminobenzyldiethyl phosphonate. As shown in Scheme 2, the amino group was first protected with Boc to generate compound 9 in 95% yield, which was subsequently alkylated with different alkyl iodides to obtain compounds 10-14 in 20 to 80% yield.

Scheme 2. Synthesis of Alkylated tert-Butyl (4-((diethoxyphosphoryl)methyl)phenyl)carbamate (10-14)[a]

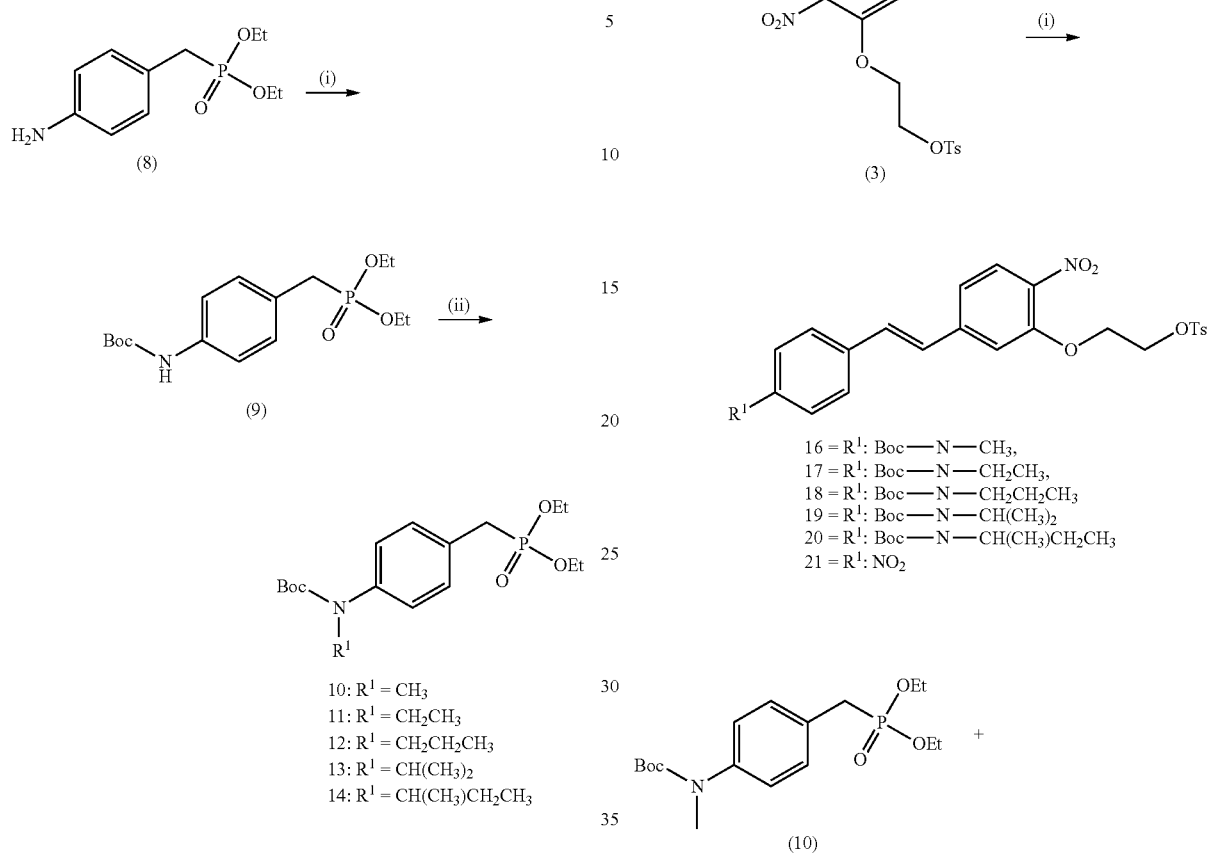

10: R[1] = CH$_3$
11: R[1] = CH$_2$CH$_3$
12: R[1] = CH$_2$CH$_2$CH$_3$
13: R[1] = CH(CH$_3$)$_2$
14: R[1] = CH(CH$_3$)CH$_2$CH$_3$

[a]Reagents and conditions:
(i) (Boc)$_2$O, THF:H$_2$O (3:1), 20° C., 48 h, yield 95%;
(ii) NaH (95%), R1I, anhydrous THF, 0-20° C., 12 h, yield 75 to 20%.

The Boc-protected-N-alkylated diethyl benzylphosphonate and diethyl (4-nitrobenzyl)phosphonate (10-15) were coupled with tosylated nitrobenzaldehydes (3, 4, 6) to produce the radiolabeling precursors (16-23) through the Homer-Wadsworth-Emmons reaction (Schemes 3 and 4) in 40 to 80% yield. These precursors (16-23) were used for the radiosynthesis of F-18-labeled MeDAS analogs.

Scheme 3. Synthesis of Tosylated Precursor of MeDAS Analogue for the [18F]-Labeling (16-22)[a]

10 = R[1]: Boc—N—CH$_3$,
11 = R[1]: Boc—N—CH$_2$CH$_3$,
12 = R[1]: Boc—N—CH$_2$CH$_2$CH$_3$
13 = R[1]: Boc—N—CH(CH$_3$)$_2$
14 = R[1]: Boc—N—CH(CH$_3$)CH$_2$CH$_3$
15 = R[1]: NO$_2$

16 = R[1]: Boc—N—CH$_3$,
17 = R[1]: Boc—N—CH$_2$CH$_3$,
18 = R[1]: Boc—N—CH$_2$CH$_2$CH$_3$
19 = R[1]: Boc—N—CH(CH$_3$)$_2$
20 = R[1]: Boc—N—CH(CH$_3$)CH$_2$CH$_3$
21 = R[1]: NO$_2$

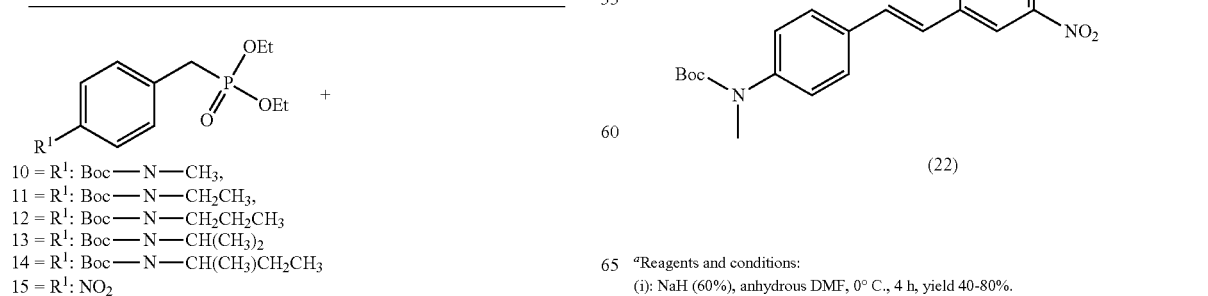

[a]Reagents and conditions:
(i): NaH (60%), anhydrous DMF, 0° C., 4 h, yield 40-80%.

Scheme 4. Synthesis of Compound 25[a]

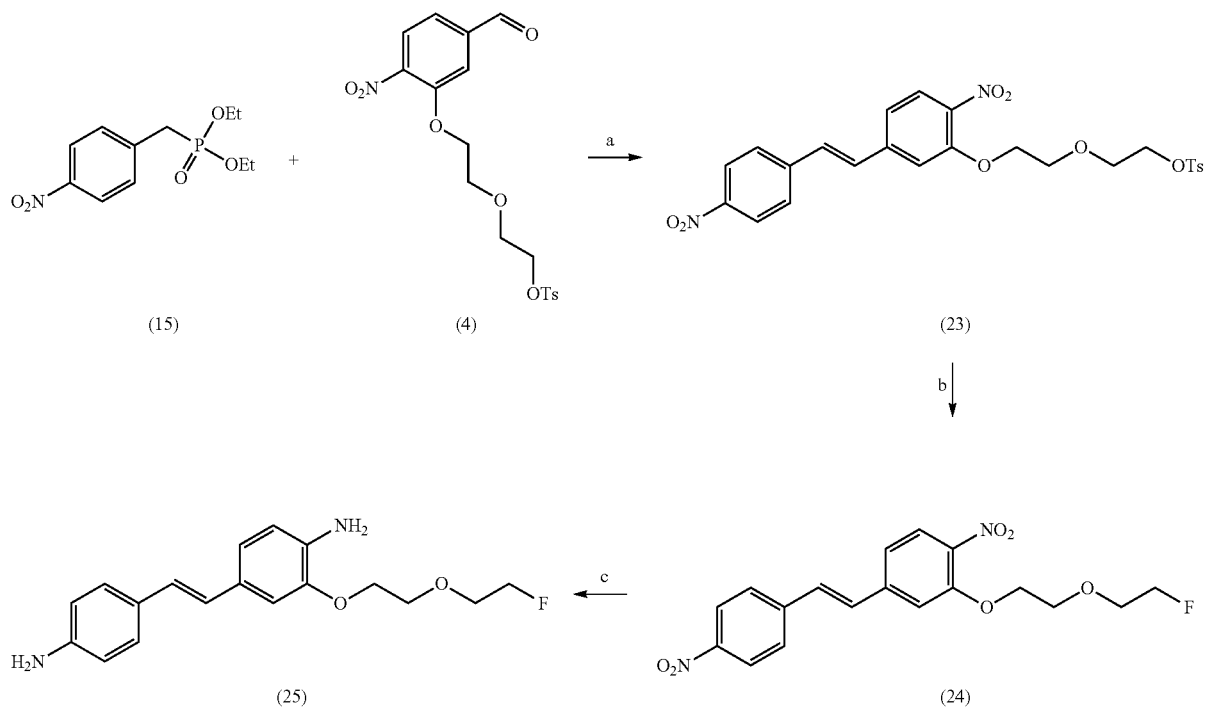

[a]Reagents and conditions:
(a) NaH (60%), DMF, 0° C., 2 h, yield 80%.
(b) $K_{222}$, CsF, MeCN, 80° C., 4 h, yield 84%.
(c) $SnCl_2$, EtOAc:EtOH (3:2) 80° C., 6 h, yield 47%.

For the synthesis of compound 25, the tosylated compound 23 was subjected to a nucleophilic substitution to generate compound 24 in 80% yield followed by reduction of the nitro group to give the final cold standard compound 25 in 50% yield (Scheme 4).

For the synthesis of the remainder of fluorinated compounds 32-37 and 39, fluorinated nitrobenzaldehydes (5, 7) and compounds 10-15 were coupled to produce intermediates 26-31 and 38 in 40-60% yield (Scheme 5). This was followed by a one-pot reaction using $SnCl_2$ in ethanol and ethyl acetate, which allowed for simultaneous deprotection of the Boc group and reduction of the nitro group to the amino group of compounds 26-31 and 38 in 30-90% yield to generate final compounds 32-37 and 39 that can be used as standards for radiochemistry synthesis as well as for biological evaluations.

Scheme 5. Synthesis of Fluorinated MeDAS Analogs (32-39)[a]

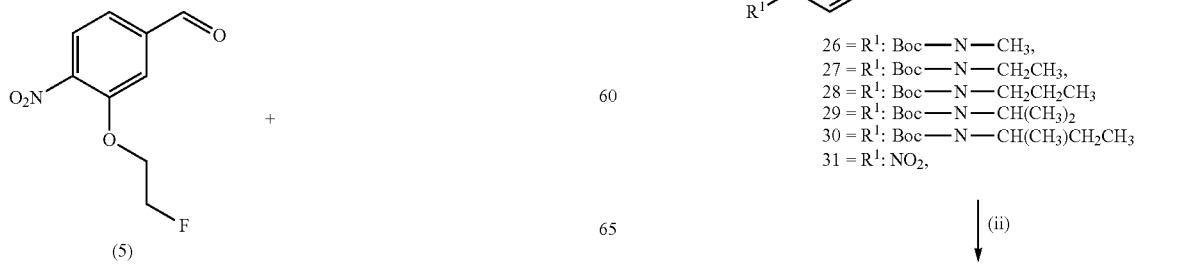

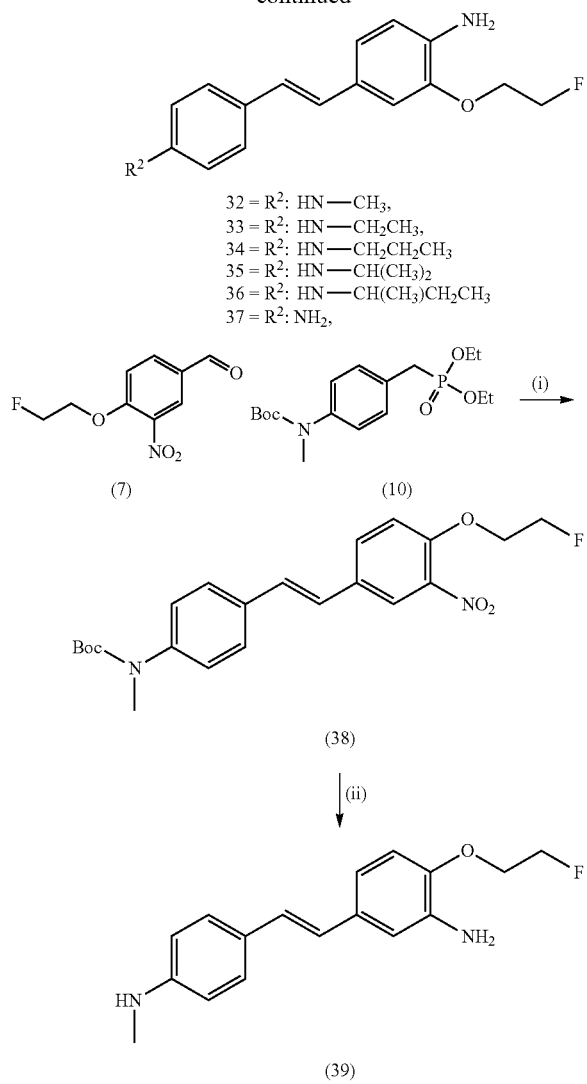
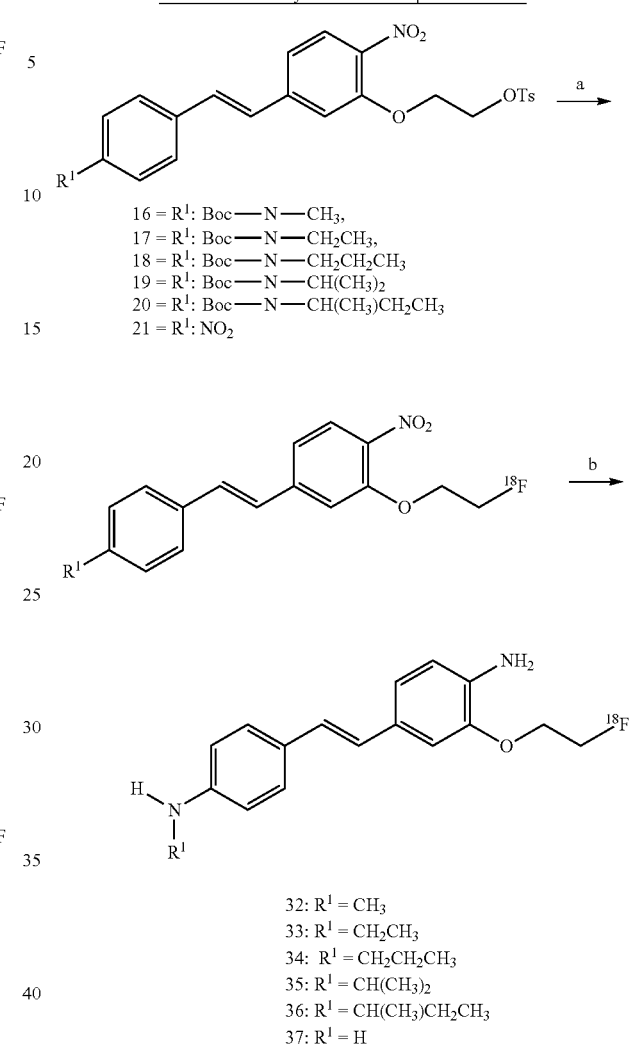
Scheme 6. Radiosynthesis of Compounds 32-37[a]
32: $R^1$ = $CH_3$
33: $R^1$ = $CH_2CH_3$
34: $R^1$ = $CH_2CH_2CH_3$
35: $R^1$ = $CH(CH_3)_2$
36: $R^1$ = $CH(CH_3)CH_2CH_3$
37: $R^1$ = H
[a]Reagents and condition:
(i) NaH (60%), anhydrous DMF, Ar, 0° C., 4 h, yield 40-80%;
(ii) $SnCl_2$, EtOAc:EtOH (3:2), 80° C., 6 h, yield 30-70%.
[a]Reagents and conditions:
(a) $^{18}F^-$, $K_2CO_3$, $K_{222}$, MeCN, 115° C., 10 min, 60-80%.
(b) $SnCl_2$, EtOH, HCl, 120° C., 10-20 min, 30-60%.
Scheme 7. Radiosynthesis of Compound 25
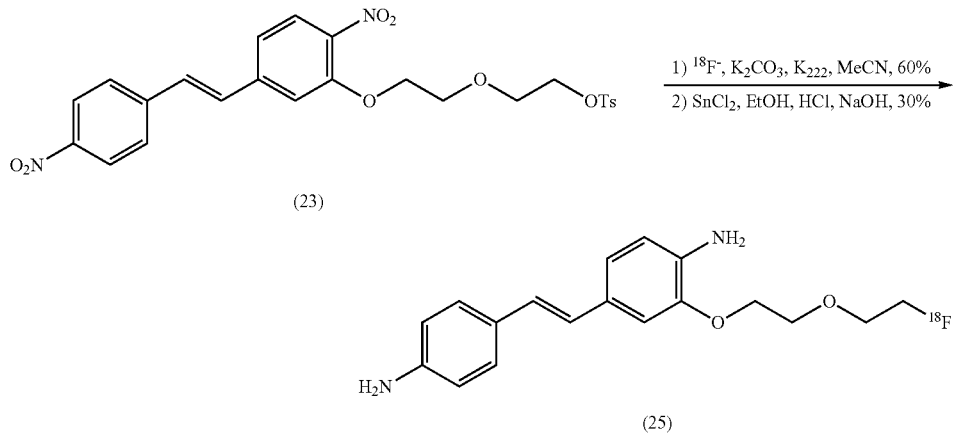

Scheme 8. Radiosynthesis of Compound 39

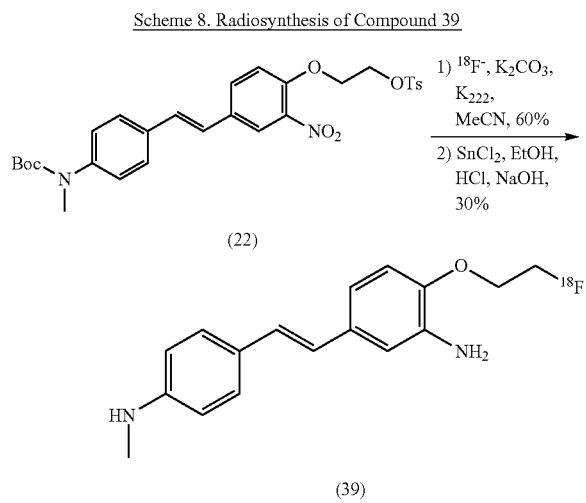

Similar to MeDAS, all of the newly synthesized fluorinated analogs are fluorescent. The excitation/emission spectra were acquired in acetonitrile for comparison as shown in FIG. 1. The excitation wavelengths of these compounds were measured to be 390±10 nm, and the emission wavelengths were measured to be 420±10 nm. Such wavelengths are in an ideal range to conduct fluorescent tissue staining which allows examination of the preliminary binding specificity for myelin, either in vitro or in situ.

Figure 2A:
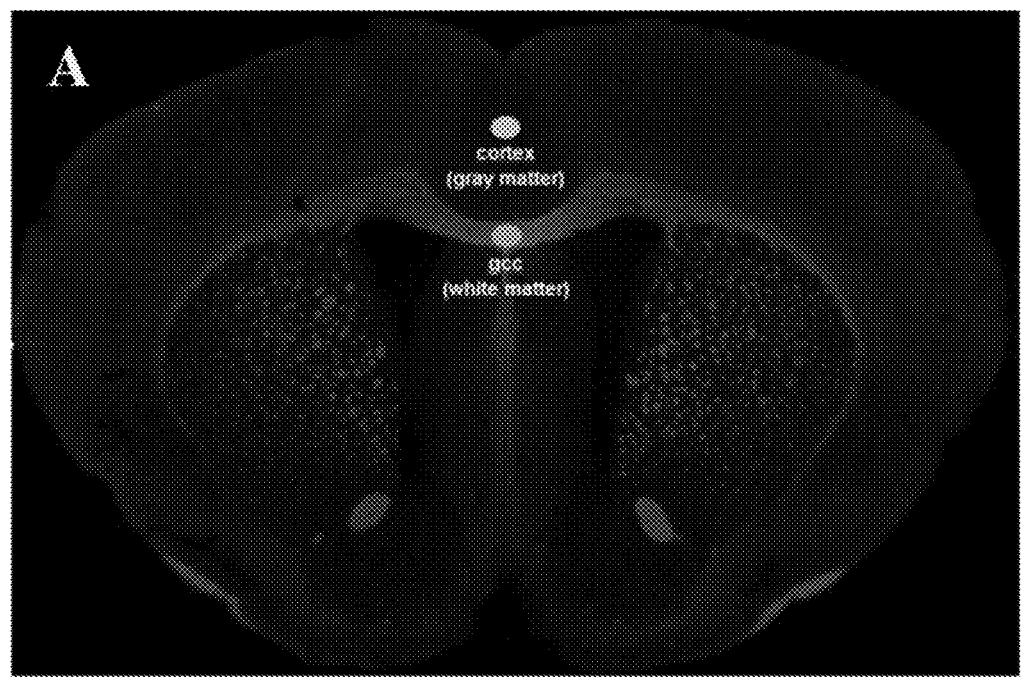
FIGS. 2(A-B) illustrate an image and graph showing FIR in white matter vs gray matter. (A) Representative in vitro tissue staining showing ROI used for calculation for FIR between white matter and gray matter. (B) ImageJ was used to calculate FIR of each target compound showing compounds 32 and 35 with FIR>2.
Figure 2B:
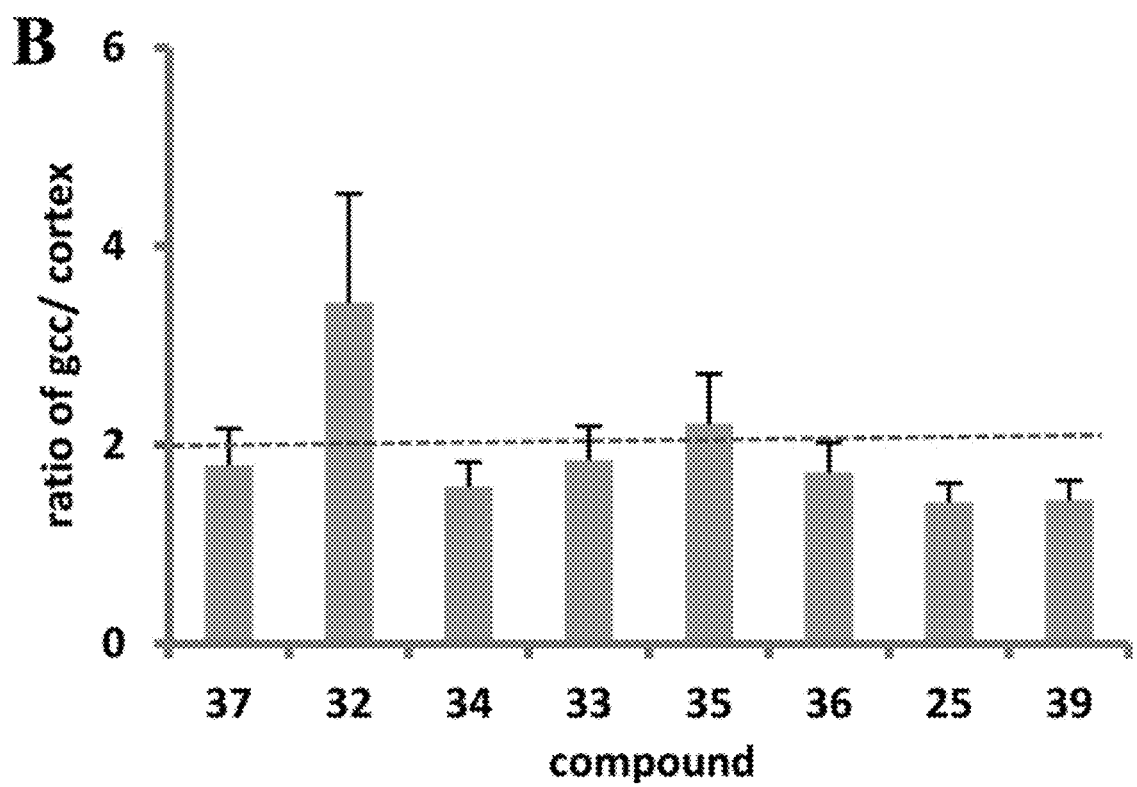

In vitro Staining and Assay of the Fluorescent Intensity. In vitro fluorescent tissue staining provides a convenient way to screen binding specificity of the newly synthesized compounds for myelin. Myelin sheaths are distributed more dominantly in the white matter than in the gray matter. Thus, the fluorescent intensity is expected to be consistent with the pattern of myelin distribution in the brain. As expected, in vitro tissue staining of mouse brain sections showed that all target compounds (25, 32-37, and 39) selectively stained myelinated regions such as corpus callosum and striatum. In order to compare the binding feature for myelin by in vitro histological staining of mouse brain tissue sections, all compounds were tested at same time, the concentration of all the tested staining solution was 1 mM, and sections were imaged under the same exposure time after being incubated with the staining solution for 25 min. Next, we selected a representative region in the genus of the corpus callosum (gcc) and a representative region in the subcortical gray matter (cortex) and calculated the fluorescent intensity ratio (FIR) between both regions (FIG. 2A). This allowed us to preliminarily compare the binding specificity for myelin. As shown in FIG. 2B, the newly synthesized compounds can be divided into two groups, with two of the compounds (32 and 35) showing a FIR>2 and the rest of them <2. The higher FIR indicates a higher degree of specific binding. This study suggested that compounds 32 and 35 be the lead candidates for further evaluation.

Ex Vivo Imaging

Figure 3A:
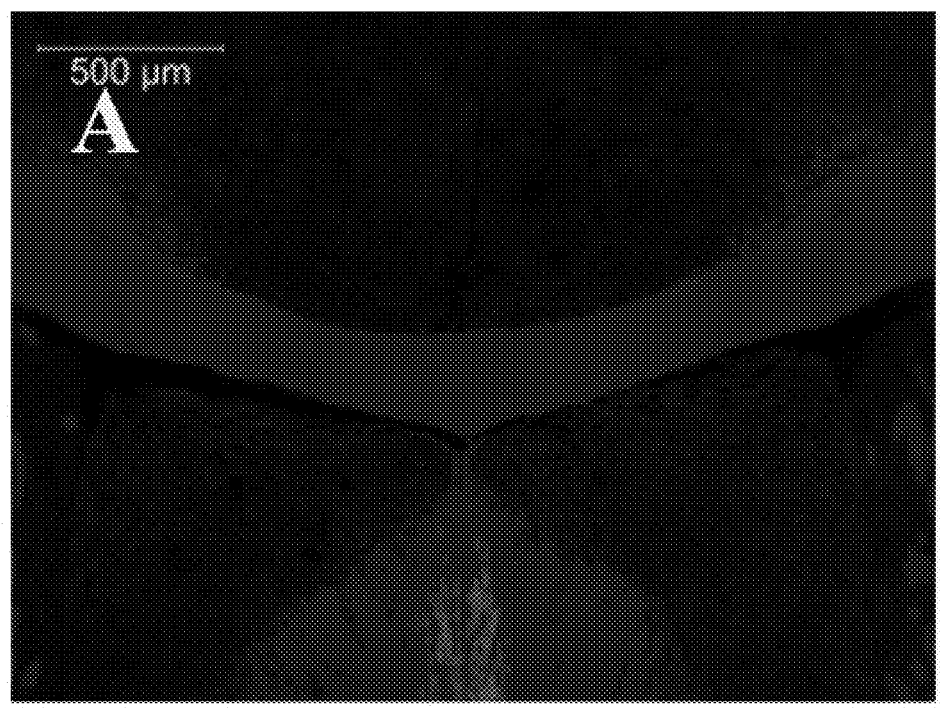
FIGS. 3(A-D) illustrate ex vivo images of corpus callosum and the whole brain with compounds (A and B) 32 and (C and D) 35.

The newly synthesized fluorescent compounds are also suitable for in situ tissue staining through direct tail vein injection. This study allowed us to determine both brain permeability as well as in vivo binding specificity. Thus, ex vivo imaging was performed following in vitro tissue staining. At a dose of 40 mg/kg, each tested compound was administered to mice through tail vein injection. Use of high concentration is needed to enable fluorescence visualization ex vivo. As shown in FIG. 3, the two lead compounds readily enter the brain and specifically bind to myelin tracts present in the white matter regions such as the corpus callosum and striatum. In fact, all the newly synthesized compounds can penetrate the BBB and selectively localize in the white matter region. Such in situ staining, however, is only a qualitative and insensitive measure to determine brain permeability. The injected amounts are in the range of 40 mg/kg, which is at least 3 orders of magnitude greater than in vivo PET imaging.

Radiosynthesis

Encouraged by the above results, we then evaluated the in vivo pharmacokinetic profiles of the newly synthesized compounds labeled with positron emitting fluorine-18. The radiosynthesis was achieved through nucleophilic substitution of a tosylate group, as shown in Schemes 6, 7, and 8, with fluorine-18 generated by an onsite cyclotron followed by a reduction and/or acidic hydrolysis of the Boc protection group. In this study, the tosylated precursor was employed in a three-step radiosynthesis starting with a nucleophilic substitution with $^{18}F$ in the presence of $K_2CO_3$ and Kryptofix ($K_{222}$) in MeCN at 115° C. for 10 min. After evaporation of MeCN, more than 91±7% (n=15) of the activity was retained in the reaction vessel. The fluorinated intermediate was simply purified by passing through a silica Sep-Pak to remove unreacted free fluorine-18. The fluorinated intermediate (60-80%) was then reduced by $SnCl_2$ in hydrochloric acid and ethanol at 120° C. for 10 min to yield the primary amine (compound 25 and 37). At this step, it was necessary to extend the reaction time if the acidic hydrolysis of the Boc protecting group is needed (compound 32-36 and 39). After cooling to room temperature, the reactant was neutralized to pH 8-9 by addition of NaOH (1.0 M, 0.8 mL) and was further purified by semipreparative HPLC to yield the final products with modest yields (for the three-step procedure) ranging from 30-60% (decay corrected to the end of bombardment (EOB)) within 120-130 min.

The identities of the products were confirmed using HPLC by co-injection with each cold standard compound. Radio-chemical purity (RCP) of final products was over 98% determined by analytical radio-HPLC. The specific activity at the end of synthesis was in a range of 0.55-2.5 Ci/μmol. All the [$^{18}F$]$^-$ labeled compounds were stable after being allowed to stand at room temperature for 4 h or diluted with saline. The radiochemical purity of both the original and diluted aqueous solutions was >95% determined by analytical HPLC.

Quantitative microPET/CT Imaging

Figure 4A:
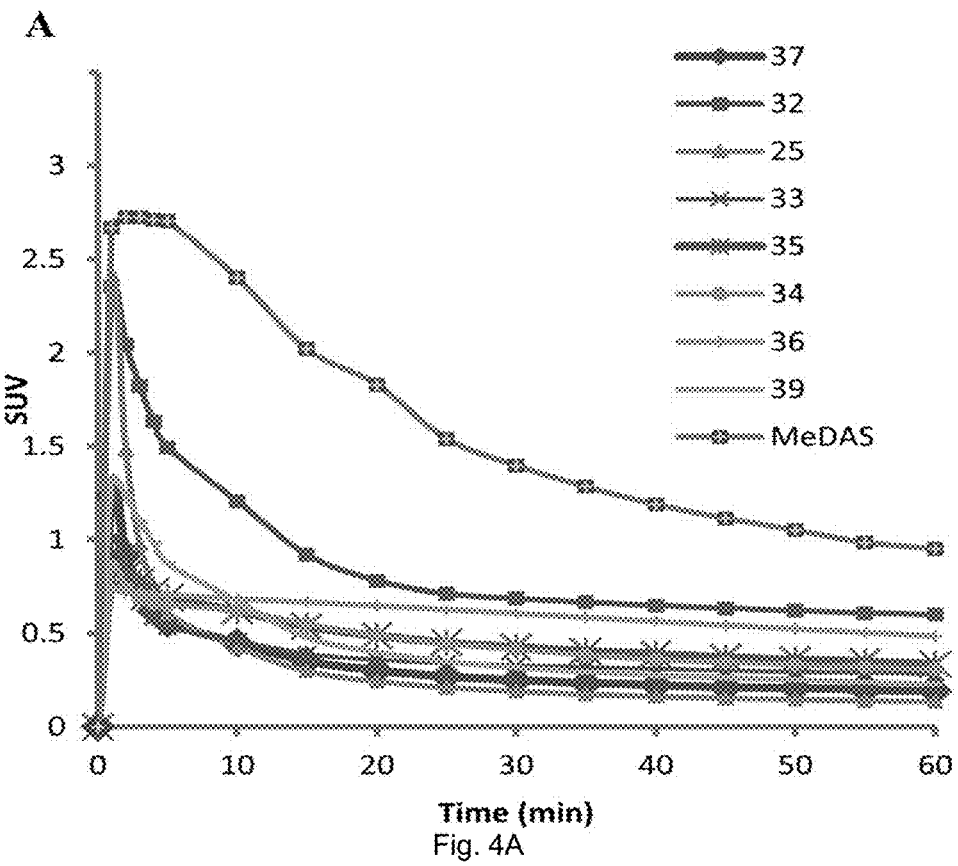
FIGS. 4(A-B) illustrate plots and a graph showing (A) Average radioactivity concentration of target compounds in the whole brain in terms of SUV as a function of time. (B) Average SUV of late time points (40-60 min).
Figure 4B:
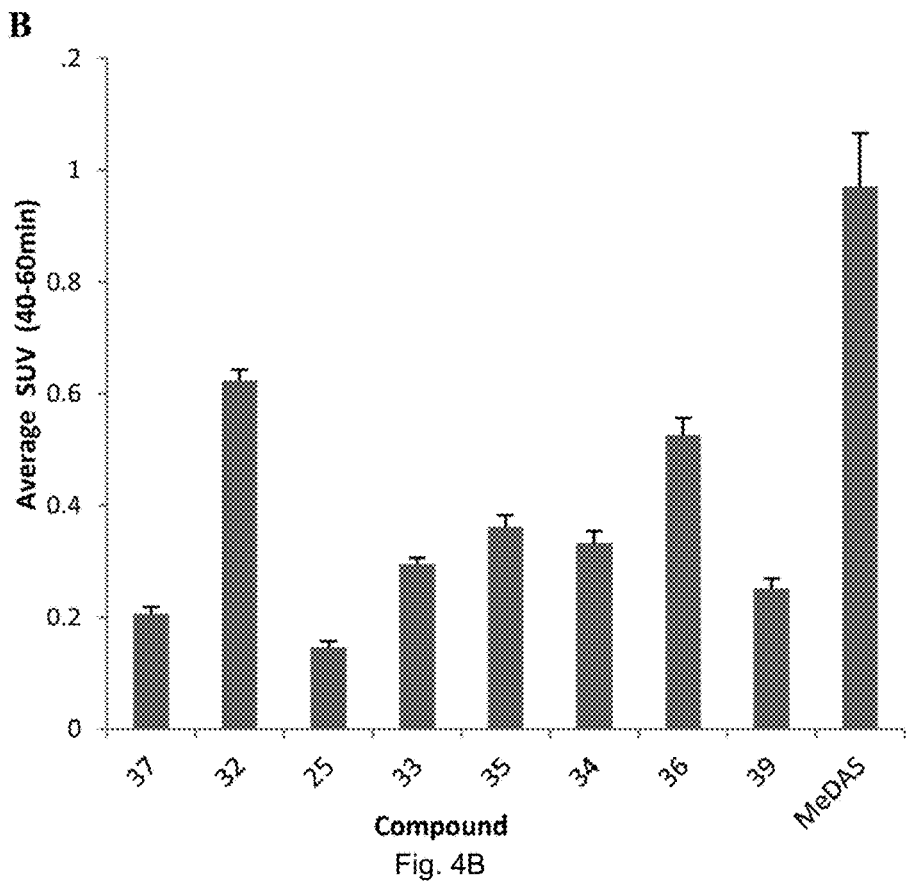

Following radio-labeling, the brain entry, retention, and clearance of each compound was determined by microPET/CT imaging in Sprague-Dawley (SD) rats. For quantitative analysis, the resultant microPET images were registered to the CT images, which allowed us to accurately define the region of interest (ROI) and quantify the radioactivity concentrations of each compound. The radioactivity concentrations were determined in terms of standardized uptake values (SUV). As shown in FIG. 4A, all of the compounds entered the brain at early time points with various retention and clearance rates at later time points. Similar to [$^{11}C$] MeDAS, the radioactivity concentration rapidly reached a peak within 5 min and then decreased to reach a plateau at 40-60 min. Most of the F-18-labeled compounds exhibited a relatively low retention and fast clearance, which suggested either slow interaction with myelin membrane or low binding potency. The two lead candidates (compounds 32 and 35) that were identified through fluorescent tissue staining showed distinct in vivo pharmaco-kinetics. [$^{18}F$]32 showed the highest brain uptake at early time points and highest retention at later time points with a clearance rate of 2.62, which suggests a low nonspecific binding. In comparison [$^{18}$F]35 showed relatively high retention at later time points, but the brain uptake was significantly lower than [$^{18}$F]32 with a clearance rate of 0.70, which suggests a relatively high nonspecific binding. As shown in FIG. 4B, although [$^{18}$F]36 displayed the second highest retention at later time points, the initial brain uptake was the lowest compared with the rest of the compounds with a clearance rate of 0.30, which suggests poor brain permeability or high nonspecific binding. In addition, due to the highest cLogP value (5.27), [$^{18}$F]36 displayed very slow washout from the whole brain, indicating it is hardly cleared from the brain once penetrating into the BBB. As shown in FIG. 4A, both [$^{11}$C]MeDAS and [$^{18}$F]32 showed similar brain entry at early time points. Yet, the clearance of [$^{18}$F]32 was found to be faster than that of [$^{11}$C]MeDAS. Overall, among the radiolabeled analogs, [$^{18}$F]32 clearly stands out as the best lead candidate for in vivo imaging of myelin, which is consistent with in vitro FIR data. Representative microPET/CT images of [$^{18}$F]32 are shown in FIG. 5.

In Situ Autoradiography

To validate the PET results and confirm that the PET signals were indeed from specific binding to myelin, we conducted ex vivo autoradiography. Auto-radiography allowed us to examine microscopic localization of the radiolabeled compounds after brain entry. After quantitative analysis of microPET/CT studies, [$^{18}$F]32 was selected to perform ex vivo film autoradiography, which allowed us to further examine brain permeability and specific binding of the compound. Thus, we conducted ex vivo autoradiography studies in the mouse brain by administering [$^{18}$F]32 through tail vein injections. As shown in FIG. 6A, [$^{18}$F]32 is localized predominantly in the white matter region which is consistent with the pattern of myelin distribution. A relatively distinct labeling of the corpus callosum, an area known to have a high density of myelinated sheaths, was observed after mouse brain tissue sections (coronal) were exposed to film for 10 min. The autoradiographic visualization was consistent with histological staining of myelinated regions (FIG. 6C). To demonstrate that radioactivity in the autoradiography was from specific binding to myelin, we pretreated rats with nonlabeled CIC, a myelin-specific agent that we previously developed. As shown in FIG. 6B, pretreatment of CIC significantly reduces the contrast of radioactivity in gcc vs cortex. Since CIC itself is also fluorescent, a distinct staining of CIC can be examined on the same section when checked under a fluorescence microscope (FIG. 6D). When the film was analyzed using ImageJ, the optical density ratio (ODR) of gcc to cortex was employed to determine the radiographic staining ratio between white matter and gray matter. Statistical analysis of ODR on the film showed there is a significant difference ($p<0.05$) between control (3.73±0.31) and ex vivo block studies (1.91±0.04) (FIG. 6E). Such an ex vivo competition study suggests that [$^{18}$F]32 readily enters the brain and specifically binds to myelin sheaths.

Biostability of [$^{18}$F]32

Because [$^{18}$F]32 showed the highest brain uptake and fastest washout in normal mice, we further evaluated the in vivo biostability of [$^{18}$F]32 in plasma. After injection of [$^{18}$F]32, the plasma samples were harvested and analyzed by radio-HPLC. To the plasma samples were first added ice-cold methanol to precipitate proteins and other biohydrophilic matrix components. The mixtures were centrifuged at 10,000 rpm for 5 min. The supernanant were then separated and loaded onto radio-HPLC for assessment (Phenomenex C-18, 4.6×250 mm, acetonitrile:$H_2O$=65:35, flow rate of 1 mL/min). Similar to [$^{11}$C]PIB and [$^{18}$F]-Flutemetamol, [$^{18}$F after tail vein injection. The percentage of parent [$^{18}$F]32 in plasma was determined to be 78.14±9.15% at 5 min after injection. The percentage of parent [$^{18}$F]32 decreased to 53.12±7.31% and 32.45±5.80% at 30 and 60 min postinjection. All the metabolites found in the plasma were hydrophilic with retention time close to void volume, which are incapable of penetrating the BBB.

Example 2

We designed and synthesized a novel series of fluorinated and fluorescent compounds using click chemistry through Cu(I)-catalyzed Huisgen cycloaddition. In this example, we show the design, synthesis, and imaging studies of a series of fluorinated triazole analogues of fluorescent trans-stilbene. We show that, using the same imaging agent, PET can be coregistered with microscopic 3D cryoimaging to seamlessly combine the unique features of quantitative physiologic information provided by PET with microscopic histologic information in high resolution provided by cryoimaging.

Methods and Materials

Chemicals and reagents were used as received without further purification. Glassware was dried in an oven at 130° C. and purged with a dry atmosphere prior to use. Unless otherwise mentioned, reactions were performed open to air. Reactions were monitored by TLC and visualized by a dual short/long wave UV lamp. Column flash chromatography was performed using 230-400 mesh silica gel (Fisher). Preparative TLC was performed on Analtech Preparative TLC Uniplates with UV254 fluorescence indicator (500 μm). NMR spectra were recorded on a Varian Inova 400 spectrometer and 500 MHz Bruker Ascend Avance III HD at room temperature. Florescence spectra were recorded, and chemical shifts for $^1$H and $^{13}$C NMR were reported as δ, part per million (ppm), and referenced to an internal deuterated solvent central line. The abbreviations s, br s, d, dd, ddd, br d, t, dt, q, m, and br m stand for their resonance multiplicity singlet, broad singlet, doublet, doublet of doublets, doublet of doublet of doublets, broad doublets, triplet, triplets of doublets, quartet, multiplet, and broad multiplet, respectively, which were calculated automatically on a MestReNova 10.0. The purity of tested compounds as determined by analytical HPLC was 95%. HRMS-ESI mass spectra were acquired on an Agilent Q-TOF. UV absorption was measured on a Cary 50 Bio spectrophotometer using a standard 1 cm×1 cm quartz cuvette. Fluorescence was measured with a Cary Eclipse spectrophotometer using a 1 cm×1 cm quartz cuvette.

General Method for Alkylation of tert-Butyl (4-((Diethoxyphosphoryl)methyl)phenyl)carbamate (3-5)

To an oven-dried 100 mL round-bottom flask purged with argon gas and fitted with a magnetic stir bar, sodium hydride (2 equiv 95%) and tert-butyl (4-((diethoxyphosphoryl) methyl)phenyl)carbamate (1 equiv) were added together with dry THF (25 mL) at 0° C. and purged with argon gas. Iodo-alkane (3 equiv) was added slowly dropwise after 30 min at 0° C. under argon gas. The reaction was stirred under argon and allowed to reach room temperature overnight. After completion, the reaction was quenched with water and THF was removed in vacuum. The residue was dissolved in DCM and water and the aqueous layer was extracted three times with DCM (30 mL). The organic layers were combined and washed twice with water (50 mL) and once with brine (50 mL). The organic layer was dried over $Na_2SO_4$ and concentrated to give the desired product as a sticky oil, which was used for the next step without further purification.

General Method for Horner-Wadsworth-Emmons Coupling Reaction (6-11)

To an oven-dried 100 mL round-bottom flask with a magnetic stir bar was added sodium hydride (2 equiv, 95%). The flask was purged with argon, and 2 mL of dry DMF was added. This solution was cooled to 0° C., and the phosphonate in DMF (2 mL) was added. The mixture was allowed to stir for 1 h at 0° C. Then the aldehyde in 2 mL of DMF was added slowly. The reaction was continued for another 2 h at 0° C. under argon followed by quenching with water (50 mL) and then extracted with ethyl acetate (50 mL) three times. The organic layer was washed with saturated $NaHCO_3$ (20 mL) and brine (50 mL), dried with $Na_2SO_4$, and concentrated to give the crude product, which was purified with flash chromatography using hexanes and ethyl acetate as eluents.

tert-Butyl (E)-Ethyl(4-(4-(prop-2-yn-1-yloxy)styryl) phenyl)-carbamate (7)

$^1$H NMR (400 MHz, chloroform-d) δ 7.43-7.36 (m, 4H), 7.13 (d, J=8.2 Hz, 2H), 6.98 (d, J=16.3 Hz, 1H), 6.93 (d, J=1.9 Hz, 2H), 6.90 (d, J=7.4 Hz, 1H), 4.63 (dd, J=2.5, 1.1 Hz, 2H), 3.65 (q, J=7.1 Hz, 2H), 2.50 (t, J=2.4 Hz, 1H), 1.42 (s, 9H), 1.13 (t, J=7.1 Hz, 3H). $^{13}$C NMR (100 MHz, chloroform-d) δ 157.4, 154.6, 141.7, 135.3, 131.1, 128.1, 127.9, 127.2, 126.7, 126.5, 115.3, 80.2, 78.7, 76.0, 56.0, 45.1, 28.6, 14.2.

tert-Butyl (E)-Propyl(4-(4-(prop-2-yn-1-yloxy) styryl)phenyl)-carbamate (8)

$^1$H NMR (400 MHz, chloroform-d) δ 7.40 (dd, J=8.7, 2.1 Hz, 4H), 7.14 (d, J=8.1 Hz, 2H), 6.99 (d, J=16.5 Hz, 1H), 6.93 (s, 2H), 6.90 (d, J=7.1 Hz, 1H), 4.63 (d, J=2.4 Hz, 2H), 3.62-3.54 (m, 2H), 2.50 (s, 1H), 1.61-1.49 (m, 2H), 1.43 (s, 9H), 0.87 (t, J=7.4 Hz, 3H). $^{13}$C NMR (100 MHz, chloroform-d) δ 157.4, 154.9, 141.8, 135.3, 131.1, 128.2, 127.9, 127.3, 126.7, 126.5, 115.3, 80.2, 78.7, 76.0, 55.99, 51.8, 28.6, 22.0, 11.4.

tert-Butyl (E)-(4-(4-((tert-Butoxycarbonyl)(prop-2-yn-1-yl)amino)-styryl)phenyl)(methyl)carbamate (9)

$^1$H NMR (400 MHz, chloroform-d) δ 7.46 (dd, J=8.7, 6.7 Hz, 4H), 7.31 (d, J=8.2 Hz, 2H), 7.22 (d, J=8.6 Hz, 2H), 7.03 (s, 2H), 4.37 (d, J=2.5 Hz, 2H), 3.26 (s, 3H), 2.27-2.24 (t, J=4.8 1H), 1.46 (s, 18H). $^{13}$C NMR (100 MHz, chloroform-d) δ 154.8, 154.1, 143.3, 141.5, 135.4, 134.4, 128.2, 127.9, 127.8, 126.9, 126.8, 126.5, 125.6, 81.4, 80.6, 80.2, 72.1, 39.9, 37.4, 28.5, 28.5.

tert-Butyl (E)-(4-(4-((tert-Butoxycarbonyl)(prop-2-yn-1-yl)amino)-styryl)phenyl)(ethyl)carbamate (10)

$^1$H NMR (400 MHz, chloroform-d) δ 7.45-7.42 (m, 4H), 7.28 (d, J=8.4 Hz, 2H), 7.14 (d, J=8.5 Hz, 2H), 7.01 (s, 2H), 4.32 (d, J=2.4 Hz, 2H), 3.65 (q, J=7.0 Hz, 2H), 2.23 (t, J=2.4 Hz, 1H), 1.44 (s, 9H), 1.44 (s, 9H), 1.12 (t, J=7.1 Hz, 3H). $^{13}$C NMR (100 MHz, chloroform-d) δ 154.6, 154.1, 142.0, 141.6, 135.4, 135.0, 128.3, 128.0, 127.2, 126.9, 126.9, 126.5, 81.4, 80.3, 80.2, 72.1, 45.0, 39.9, 28.6, 28.5, 14.1.

tert-Butyl (E)-(4-(4-((tert-Butoxycarbonyl)(prop-2-yn-1-yl)amino)-styryl)phenyl)(propyl)carbamate (11)

$^1$H NMR (400 MHz, chloroform-d) δ 7.48-7.45 (m, 4H), 7.31 (d, J=8.4 Hz, 2H), 7.18 (d, J=8.3 Hz, 2H), 7.05 (s, 2H), 4.37 (d, J=2.5 Hz, 2H), 3.62-3.58 (m, 2H), 2.26 (t, J=2.4 Hz, 1H), 1.63-1.52 (m, 2H), 1.47 (s, 9H), 1.44 (s, 9H), 0.89 (t, J=7.4 Hz, 3H). 13C NMR (100 MHz, chloroform-d) δ 154.9, 154.1, 142.2, 141.6, 135.4, 135.0, 128.3, 128.0, 127.3, 126.9, 126.5, 81.4, 80.2, 80.2, 72.0, 51.7, 39.9, 28.5, 28.4, 21.9, 11.4.

General Method for Click Chemistry (12-17)

A portion of 1-(4-methylbenzenesulfonate)-2-uoroethanol (1.67 equiv) in DMF (4 mL) was stirred with a suspension of sodium azide (5.6 equiv) at room temperature. After 48 h, the solution was filtered through Celite and the crude 1-azido-2-fluoroethane was used immediately in the next step without further purification. In a separate flask, copper (I) iodide (5.4 equiv) was suspended in methanol (2 mL) under an argon atmosphere with vigorous stirring. In rapid succession, the alkyne precursor (1 equiv) dissolved in methanol (1 mL), the crude 1-azido-2-fluoroethane dissolved in DMF, and triethylamine (5.4 equiv) were added. The reaction mixture was stirred overnight at room temperature, and saturated $NaHCO_3$ (20 mL) was then added followed by extraction with ethyl acetate (20 mL) three times. The combined organic layers were washed with water (50 mL) and brine (50 mL), dried with $Na_2SO_4$, and concentrated to give the crude product, which was purified by column chromatography eluted with hexanes and ethyl acetate.

tert-Butyl (E)-(4-(4-((1-(2-Fluoroethyl)-1H-1,2,3-triazol-4-yl)-methoxy)styryl)phenyl)(methyl)carbamate (12)

$^1$H NMR (400 MHz, chloroform-d) δ 7.70 (d, J=1.0 Hz, 1H), 7.40 (dd, J=8.7, 3.0 Hz, 4H), 7.17 (d, J=8.5 Hz, 2H), 6.95 (s, 3H), 6.93 (d, J=22.8 Hz, 4H), 6.90 (d, J=16.5 Hz, 2H), 4.81 (dd, J=5.2, 4.1 Hz, 1H), 4.67 (ddd, J=14.2, 5.5, 4.3 Hz, 2H), 4.59 (dd, J=5.2, 3.9 Hz, 1H), 3.22 (s, 3H), 1.42 (s, 9H). $^{13}$C NMR (100 MHz, chloroform-d) δ 158.0, 154.9, 144.6, 143.0, 134.7, 130.8, 128.0, 127.9, 126.5, 126.4, 125.7, 124.0, 115.2, 114.8, 82.5, 80.8, 80.6, 62.1, 50.9, 50.7, 37.4, 28.5.

tert-Butyl (E)-(4-(4-((1-(2-Fluoroethyl)-1H-1,2,3-triazol-4yl)-methoxy)styryl)phenyl)(ethyl)carbamate (13)

$^1$H NMR (400 MHz, chloroform-d) δ 7.72-7.70 (m, 1H), 7.40 (dd, J=8.6, 1.8 Hz, 4H), 7.12 (d, J=8.1 Hz, 2H), 6.98 (d, J=16.3 Hz, 1H), 6.96-6.93 (m, 2H), 6.91 (d, J=15.9 Hz, 1H), 5.19 (s, 2H), 4.81 (dd, J=5.2, 4.1 Hz, 1H), 4.75-4.65 (m, 2H), 4.59 (dd, J=5.2, 4.0 Hz, 1H), 3.64 (q, J=7.1 Hz, 2H), 1.40 (s, 9H), 1.12 (t, J=7.1 Hz, 3H). $^{13}$C NMR (100 MHz, chloroform-d) δ 158.0, 154.7, 144.6, 141.7, 135.3, 130.8, 128.1, 127.9, 127.2, 126.7, 126.4, 124.0, 115.2, 114.8, 82.5, 80.8, 80.2, 62.1, 50.9, 50.7, 45.1, 28.6, 14.1.

tert-Butyl (E)-(4-(4-((1-(2-Fluoroethyl)-1H-1,2,3-triazol-4-yl)-methoxy)styryl)phenyl)(propyl)carbamate (14)

$^1$H NMR (400 MHz, chloroform-d) δ 7.70 (s, 1H), 7.40 (dd, J=8.7, 1.9 Hz, 4H), 7.12 (d, J=8.1 Hz, 2H), 6.98 (d, J=16.2 Hz, 1H), 6.96-6.93 (m, 2H), 6.91 (d, J=16.2 Hz, 1H), 5.18 (s, 2H), 4.80 (dd, J=5.2, 4.1 Hz, 1H), 4.67 (ddd, J=14.2, 5.4, 4.3 Hz, 2H), 4.58 (dd, J=5.2, 4.0 Hz, 1H), 3.59-3.52 (m, 2H), 1.57-1.47 (m, 2H), 1.40 (s, 9H), 0.84 (t, J=7.4 Hz, 3H). $^{13}$C NMR (100 MHz, chloroform-d) δ 158.1, 154.9, 144.7, 141.8, 135.3, 130.9, 128.1, 127.9, 127.3, 126.7, 126.4, 124.0, 115.2, 114.8, 82.5, 80.8, 80.2, 62.2, 51.7, 50.9, 50.7, 28.5, 21.9, 11.4.

tert-Butyl (E)-(4-(4-((tert-Butoxycarbonyl)((1-(2-fluoroethyl)-1H-1,2,3-triazol-4-yl)methyl)amino)-styryl)phenyl)(methyl)carbamate (15)

$^1$H NMR (400 MHz, chloroform-d) δ 7.68 (s, 1H), 7.44 (dd, J=8.7, 6.9 Hz, 4H), 7.28 (d, J=7.8 Hz, 2H), 7.22 (d, J=8.6 Hz, 2H), 7.02 (s, 2H), 4.92 (s, 2H), 4.84 (dd, J=5.2, 4.1 Hz, 1H), 4.71 (ddd, J=13.2, 5.3, 4.3 Hz, 2H), 4.62 (dd, J=5.1, 4.1 Hz, 1H), 3.27 (s, 3H), 1.46 (s, 9H), 1.45 (s, 9H). $^{13}$C NMR (100 MHz, chloroform-d) δ 154.6, 154.5, 145.9, 143.3, 142.1, 135.0, 134.5, 128.1, 127.9, 126.8, 126.7, 126.4, 125.6, 123.9, 82.6, 81.2, 80.9, 80.6, 50.8, 50.6, 46.0, 37.4, 28.5, 28.5.

tert-Butyl (E)-(4-(4-((tert-Butoxycarbonyl)((1-(2-fluoroethyl)-1H-1,2,3-triazol-4-yl)methyl)amino)-styryl)phenyl)(ethyl)carbamate (16)

$^1$H NMR (400 MHz, chloroform-d) δ 7.73-7.62 (m, 1H), 7.45 (t, J=8.5 Hz, 4H), 7.31-7.26 (m, 2H), 7.17 (d, J=8.5 Hz, 2H), 7.03 (s, 2H), 4.92 (s, 2H), 4.82 (dd, J=5.2, 4.1 Hz, 1H), 4.69 (ddd, J=12.4, 5.5, 4.3 Hz, 2H), 4.61 (dd, J=5.2, 4.0 Hz, 1H), 3.68 (q, J=7.1 Hz, 2H), 1.45 (s, 9H), 1.44 (s, 9H), 1.16 (t, J=7.1 Hz, 3H). $^{13}$C NMR (100 MHz, chloroform-d) δ 154.6, 154.45, 145.9, 142.1, 141.95, 135.0, 128.1, 128.0, 127.2, 126.9, 126.8, 126.4, 123.9, 82.6, 81.2, 80.9, 80.3, 50.8, 50.6, 46.0, 45.0, 28.5, 28.5, 14.1.

tert-Butyl (E)-(4-(4-((tert-Butoxycarbonyl)((1-(2-fluoroethyl)-1H-1,2,3-triazol-4-yl)methyl)amino)-styryl)phenyl)(propyl)carbamate (17)

$^1$H NMR (400 MHz, chloroform-d) δ 7.68 (s, 1H), 7.45 (dd, J=9.0, 7.2 Hz, 4H), 7.28 (d, J=9.0 Hz, 2H), 7.17 (d, J=8.4 Hz, 2H), 7.03 (s, 2H), 4.92 (s, 2H), 4.84 (dd, J=5.2, 4.1 Hz, 1H), 4.71 (ddd, J=13.2, 5.5, 4.3 Hz, 2H), 4.63 (dd, J=5.2, 4.0 Hz, 1H), 1.62-1.53 (m, 2H), 1.45 (s, 9H), 1.44 (s, 9H), 0.89 (t, J=7.4 Hz, 3H), 0.89 (t, J=12.0 Hz, 3H). $^{13}$C NMR (100 MHz, CDCl$_3$) δ 154.9, 154.5, 146.0, 142.1, 135.0, 128.1, 128.0, 127.3, 126.9, 126.4, 123.9, 82.6, 81.2, 80.9, 80.26, 51.7, 50.8, 50.6, 46.0, 28.5, 28.5, 21.9, 11.4.

General Method for Boc Deprotection (18-23)

The click product was dissolved in 2 mL of methanol. To this mixture was added 2 mL of HCl (1.2 M), and the mixture was stirred for 1.5 h at 60° C. and then sufficient NaOH (1 M) was added to bring the pH to 10. Water was added to the mixture and extracted with ethyl acetate (10 mL) three times, washed with brine (30 mL), dried with Na$_2$SO$_4$, and concentrated to give the crude product. Prep TLC or flash chromatography (hexanes/acetone) yielded the deprotected product.

(E)-4-(4-((1-(2-Fluoroethyl)-1H-1,2,3-triazol-4-yl)methoxy)styryl)-N-methylaniline (18)

$^1$H NMR (400 MHz, DMSO-d$_6$) δ 8.27 (s, 1H), 7.44 (d, J=8.8 Hz, 2H), 7.31 (d, J=8.6 Hz, 2H), 7.07-6.98 (m, 2H), 6.94 (d, J=16.4 Hz, 1H), 6.85 (d, J=16.4 Hz, 1H), 6.52 (d, J=8.7 Hz, 2H), 5.82 (q, J=5.0 Hz, 1H), 5.16 (s, 2H), 4.89 (dd, J=5.3, 4.1 Hz, 1H), 4.81-4.75 (m, 2H), 4.73-4.67 (m, 1H), 2.69 (d, J=5.1 Hz, 3H). $^{13}$C NMR (125 MHz, DMSO-d$_6$) δ 157.4, 149.9, 143.4, 131.5, 127.8, 127.5, 127.4, 125.4, 125.3, 122.9, 115.3, 112.1, 83.0, 81.7, 61.5, 50.6, 50.4, 30.1. HR-MS (ESI) m/z calculated for (C$_{20}$H$_{22}$FN$_4$O) [M+H]$^+$ 353.1772, found 353.1773. HPLC purity: 96.94%, retention time 4.00 min. C-18 reversed-phase HPLC (Phenomenex, 10 mm×250 mm); eluent, acetonitrile:H$_2$O=40:60; flow rate of 1.0 mL/min.

(E)-4-(4-((1-(2-Fluoroethyl)-1H-1,2,3-triazol-4-yl)methoxy)styryl)-N-ethylaniline (19)

$^1$H NMR (500 MHz, chloroform-d) δ 7.74 (s, 1H), 7.40 (d, J=8.1 Hz, 2H), 7.33 (d, J=8.0 Hz, 2H), 6.96 (d, J=8.1 Hz, 2H), 6.90 (d, J=16.3 Hz, 1H), 6.84 (d, J=16.3 Hz, 1H), 6.59 (d, J=8.0 Hz, 2H), 5.24 (s, 2H), 4.85 (t, J=4.8 Hz, 1H), 4.76 (t, J=4.8 Hz, 1H), 4.71 (t, J=4.8 Hz, 1H), 4.65 (t, J=4.8 Hz, 1H), 3.18 (q, J=7.1 Hz, 2H), 1.27 (t, J=6.7 Hz, 3H). $^{13}$C NMR (125 MHz, chloroform-d) δ 157.2, 147.8, 144.7, 131.6, 127.5, 127.3, 127.2, 126.9, 123.8, 123.7, 115.0, 112.8, 82.2, 80.8, 62.0, 50.7, 50.5, 38.5, 14.8. HR-MS (ESI) m/z calculated for (C$_{21}$H$_{24}$FN$_4$O) [M+H]$^+$ 367.1929, found 367.1932. HPLC purity: 96.22%, retention time 4.02 min. C-18 reversed-phase HPLC (Phenomenex, 10 mm×250 mm); eluent, acetonitrile:H$_2$O=40:60; flow rate of 1.0 mL/min.

(E)-4-(4-((1-(2-Fluoroethyl)-1H-1,2,3-triazol-4-yl)methoxy)styryl)-N-propylaniline (20)

$^1$H NMR (400 MHz, chloroform-d) δ 7.68 (s, 1H), 7.33 (d, J=8.7 Hz, 2H), 7.25 (d, J=8.5 Hz, 2H), 6.89 (d, J=8.7 Hz, 2H), 6.83 (d, J=16.2 Hz, 1H), 6.77 (d, J=16.3 Hz, 1H), 6.51 (d, J=8.5 Hz, 2H), 5.17 (s, 2H), 4.80 (dd, J=5.2, 4.1 Hz, 1H), 4.67 (dt, J=13.4, 4.6 Hz, 2H), 4.61-4.56 (m, 1H), 3.04 (t, J=7.1 Hz, 2H), 1.57 (p, J=7.3 Hz, 2H), 0.93 (t, J=7.4 Hz, 3H). $^{13}$C NMR (100 MHz, chloroform-d) δ 157.4, 148.2, 144.9, 131.8, 127.7, 127.4, 127.3, 126.9, 123.9, 115.1, 112.9, 82.5, 80.8, 62.2, 50.9, 50.7, 45.9, 22.9, 11.8. HR-MS (ESI) m/z calculated for (C22H26FN4O) [M+H]$^+$ 381.2085, found 381.2090. HPLC purity: 96.28%, retention time 6.50 min. C-18 reversed-phase HPLC (Phenomenex, 10 mm×250 mm); eluent, acetonitrile:H$_2$O=40:60; flow rate of 1.0 mL/min.

(E)-N-((1-(2-Fluoroethyl)-1H-1,2,3-triazol-4-yl)methyl)-4-(4-(methylamino)styryl)aniline (21)

$^1$H NMR (400 MHz, chloroform-d) δ 7.55 (s, 1H), 7.32 (dd, J=8.6, 1.8 Hz, 4H), 6.83 (d, J=1.7 Hz, 2H), 6.64 (d, J=8.6 Hz, 2H), 6.58 (d, J=8.6 Hz, 2H), 4.82 (dd, J=5.1, 4.2 Hz, 1H), 4.71 (dd, J=5.2, 4.1 Hz, 1H), 4.65 (d, J=5.2, 4.2 Hz, 1H), 4.59 (dd, J=5.2, 4.1 Hz, 1H), 2.85 (s, 3H). 13C NMR (100 MHz, chloroform-d) δ 148.7, 146.7, 146.7, 128.6, 127.6, 127.4, 127.4, 125.5, 124.7, 122.7, 113.5, 112.7, 82.6, 80.8, 50.8, 50.6, 40.1, 30.9. HR-MS (ESI) m/z calculated for ($C_{20}H_{23}FN_5$) [M+H]$^+$ 352.1932, found 352.1933. HPLC purity: 95.64%, retention time 4.47 min. C-18 reversed-phase HPLC (Phenomenex, 10 mm×250 mm); eluent, acetonitrile:$H_2O$=50:50; flow rate of 1.0 m/min.

(E)-N-((1-(2-Fluoroethyl)-1H-1,2,3-triazol-4-yl)methyl)-4-(4-(ethylamino)styryl)aniline (22)

$^1$H NMR (400 MHz, chloroform-d) δ 7.57 (s, 1H), 7.31 (dd, J=8.5, 3.6 Hz, 4H), 6.82 (d, J=1.5 Hz, 2H), 6.64 (d, J=8.5 Hz, 2H), 6.58 (d, J=8.5 Hz, 2H), 4.89-4.82 (m, 1H), 4.72 (dd, J=5.2, 4.0 Hz, 1H), 4.69-4.63 (m, 1H), 4.63-4.56 (m, 1H), 4.49 (s, 2H), 3.18 (q, J=7.1 Hz, 2H), 1.26 (t, J=7.1 Hz, 3H). $^{13}$C NMR (100 MHz, chloroform-d) δ 147.8, 146.8, 146.65, 128.6, 127.5, 127.4, 127.4, 125.5, 124.6, 122.7, 113.5, 113.0, 82.6, 80.7, 50.9, 50.6, 40.1, 38.7, 15.1. HR-MS (ESI) m/z calculated for ($C_{21}H_{25}FN_5$) [M+H]$^+$ 366.2089, found 366.2089. HPLC purity: 98.41%, retention time 5.05 min. C-18 reversed-phase HPLC (Phenomenex, 10 mm×250 mm); eluent, acetonitrile:H2O=30:70; flow rate of 1.0 mL/min.

(E)-N-((1-(2-Fluoroethyl)-1H-1,2,3-triazol-4-yl)methyl)-4-(4-(propylamino)styryl)aniline (23)

$^1$H NMR (400 MHz, chloroform-d) δ 7.57 (s, 1H), 7.31 (dd, J=8.5, 5.1 Hz, 4H), 6.82 (d, J=1.8 Hz, 2H), 6.65 (d, J=8.4 Hz, 2H), 6.58 (d, J=8.5 Hz, 2H), 4.84 (t, J=4.6 Hz, 1H), 4.76-4.70 (m, 1H), 4.70-4.64 (m, 1H), 4.64-4.58 (m, 1H), 4.49 (s, 2H), 3.10 (t, J=7.1 Hz, 2H), 1.65 (q, J=7.2 Hz, 3H), 1.00 (t, J=7.4 Hz, 3H). $^{13}$C NMR (125 MHz, chloroform-d) δ 147.6, 146.6, 146.5, 128.5, 127.3, 127.2, 127.2, 125.4, 124.4, 122.5, 113.3, 112.8, 82.2, 80.8, 50.6, 50.5, 45.8, 39.9, 31.9, 22.7, 11.6. HR-MS (ESI) m/z calculated for ($C_{22}H_{27}FN_5$) [M+H]$^+$ 380.2245, found 380.2248. HPLC purity: 99.93%, retention time 8.13 min. C-18 reversed-phase HPLC (Phenomenex, 10 mm×250 mm); eluent, acetonitrile:$H_2O$=30:70; flow rate of 1.0 mL/min.

tert-Butyl (4-Formylphenyl)(prop-2-yn-1-yl)carbamate (24)

To an oven-dried 100 mL round-bottom flask purged with argon gas and fitted with a magnetic stir bar was added sodium hydride (140 mg, 95%) and tert-butyl (4-formylphenyl)carbamate (1.02 g), which was purged with argon gas under dry THF (25 mL) at 0° C. 3-Bromoprop-1-yne (1.55 mL, 80% in toluene) was added slowly dropwise after 30 min at 0° C. under argon gas. The reaction was stirred under argon and allowed to reach room temperature. After 3 h, the reaction was quenched with water and extracted with ethyl acetate (30 mL×3). The organic layers were combined and washed twice with water (50 mL) and once with brine (50 mL). The organic layer was dried over $Na_2SO_4$ and concentrated to give the crude product. Flash chromatography (Hex:EA/8:1) yielded 24 (1.06 g, 89%) as an oil. $^1$H NMR (400 MHz, chloroform-d) δ 9.92 (s, 1H), 7.87-7.78 (m, 2H), 7.55-7.47 (m, 2H), 4.39 (dd, J=2.5, 0.9 Hz, 2H), 2.28 (t, J=2.4 Hz, 1H), 1.46 (s, 9H). $^{13}$C NMR (100 MHz, chloroform-d) δ 191.2, 153.1, 147.6, 133.4, 130.2, 125.4, 82.1, 79.4, 72.4, 39.4, 28.2.

2-Azidoethyl 4-Methylbenzenesulfonate (25)

To an oven-dried 100 mL round-bottom flask purged with argon gas and fitted with a magnetic stir bar was added DCM (15 mL), 2-azidoethan-1-ol (2.3 mL, 0.5 M in methyl tert-butyl ether), 4-toluenesulfonyl chloride (0.33 g), and $Et_3N$ (0.32 mL). The reaction mixture was allowed to stir overnight at room temperature, and water was then added followed by two extractions with DCM (30 mL). The organic layers were combined and washed with water (50 mL) and brine (50 mL). Flash chromatography (Hex:EA/4:1) yielded 25 (0.22 g, 79%). $^1$H NMR (400 MHz, chloroform-d) δ 7.85-7.76 (m, 2H), 7.42-7.34 (m, 2H), 4.15 (ddd, J=5.2, 4.5, 0.9 Hz, 2H), 3.53-3.42 (m, 2H), 2.45 (s, 3H).

Animal Preparation and Studies

All animal experiments were performed in accordance with guidance protocol approved by the Institutional Animal Care and Use Committee (IACUC) of Case Western Reserve University (protocols 2016-0028, 2016-0023). The 8-week old WT C57BL/6 mice were used for all of the in vitro and ex vivo tissue staining and SD rats (Harlan Laboratory, Indianapolis, Ind.) and Shiverer mice (Jackson Laboratory, Bar Harbor, ME) were used for microPET/CT imaging studies. The animals were fasted overnight prior to imaging but had access to water. Their diet was then replenished after microPET/CT imaging.

Brain Focal Demyelination Rat Model

Sprague-Dawley female rats (220-250 g, 8 weeks old) were anesthetized and positioned in a stereotaxic frame (Stoelting). A small incision was made in the scalp, and the corpus callosum was targeted using the following stereotaxic coordinates, relative to bregma: anterior-posterior, 0.0 mm; medial-lateral, 2.0 mm; and dorsal-ventral, 3.4 mm. A small hole was drilled in the skull, and a 26S-gauge needle attached to a 10 μL Hamilton Syringe was lowered into the corpus callosum according to the dorsal-ventral coordinate. A microinjector pump (Stoelting) controlled the infusion of 6 μL of lysolecithin (LPC, 0.1% in saline) at a rate of 0.25 μL/min, after which the needle was left in place for 2 min in order to prevent liquid reflux out of the brain parenchyma. The incision was then closed using 5-0 Ethicon sutures, and the animals were allowed to recover on a heating pad. After 5-7 days, the animals were ready for study.

Rat SCI Model

Sprague-Dawley female rats (220-250 g, 8 weeks old) were anesthetized and a restricted laminectomy was conducted to expose the dorsal surface of T13. The vertebral column between T12 and L1 was then stabilized with clamps and forceps fixed to the base of an Infinite Horizon impact device. The midpoint of T13 was impacted with a force of 250 kDyn using a 2.5 mm stainless steel impactor tip, which was used to induce a moderately severe contusive injury to the spinal cord. The musculature was then sutured over the laminectomy site and the skin closed with wound clips followed by subsequent treatment with Marcaine at the incision site. The force/displacement graph was used to monitor impact consistency. After surgery, the animals were carefully monitored daily for pain and body weight with manual bladder expression 2-3 times daily to stimulate reflex voiding until the animals could urinate independently.

In Vitro Tissue Staining of Brain

Wild-type mice (20-22 g, 8 weeks old) were deeply anesthetized and perfused with precooled saline (4° C., 10 mL/min for 1 min followed by 7 mL/min for 6 min), which was followed by fixation with precooled 4% PFA in PBS (4° C., 10 mL/min for 1 min followed by 7 mL/min for 6 min). Brain tissues were then removed, postfixed by immersion in 4% PFA overnight, dehydrated in 10%, 20%, and 30% sucrose solution, embedded in a freezing compound (OCT, Fisher Scientific, Suwanee, GA.), and sectioned at 20 μm increments with a cryostat (Thermo HM525, Thermo Fisher Scientific Inc., Chicago, IL., USA). To provide staining sections for preliminary FIR measurement, brain sections were collected from AP (1.0) to AP (−0.1), and the first 12 sections were mounted in order on the bottom of 12 superfrost slides (Fisher Scientific) with one section on each slide. Sections 13-24 were mounted in order on the middle of each slide, and sections 25-36 were mounted in order on the top of each slide. Sections were then incubated with tested compounds (1 mM, 5% DMSO in 1×PBS (pH 7.0), 6 sections per compound) for 25 min at room temperature in the dark. Excess compounds were washed by brie y rinsing the slides in PBS (1×) and coverslipped with fluoromount-G mounting media (Vector Laboratories, Burlingame, CA). Sections were then examined under a microscope (Leica DM4000B, Leica Microsystem Inc., Buffalo Grove, IL, USA) equipped for fluorescence (DFC7000T), and images of the stained mouse whole brain sections were acquired with the same exposure time.

FIR Measurement

ImageJ software was used to quantify fluorescent intensity on six sections of each tested compound. A ROI was selected on the genus of the corpus callosum (gcc, white matter), and the same size of ROI was applied on the midline between gcc and the edge of the section (see FIG. 8A), which is considered to be gray matter. Images were analyzed by two experienced individuals. The FIR values of white matter to gray matter were then calculated.

Ex vivo Tissue Staining

Wild-type mice were administered the newly synthesized compounds (40 mg/kg) via tail vein injection, and 30-60 min later the mice were perfused transcardially with saline followed by 4% PFA in PBS. Brains and spinal cords were then removed, postfixed by immersion in 4% PFA overnight, dehydrated in 30% sucrose solution, cryostat sectioned at 100 μm, mounted on superfrost slides, and images were acquired directly using a Leica fluorescent microscope.

In Vitro Staining of Rat Brain Treated with LPC

Five days after surgery, the rats were anesthetized and perfused with saline followed by 4% PFA. Brain tissues were then removed, postfixed in 4% PFA overnight, dehydrated in 10%, 20%, and 30% sucrose solution, embedded in OCT, and sectioned at 20 μm with a cryostat. To determine if the selected compound can differentiate demyelinated regions from normal myelinated sheaths, we conducted in vitro tissue staining using spinal cord sections taken from LPC-treated rats. LPC-treated spinal cord sections were then incubated with tested compounds (1 mM, 5% DMSO in 1×PBS (pH 7.0)) for 25 min at room temperature in the dark. Excess compounds were washed by brie y rinsing the slides in PBS (1×) and coverslipped with fluoromount-G mounting media (Vector Laboratories, Burlingame, CA). Sections were then examined under a microscope (Leica DM4000B, Leica Microsystem Inc., Buffalo Grove, IL, USA) equipped for fluorescence (DFC7000T), and images of the stained mouse whole brain sections were acquired with the same exposure time. In the meantime, standard Luxol-Fast-Blue (LFB) staining was performed on the adjacent LPC-treated spinal cord section for comparison.

Radiosynthesis

No carrier-added (nca) [$^{18}$F] fluoride was produced by a cyclotron (Eclipse High Production, Siemens) via the nuclear reaction $^{18}$O (p,n) $^{18}$F. At the end of bombardment (EOB), the activity of aqueous [$^{18}$F] uoride (50-100 mCi) was transferred to the GE Tracerlab Fxn synthesizer by high helium pressure. After delivery, the radioactive solution was passed through a Sep-Pak light QMA cartridge (Waters, preconditioned with 5 mL of water followed by 10 mL of air in a syringe) and was eluted by $K_2CO_3$ solution (6 mg in 0.6 mL of water) followed by $K_{222}$ solution (12 mg in 1 mL ofacetonitrile). The solvent was evaporated under a steam of helium at 85° C. for 5 min, and the residue was vacuumed at 55° C. for another 3 min to get the anhydrous $K_{222}$/[$^{18}$F] complex. A solution of the tosylated precursors (25, 3-5 mg, in 0.5 mL of acetonitrile) was added to the above dried complex, and the mixture was heated at 95° C. for 10 min. Cooling water (10 mL) was then added to the reaction vessel, and the mixture was passed through a C18 plus cartridge and an Oasis HLB plus cartridge in series (Waters, preconditioned with acetonitrile (10 mL), water (10 mL), and followed by air (~10 mL)). An additional 20 mL of water was used to rinse the reaction vial and the cartridges, followed by air (~20 mL) to remove the residual water from the HLB cartridge. DMF (400 μL+500 μL) was used to elute [$^{18}$F]26 from the Waters HLB cartridge into a reaction vial prefilled with a mixture of the click reaction precursor 9 (5 mg), 1.25 mg of $CuSO_4.5H_2O$, 4 mg of sodium ascorbate, and 3 mg of BPDS in 50 μL (water/DMF=4/1). The mixture was then stirred for 10 min at 90° C. After cooling, 0.5 mL of HCl (1 M) was added and the resulting mixture was heated at 90° C. for 10-20 min. A NaOH solution (0.5 mL, 1 M) and water (15 mL) were then added, and the resulting mixture was passed through a preconditioned Sep-Pak C-18 cartridge. The cartridge was then washed with another 20 mL of water, and the crude products were eluted with 1 mL of acetonitrile which was further purified by semipreparative HPLC (Phenomenex C-18, 10 mm×250 mm; acetonitrile: $H_2O$=65:35; flow rate of 3 mL/min). The radioactive fraction containing the desired products was collected, diluted with water, loaded onto a Sep-Pak C-18 cartridge, and eluted with 1 mL of ethanol. After evaporation, the residue was redissolved in 5% ethanol in saline solution and filtered (0.22 μm) into a sterile injection bottle for animal use. RCP and specific activity (SA) were determined by analytical HPLC (Phenomenex C-18; 4.6 mm×250 mm; acetonitrile: $H_2O$=65:35; flow rate of 1 mL/min). SA was calculated from the area of the UV peak of purified F-18 compound and titrated with the standard curve of the nonradioactive reference compound of known concentration.

In vivo MicroPET/CT Imaging Studies

MicroPET/CT imaging was performed using a Siemens Inveon microPET/CT scanner in the Case Center for Imaging Research. For better anatomic localization, CT coregistration was applied. Before microPET imaging, CT scout views were taken to ensure the brain tissues were placed in the co-scan field of view (FOV) where the highest image resolution and sensitivity are achieved. Under anesthesia, radiotracer was administered via tail vein injection and immediately followed by a dynamic PET acquisition up to 60 min. After the microPET acquisition was done, the rat was moved into the CT field and a two-bed CT scan was performed. A two-dimensional ordered subset expectation maximization (OSEM) algorithm was used for image reconstruction using CT as attenuation correction. For quantitative analysis, the resultant PET images were registered to the CT images, which enabled us to accurately define the ROI and quantify the radioactivity concentrations. In this study, the whole brains of rats were used as ROI and the radioactivity concentrations were determined in terms of SUVs.

Coregistration of in Situ 3D Cryoimaging with PET/CT Imaging

After microPET imaging studies, the rats were administered compound 21 (3-5 mg) via tail vein injection, and 60 min later the rats were perfused transcardially with saline followed by 4% PFA in PBS. Spinal cords were then removed, postfixed by immersion in 4% PFA overnight, dehydrated in 30% sucrose solution, cryostat sectioned at 100 μm, mounted consecutively on superfrost slides, and images were sequentially acquired directly using a Leica fluorescent microscope to give a series of 2D microscopic images along the length of the spinal cord. Slices were aligned sequentially using a semiautomated image registration algorithm. Starting from the first slice image, the current slice was used as the reference image for alignment and the next slice was the floating image. The floating image was aligned via control point pairs between corresponding anatomic features in the two images. A 2D rigid-body transformation (translation, rotation) was used to transform the floating image to align with the reference and a minimum of three control point pairs were used for the transformation. Once two slices were aligned, the algorithm continued with the newly aligned image serving as the reference image and the next slice in the sequence serving as the floating image. All slices in the sequence were aligned by this technique, giving a 3D reconstructed fluorescence image volume. Image volumes from fluorescence, PET, and CT were visualized in Amira using volume rendering and aligned based on the shape of the spine and fiducials from the vertebrae.

In Situ Autoradiography

Wild-type mice were euthanized at 30 min post iv injection of [$^{18}$F]21 (111 MBq, 3.0 mCi). The brains were rapidly removed, placed in OCT embedding medium, and frozen at −20° C. After reaching equilibrium at this temperature, the brains were coronally sectioned at 60 μm on a cryostat and mounted on superfrost slides. After drying by air at room temperature, the slides were put in a cassette and exposed for 20 min to film to obtain images.

Results

Chemical Synthesis

A series of fluorinated triazole derivatives of MeDAS with different N-alkyl groups were of designed and synthesized as shown in Scheme 1. Incorporation triazole provides a pharmacophore that can be readily synthesized and radiolabeled through a click reaction. Currently, the most common method of F-18 labeling is the direct nucleophilic substitution of sulfonic acid esters (such as tosylates, triflates, or mesylates) into the precursor with fluorine-18, but this reaction condition raises the possibility of side reactions like E-2 elimination and substitution of other potential leaving groups. Over the past decade, a 1,3-dipolar cycloaddition reaction between alkynes and azides has been widely applied to radiolabeling with high specificity and good yields, which thereby allows efficient F-18 labeling of radiopharmaceuticals.

Scheme 9. Click Synthesis of Fluorinated MeDAS Analogues (18-23)$^a$

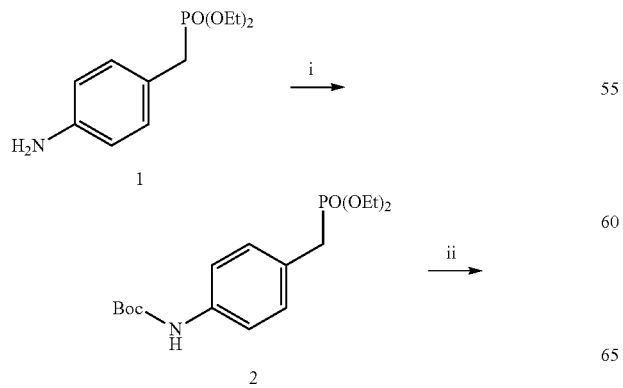

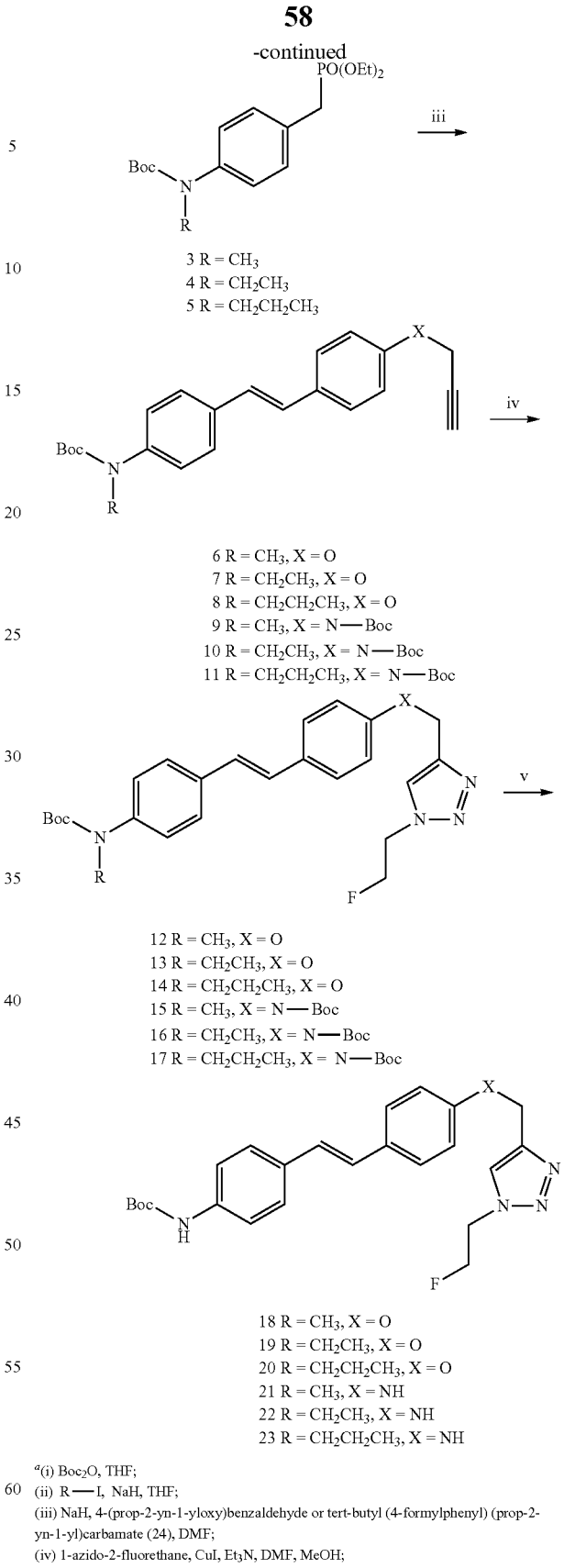

$^a$(i) Boc$_2$O, THF;
(ii) R—I, NaH, THF;
(iii) NaH, 4-(prop-2-yn-1-yloxy)benzaldehyde or tert-butyl (4-formylphenyl) (prop-2-yn-1-yl)carbamate (24), DMF;
(iv) 1-azido-2-fluoroethane, CuI, Et$_3$N, DMF, MeOH;
(v) HCl, H$_2$O, NaOH.

As shown in Scheme 1, the synthesis starts with Boc protection of the amino group of compound diethyl (4-aminobenzyl) phosphonate (1) to generate compound 2, followed by alkylation with iodoalkanes to obtain various alkylated tert-butyl (4-((diethoxyphosphoryl)methyl)-phenyl)-carbamate (3-5). The obtained compounds 3-5 were coupled with corresponding aldehydes through the Horner-Wads-worth-Emmons reaction to generate N-alkylated tert-butyl (E)-(4-(4-(prop-2-yn-1-yloxy)styryl)phenyl)carbamate (6-8) having a propargyloxyl group in 72-74% yield, and N-alkylated tert-butyl (E)-(4-(4-((tert-butoxycarbonyl)(prop-2-yn-1-yl)-amino)styryl)phenyl)carbamate (9-11) with a Boc-protected propargylamino group in 68-72% yield. Click reactions between compounds 6-11 and 1-azido-2-fluoroethane catalyzed by copper(I) yielded fluorinated triazoles (12-17) in 50-60% yield, which underwent Boc-deprotection to give compounds 18-23 as the nal products in 70-75% yield.

Fluorescence Properties

Figure 7:
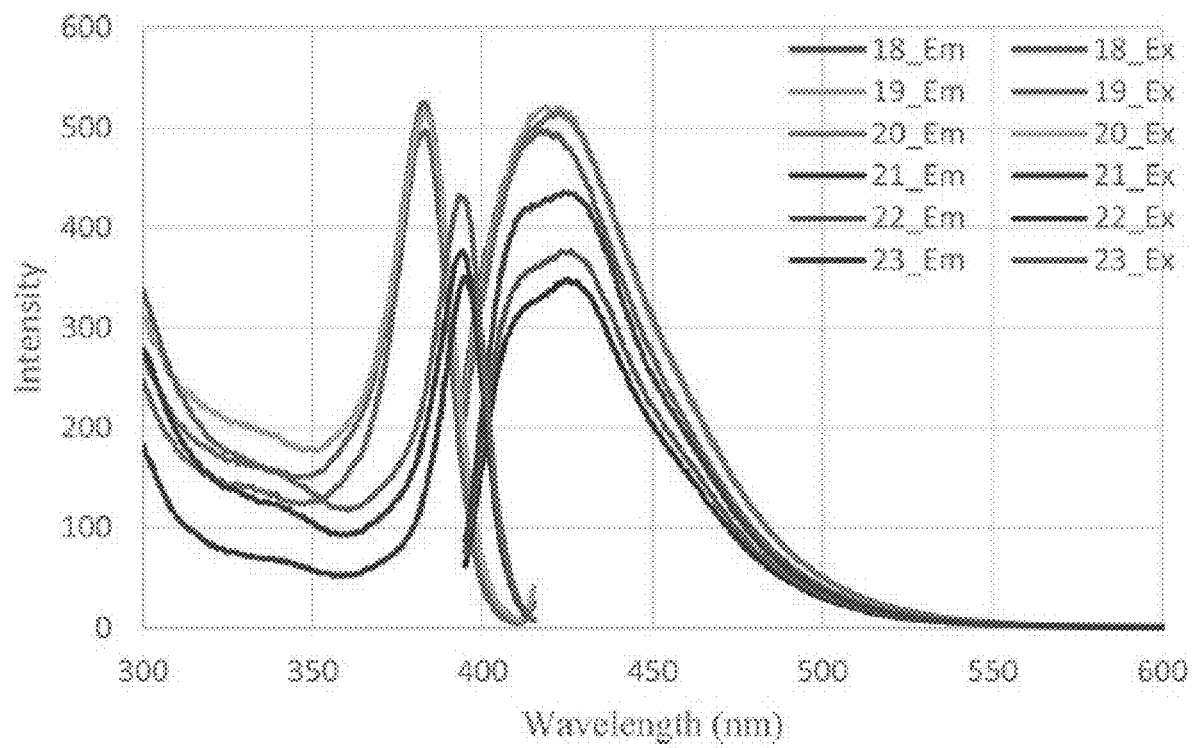
FIG. 7 illustrates plots showing excitation (Ex) and emission (Em) spectra of compounds 18-23 (0.3 mM in methylene chloride). Excitation spectra scans from 300 to 415 nm and emission spectra scans from 394 to 600 nm. Bandwidth at 5 nm, scan at 120 nm/min, and integration time of 0.5 s. Maximal excitation wavelengths of compounds 18-23 were at 375 and 395 nm, while maximal emission wavelengths of compounds 18-23 were at 430 nm.

The excitation and emission spectra (0.3 mM in dichloromethane (DCM)) of the newly synthesized compounds were recorded using a Cary Eclipse fluorescent spectrophotometer. As shown in FIG. 7, all compounds were fluorescent with excitation wavelengths in the range of 300-415 nm and emission wavelengths in the range of 394-600 nm.

In vitro Staining of Intact Myelin

Figure 8A:
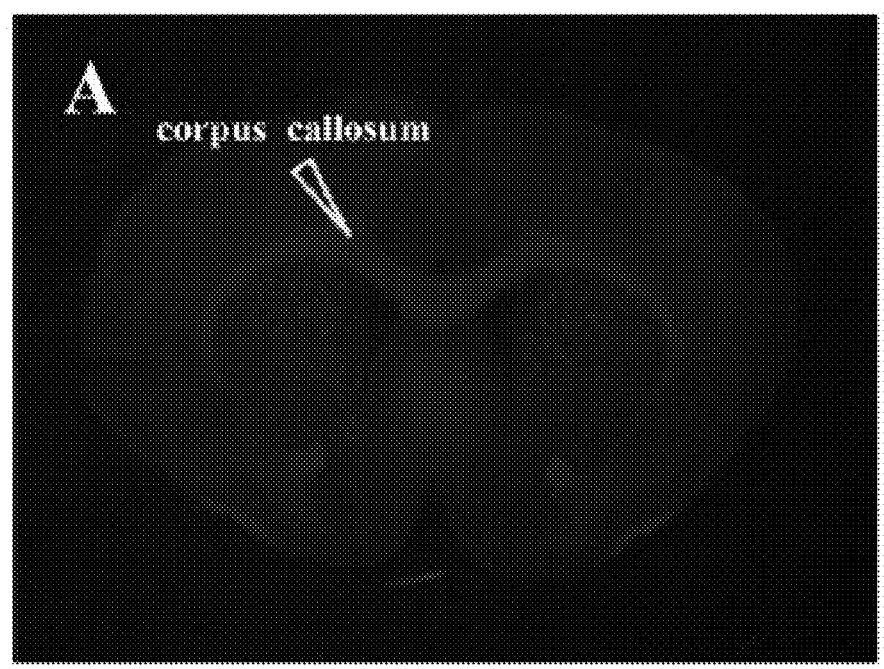
FIGS. 8(A-H) illustrate images showing tissue staining of compound 21 in wild-type mouse brain and demyelination LPC rat model brain, and preliminary compound screening with FIR calculated based on ROIs. Fresh frozen wild-type mouse brain sections were stained with compound 21, and highly myelinated corpus callosum (A) and cerebellum myelin track (B) were clearly visualized. In vitro tissue staining showed that compound 21 can be used to detect demyelinated lesion present in a rat brain of LPC model (C), which is further confirmed by LFB and cresyl violet staining (D) on an adjacent tissue section. In situ staining proved that compound 21 crosses the BBB and stains myelinated areas of the mouse brain (E) and spinal cord (F). Representative in vitro tissue staining of coronal sections showing ROIs used for calculation of FIRs between white matter and gray matter (G), and FIRs of compounds 18-23 were calculated by ImageJ (H).

The newly synthesized compounds were first examined for myelin binding by in vitro staining of frozen mouse brain tissue sections. Because of the inherent fluorescence, the myelin-binding properties were directly examined by fluorescent microscopy after staining with each tested compound at 10 μM concentration. All compounds labeled intact myelin sheaths present in the white matter included the corpus callosum, striatum, and cerebellum (FIG. 8A,B).

Because myelin is rich in white matter and deficient in gray matter, the difference of staining between the white matter and gray matter is expected to reflect binding specificity of the test compounds. We thus calculated the fluorescent intensity ratio (FIR) of each test compound in the same region of interest (ROI) between the white matter and gray matter using ImageJ. As shown in FIG. 8G, ROIs of same size were drawn on a representative region in the genus of the corpus callosum (gcc) and in the subcortical gray matter (cortex), respectively. The newly synthesized compounds fell into two categories based on the calculated FIR (FIG. 8F). The three O-linked phenyl ring compounds (E)-4-(4-((1-(2-fluoroethyl)-1H-1,2,3-triazol-4-yl)methoxy)styryl)-N-alkane-aniline (18-20) showed FIRs ~1. The other three N-linked phenyl ring compounds (E)-N-((1-(2-fluoroethyl)-1H-1,2,3-triazol-4-yl)methyl)-4-(4-(alkane-amino)styryl)-aniline (21-23) showed FIRs ~1.5. The relatively higher FIRs indicated a higher degree of specific binding. This study suggests that an N-linked phenyl ring is more myelin-specific than an O-linked phenyl ring in terms of binding to myelin sheaths.

Lipophilicity

To penetrate the blood-brain barrier (BBB), lipophilicity is one of the three primary requirements that small molecules have to meet. Research showed that a lipophilicity value of 1.0-3.5 is ideal for a small molecule to cross the BBB. On the basis of the structures, we calculated the lipophilicity of the newly designed compounds as shown in Table 1. The C log P value of N-linked compound 21 is 2.86, which is very similar to our model compound MeDAS (2.91). Thus, compound 21 was selected for further evaluation.

TABLE 2

| Compound | Structure | Log P |
|---|---|---|
| 18 | 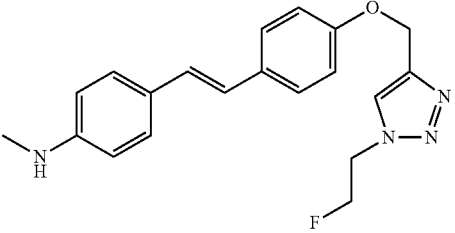 [SMILES: CNc1ccc(/C=C/c2ccc(OCc3cn(CCF)nn3)cc2)cc1] | 3.66 |
| 19 | 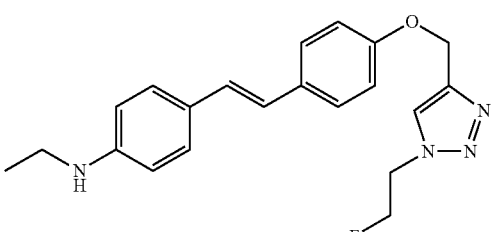 | 4.12 |
| 20 | 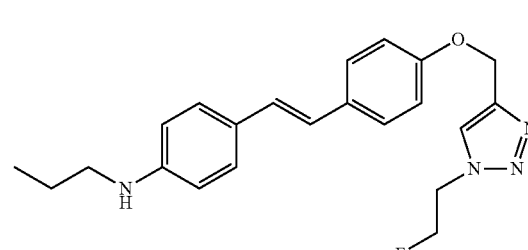 | 4.65 |

TABLE 2-continued

| Compound | Structure | Log P |
|---|---|---|
| 21 | 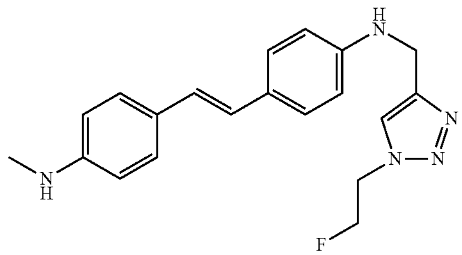 [SMILES: CNc1ccc(/C=C/c2ccc(NCc3cn(CCF)nn3)cc2)cc1] | 2.86 |
| 22 | 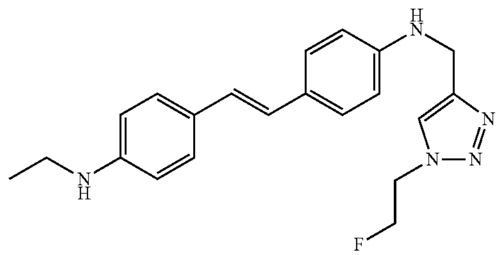 [SMILES: CCNc1ccc(/C=C/c2ccc(NCc3cn(CCF)nn3)cc2)cc1] | 3.38 |
| 23 | 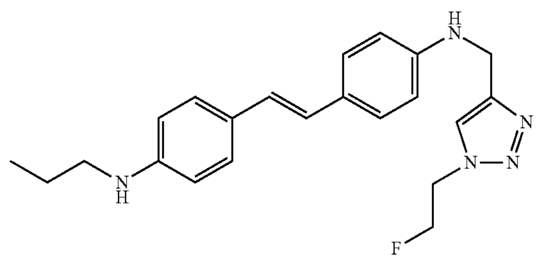 [SMILES: CCCNc1ccc(/C=C/c2ccc(NCc3cn(CCF)nn3)cc2)cc1] | 3.91 |

In Vitro Detection of Focal Demyelination in Rats

We then examined if compound 21 can be used to detect demyelinated lesions present in a rat model of focal demyelination. In this model, demyelination was induced by lysolecithin (LPC), which was stereotaxically injected into the corpus callosum of the right hemisphere. As shown in FIG. 8C, compound 21 was capable of detecting the demyelinated focal lesion by fluorescent staining. The same foci of demyelination in the adjacent section were confirmed by conventional Luxol-Fast-Blue (LFB) and cresyl violet staining (FIG. 8D). This result demonstrates that compound 21 can be used to detect brain lesions based on specific binding to myelin.

In Situ Staining of Compound 21

Following the in vitro studies, we then investigated the ability of compound 21 to readily enter the brain and bind to myelin in situ. A dose of 1.0 mg of compound 21 (50 mg/kg) was administered via the tail vein to wild-type (WT) mice. One hour after injection, the mice were perfused with saline followed by 4% paraformaldehyde (PFA) and the brain and spinal cord were removed and sectioned. The distribution of compound 21 was then directly examined under a fluorescent microscope. As shown in FIG. 8E,F, strong fluorescence was visualized in the myelinated regions including the corpus callosum, striatum, cerebellar white matter, and the white matter of spinal cord. These studies suggest that compound 21 readily entered the brain and spinal cord and localized in all the myelinated regions in proportion to the myelin content.

Radiosynthesis

Encouraged by the in vitro and in situ results, we next evaluated the in vivo pharmacokinetic profiles of compound 21 after labeling with positron-emitting nuclide fluorine-18.

As shown in Scheme 2, the radiosynthesis of [$^{18}$F] 21 was accomplished through a click reaction between compound 9 and 2-[$^{18}$F] fluoroethylazide ([$^{18}$F]26). [$^{18}$F]26 was prepared through a nucleophilic substitution of tosylate compound 25 with [$^{18}$F]KF in the presence of $K_2CO_3$ and Kryptofix ($K_{222}$) in MeCN at 95° C. for 10 min. The identity of the product was confirmed using analytical HPLC by coinjection with cold standard compound 21. The radio-chemical purity (RCP) of the final products was >98%, determined by analytical radio-HPLC. The specific activity at the end of synthesis was in the range of 1-2.5 Ci/μmol.

Scheme 10. Radiosynthesis of [$^{18}$F]21 by Click Reaction Followed by Boc Deprotection

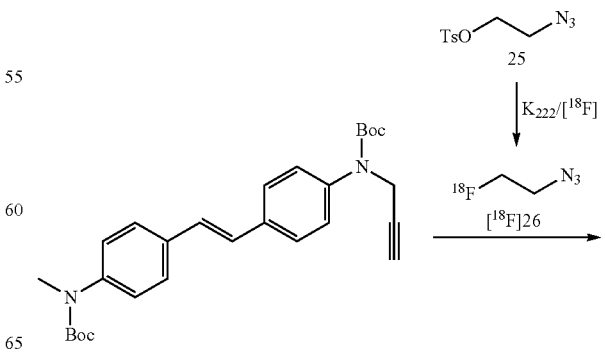

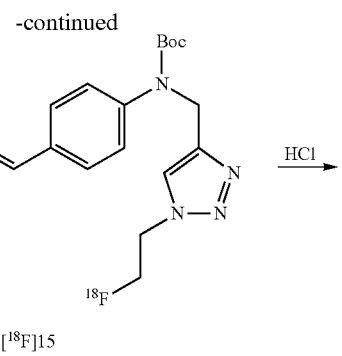

[<sup>18</sup>F]15

[<sup>18</sup>F]21

Quantitative MicroPET/CT Imaging Studies in WT Rats

Following radiosynthesis, the pharmacokinetic profile of [$^{18}$F]21 was fully characterized by quantitative microPET/CT imaging in WT rats (n=3). As shown in FIG. 9, [$^{18}$F]21 exhibited high uptake in the brain. The brain radioactivity peaked at 3 min postinjection followed by rapid clearance before reaching a plateau at 40-60 min postinjection. The time-radioactivity curve fitted well the equation C(SUV) 1.1189 e −0.0514t+0.3041, with a calculated time constant of clearance of 19.45 min.

In Situ Autoradiography

To validate the PET results and confirm that the PET signals were indeed from specific binding to myelin, we conducted ex vivo autoradiography in the mouse brain following administration of [$^{18}$F]21 through tail vein injections. After 1 h, the mouse brain was dissected for coronal tissue sectioning. As shown in FIG. 9E, [$^{18}$F]21 distinctly labeled the corpus callosum, which is the region with a high density of myelin sheaths. The autoradiographic visualization showed that the distribution of [$^{18}$F]21 was consistent with the histological staining of myelinated regions with the corresponding nonlabeled compound 21 (see FIG. 8A). Thus, combination of in situ autoradiography and PET imaging confirmed that [$^{18}$F]21 binds specifically to myelin in vivo.

Quantitative MicroPET/CT Imaging Studies in Shiverer Mice

To further evaluate the in vivo binding specificity of [$^{18}$F]21, we investigated the pharmacokinetic profiles of [$^{18}$F] 21 in a Shiverer mouse model that is deficient in myelin in the brain. Thus, the pharmacokinetic profiles of [$^{18}$F]21 were quantitatively compared between Shiverer mice (C3Fe.SWV-Mbpshi/J, n=2) and age-matched WT mice (CB57J, n=2).

Dynamic emission scans were acquired for 60 min in 3D list mode immediately after [$^{18}$F]21 (0.3 mCi each mouse, 11.1 MBq) was administered. The brain uptake of [$^{18}$F]21 was lower in the Shiverer brain than in the WT littermates (1.25 vs 1.64). After the brain concentration of [$^{18}$F]21 reached a plateau, the SUVs from 40 to 60 min were summarized and compared. As shown in FIG. 10, [$^{18}$F]21 uptake in the Shiverer mouse brain was significantly decreased compared to the control mouse brain. These results suggested that [$^{18}$F]21 indeed binds to myelin in the brain with high specificity.

Quantitative MicroPET/CT Imaging Studies in the Spinal Cord

Figure 11E:
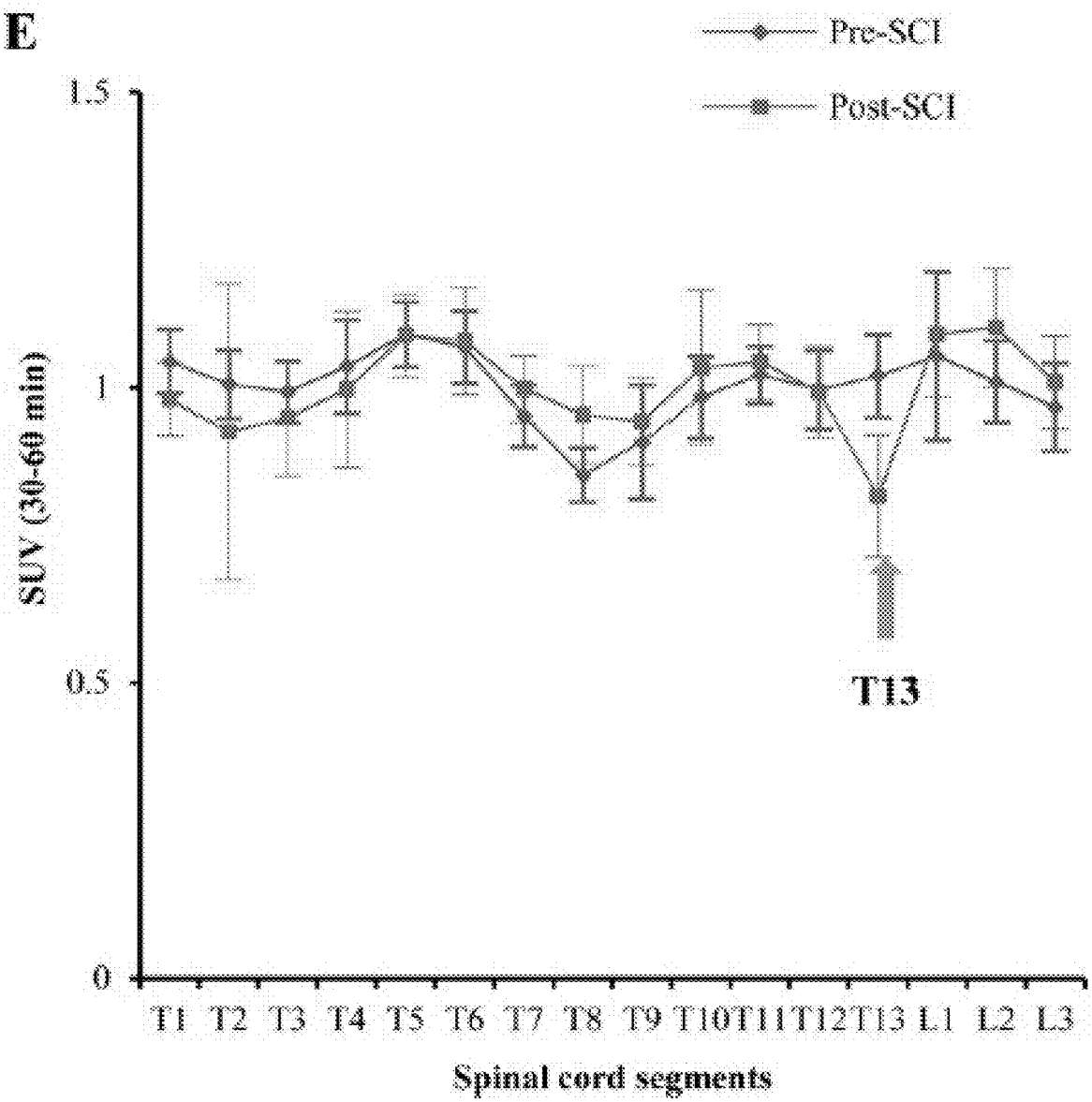
FIGS. 11(A-E) illustrate MicroPET/CT images. Representative PET/CT fusion images in rats acquired before SCI surgery (baseline scan) with higher magnification coronal (A) and sagittal images (B) in the T13 spinal cord. Representative PET/CT fusion images in rats acquired 1 day after SCI surgery with higher magnification coronal (C) and sagittal images (D) in the T13 spinal cord. Note the decrease signal contrast in the SCI animal compared with the baseline scan. (E) Quantification of the total cumulative [$^{18}$F]21 uptake in the T13 ROI 30-60 post injection showed significantly lower uptake in the SCI group compared with baseline scans.

So far, imaging of the spinal cord remains a great challenge. Our studies showed that compound 21 is capable of detecting focal demyelinated lesions induced in the rat brain in vitro. Next, we asked whether [18F]21 PET is capable of in vivo imaging of myelin deficiency or myelin damage in living animal models. We conducted [$^{18}$F]21-PET imaging in a rat model of thoracic contusive SCI. In this model, the contusion was made at T13 to introduce demyelination. In vivo [$^{18}$F]21 PET imaging was performed before (as a baseline scan) and 1 day after contusion. The uptake of [$^{18}$F]21 in every spine segment was then normalized to the average spine uptake. As shown in FIGS. 11A, B, the whole intact thoracic region of the spinal cord could be clearly visualized by [$^{18}$F]21-PET imaging in the control rats, but the lesion at vertebrae level T13 was clearly visualized by [$^{18}$F]21-PET in the SCI model (FIGS. 11C,D). Quantitative analysis of [$^{18}$F]21 uptake in the whole thoracic region (T1-T13), and part of the lumbar vertebra showed distinct patterns of uptake. As shown in FIG. 11E, the uptake of [$^{18}$F]21 in T13 in the SCI group was 0.81, which was significantly lower than that in their own baseline scans (1.02). After microPET/CT imaging, we conducted in situ histological staining of the spinal cord 60 min after injection of nonlabeled compound 21 through the tail vein. As shown in FIG. 12, in situ histological staining of the SCI (T13) tissue section with compound 21 showed that a demyelinated lesion was present at the dorsal column (A), which was confirmed by LFB and cresyl violet staining of the adjacent sections (B).

Coregistration of In Situ 3D Cryoimaging with MicroPET/CT Imaging

To confirm the in vivo imaging of the spinal white matter by PET/CT, we acquired 2D fluorescence images and generated a 3D reconstructed image stack. Thus, nonlabeled compound 21 was administered through tail vein injection into the rat after microPET/CT imaging of the spinal cord of SCI rats. One hour later, the rat was perfused with saline followed by 4% paraformaldehyde (PFA) and the spinal cord (T7-L2) was removed, sequentially sectioned, and imaged using a Leica fluorescent microscope.

Figure 13D:
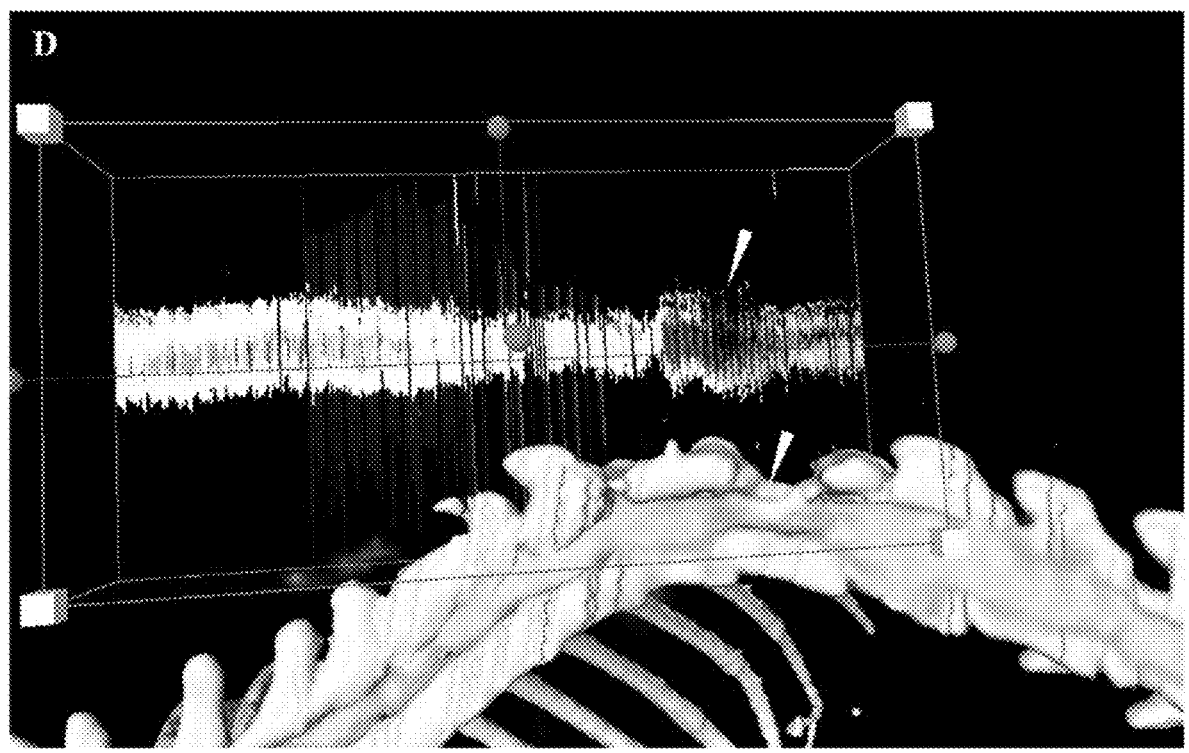
FIGS. 13(A-D) illustrate coregistration of in situ 3D fluorescence imaging with microPET/CT imaging. (A) [$^{18}$F] 21 PET/CT imaging of spinal cord in SCI rat showing reduced uptake after contusive injury at T13 by the arrowhead. (B) 3D in situ fluorescence images of the spinal cord coregistered with CT image of the spinal cord in SCI rat showing reduced fluorescence intensity at T13 by the arrowhead. (C) Fusion images of PET, CT, and 3D fluorescence images. (D) Prior to 3D coregistration, a sagittal slice of the 3D fluorescence image stack indicates demyelination corresponding with microPET/CT imaging.

Slices were aligned sequentially using a semiautomated image registration algorithm through Matlab, giving a 3D reconstructed fluorescence image volume. Image volumes from fluorescence, PET, and CT were visualized in Amira using volume rendering and aligned based on the shape of the spine and fiducials from the vertebrae. As shown in FIG. 13, 3D reconstructed fluorescence images were coregistered with microPET/CT images, where the reduced fluorescence signal was consistent with the reduced microPET signal in the same spinal cord region T13, thereby confirming that the reduced PET signal at the injury site was actually caused by demyelination after the T13 contusion.

Discussion

We developed a novel F-18-labeled radiotracer [$^{18}$F]21 that can be used to quantitatively monitor myelin content in vivo. F-18-labeled radiotracers are often used to facilitate remote distribution of the tracer from a centralized radiopharmacy production site. On the basis of our previously developed C-11 myelin-imaging agent, MeDAS, we designed and synthesized a series of fluorinated analogues for SAR studies in order to identify lead candidates capable of in vivo imaging of myelin. In this work, we designed and synthesized a series of compounds by alkylating one of the terminal amino groups. Our previous studies suggested that the two terminal amino groups of MeDAS are essential moieties for specific binding to myelin. Alkylation of the amino groups does not adversely alter the binding properties, which makes it possible to introduce fluorine to the pharmacophore.

We first examined the lipophilicity of the newly synthesized compounds, which has a significant impact on brain permeability. Because introduction of fluorine to one amino group often renders the compound less lipophilic, we designed a series of fluorinated compounds by introducing an alkyl group into the other amino group to compensate for the decreased lipophilicity. The fluoro group was introduced through a Cu(I)-catalyzed Huisgen cycloaddition, known as the "click reaction", which can be conducted under mild conditions with high yield.

After synthesis of compounds 18-23, we conducted in vitro staining of mouse brain tissue sections. The binding specificity for myelin of each compound was estimated by calculating the FIR between the myelin-rich white matter and myelin-deficient gray matter. As shown in FIG. 7, these compounds had similar fluorescence properties (same excitation and emission wavelength), making it possible for direct comparison of myelin binding specificity based on the FIR when tissue staining was conducted using the same thickness of sections and the same exposure time of image acquisition. Our study suggested that N-linked analogues (21-23) exhibit higher myelin binding specificity than O-linked analogues (18-20). This may be in part due to the fact that introduction of O to the molecules renders the compounds more lipophilic as is evidenced by the higher Log P values shown in Table 1, which increase nonspecific binding.

Among those compounds with higher FIR, compound 21 was selected for further study as it has a log Poct value in the range between 1.5 and 3.5, which is often required for optimal brain uptake. Combination of these studies led us to focus on compound 21 for further in situ staining, which is usually a binding specificity of fluorescent compounds. Our studies indicate that compound 21 readily enters the brain and specifically binds to myelin in white matter regions such as the corpus callosum, striatum, and spinal cord. Furthermore, compound 21 is capable of detecting demyelinated lesions in a rat model of focal demyelination induced by LPC. These studies further confirmed that the characteristic brain uptake and staining of compound 21 is proportional to myelin content in the CNS.

Following in vitro and ex vivo studies, we proceeded with radiosynthesis of [$^{18}$F]21 for in vivo PET imaging studies. The radiosynthesis was achieved by coupling 2-[$^{18}$F] fluoroethyl azide with its alkyne precursor compound 9 in the presence of excess $Cu^{2+}$/ascorbate and bathophenanthrolinedisulfonic acid disodium salt (BPDS) in aqueous solution, yielding the 1,2,3-triazoles product with the desired radiochemical yield (80-90%, n=5, decay corrected) and radiochemical purity of over 98%. 2-[$^{18}$F] fluoroethyl azide is the key intermediate. Although the entire radiosynthesis could be conducted in a "one-pot" fashion, the radiochemical yield was relatively low. Separate isolation and purification of 2-[$^{18}$F] uoroethyl azide was found to be critical for successful radiolabeling. Although [$^{18}$F]-fluoroethyl azide is highly volatile with a boiling point of 50° C., distillation of [$^{18}$F]fluoroethyl azide from the reaction mixture was not practical. We thus used solid phase extraction (SPE) instead with two series of Waters Oasis HLB cartridges to successfully trap [$^{18}$F] uoroethyl azide with high yield and purity.

Following radiosynthesis, we conducted quantitative micro-PET/CT imaging studies in wild-type rats. An ideal radiotracer for in vivo PET imaging of myelin should meet several criteria such as high brain uptake and prolonged retention due to high myelin-binding potential. As expected, quantitative PET data analysis showed a high and rapid accumulation of [$^{18}$F]21 in the brain followed by a rapid nonspecific binding clearance. In situ autoradiography further confirmed that the radioactivity signal detected by PET indeed reflects the specific spatial distribution of [$^{18}$F]21 after binding to myelinated fibers. The combination of in situ autoradiography with [$^{18}$F]21 and with PET imaging studies confirmed that [$^{18}$F]21 is a specific imaging marker of myelin content.

Given the fact that [$^{18}$F]21 binds to myelin sheaths in vivo, we further determined whether [$^{18}$F]21-PET is capable of imaging myelin deficiency or damage as tested in two animal models. The Shiverer mouse model was used to represent a myelin-deficiency in the brain, while the rat model with traumatic SCI was used to represent myelin damage in the spinal cord. As shown in FIG. 11, quantitative analysis of the uptake of [$^{18}$F]21 in the brain showed that retention in the Shiverer mice was significantly lower than that in the WT control (p=0.00028, two-tailed t test). Micro-PET/CT imaging in the SCI rat model further confirmed that [$^{18}$F]21 is capable of detecting and quantifying myelin damage in the spinal cord. As shown in FIG. 12, a distinct myelin-imaging defect at T13 contused tissue could be visualized and quantified directly by PET/CT imaging. Before contusion, [$^{18}$F]21 uptakes at T12, T13, and L1 spine segments were respectively 0.99, 1.02, and 1.05, while the uptakes were 0.99, 0.81, and 1.08 1 day post-T13 contusion. [$^{18}$F]21 uptake decreased dramatically at the site of injury (T13) compared with its own baseline scan.

To date, to expedite the translation of myelin imaging into clinical practice, some radiotracers such as PIB and florbetaben that were originally developed for amyloid imaging have been repurposed for myelin imaging. These radiotracers have already been approved by the FDA for clinical use. Such radiotracers were found to bind to the myelin-rich white matter in the brain, albeit to a lesser extent than amyloid deposits. It is thus believed that they could directly be used in MS patients to image myelin distribution in the white matter region where no amyloid deposits would be present, even in Alzheimer's patients. Thus, the utility of these amyloid-imaging radiotracers were tested in various subtypes of MS patients for correlation of tracer uptake with MRI characterization of brain lesions, disease progression patterns, and functional disability. These studies provided proof-of-the-concept that PET imaging is a valid clinical imaging tool to observe white matter changes in terms of myelin distribution. However, these radiotracers originally were so optimized for amyloid imaging that any binding potential in the white matter was minimized. This makes it difficult to address several important issues concerning imaging sensitivity and specificity under an in inflammatory condition that is typical of MS. Independent studies often led to controversial interpretations of imaging results.

To overcome these limitations and enhance the myelin-imaging sensitivity and specificity, new myelin-imaging radio-tracers must be developed whereby the binding potential for myelin can be maximized in the white matter. The parent compound, MeDAS, was thus optimized to be specific for myelin and to minimize any effect of in inflammation. On the basis of solid preclinical validation, it will significantly improve the imaging sensitivity and specificity.

An important innovative aspect of this work lies in the combination of PET/CT with 3D cryoimaging. PET is a tomographic, functional imaging modality with high quantitative capacity. Yet, PET quantitative analysis must be validated by correlation with histological characterization. This is often a very challenging task, particularly in spinal cord imaging due to its small and mobile structure. Tissue preparation and sectioning are very time-consuming, and only selected tissue sections can be used for validation of PET-imaging results, which is likely biased by the limited scope of sampling. Tomographic cryoimaging thus can overcome this limitation as it can provide high-resolution, three-dimensional images of the entire spinal cord for histological characterization. The whole process can be fully automated using a CryoViz system (BioInVision, Inc.). The imaging results are thus less subjective as the sampling bias can be essentially eliminated. More importantly, the 3D cryoimaging of the spinal cord was carried out in situ using nonlabeled, otherwise identical compound 21, which was administered via tail vein injection in a way similar to the PET scan. This promotes accurate image coregistration between PET and cryoimaging for quantitative analysis.

This new multimodality PET/cryoimaging technique was first applied in the studies of SCI. In vivo imaging of myelin changes after SCI is of particular importance as demyelination and remyelination have direct effects on disability and functional recovery. To confirm that the contusive injury at T13 was associated directly with demyelination rather than tissue loss, we conducted in situ 3D cryoimaging with fluorescent compound 21 following microPET/CT imaging using [$^{18}$F]21. As shown in FIG. 12A, a distinct demyelination at the dorsal portion was observed. This was further confirmed by standard LFB and cresyl violet staining of myelin sheaths on the adjacent sections, which suggests there was a significant demyelinated lesion in the white matter region at the injury site. In contrast, no tissue loss was observed and myelinated white matter outside the injured region remained intact (FIG. 13B). After tomographic 3D reconstruction, the cryoimages were coregistered with PET/CT images (FIG. 13). We observed significant reduction of the fluorescence signal in the lesion region of the spinal cord, validating the sensitivity and specificity of PET. These findings suggest that [$^{18}$F]21-PET imaging can be used as a diagnostic marker of myelin damage. In addition, we demonstrated, for the first time, the feasibility of simultaneous coregistration of PET/CT with and validation by high-resolution, 3D cryoimaging, which allows for seamless combination of physiological information with the high sensitivity and quantification capability provided by PET and microscopic histology provided by cryoimaging. This newly developed multimodality imaging technique should greatly facilitate radiotracer development and efficacy evaluation of novel therapies.

In summary, a series of fluorinated fluorescent myelin-binding agents was synthesized for PET and 3D cryoimaging. Following systematic SAR studies, we identified a novel myelin-imaging agent (TAFDAS, 21) that readily penetrates the BBB and binds to myelin membranes in the brain and spinal cord. Sequential [$^{18}$F]21-PET imaging and 3D cryoimaging in contusion rat model of SCI demonstrate, for the first time, that combination of PET and cryoimaging is a new imaging tool with high sensitivity, specificity, and spatial resolution.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of detecting myelin in vivo in a subject's central nervous system tissue, the method comprising:
   (i) administering to the subject a radioligand including a compound having the formula:

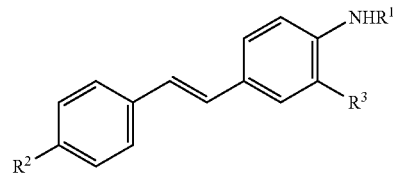

wherein $R^1$ is a radiolabeled triazole group;
$R^2$ is NHR', where R' is a lower alkyl group;
$R^3$ is H;
wherein $R^1$, includes a radiolabel selected from the group consisting of $^{18}$F, $^{123}$I, $^{125}$I, and $^{99m}$Tc; or a pharmaceutically acceptable salt thereof; and
   (ii) detecting the location, distribution, and/or amount of the radioligand that is bound to and/or labels myelin to detect myelin in vivo in the central nervous system tissue.

2. The method of claim 1, wherein the radioligand has the formula:

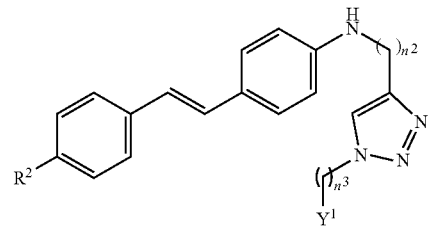

wherein $R^2$ is NHR', where R' a lower alkyl group;
$n^2$ is 1 to 6;
$n^3$ is 1 to 6;
$Y^1$ is a radiolabel selected from the group consisting of $^{18}$F, $^{123}$I, $^{125}$I, and $^{99m}$Tc; or a pharmaceutically acceptable salt thereof.

3. The method of claim 1, wherein the radioligand has the formula:

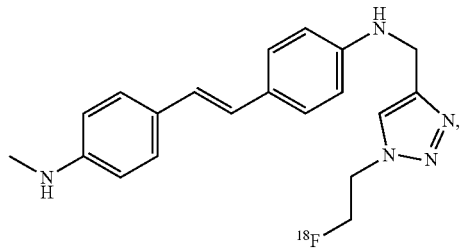 [SMILES: CNc1ccc(/C=C/c2ccc(NCc3cn(CC[18F])nn3)cc2)cc1]

or pharmaceutically acceptable salts thereof.

4. The method of claim 1, the radioligand is detected in vivo by in Positron Emission Tomography (PET) imaging or micro Positron Emission Tomography (microPET) imaging.

5. The method of claim 1, further comprising the step of administering the radioligand to the subject parenterally.

6. The method of claim 1, wherein the radioligand further comprises a chelating group or a near infrared imaging group.

7. A method of detecting a myelin related disorder of the central nervous system in a subject in need thereof, the method comprising the steps of:
(i) administering to the subject a radioligand that includes a compound having the formula:

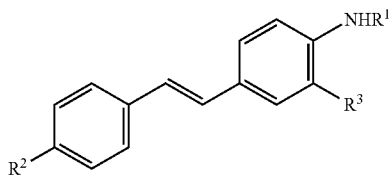

wherein $R^1$ is a radiolabeled triazole group;
$R^2$ is NHR', where R' is a lower alkyl group;
$R^3$ is H;
wherein $R^1$ includes a radiolabel selected from the group consisting of $^{18}F$, $^{123}I$, $^{125}I$, and $^{99m}Tc$; or a pharmaceutically acceptable salt thereof;
(ii) detecting the distribution and/or amount of the radioligand in vivo that is bound to and/or labels myelin in a region of interest in central nervous system tissue of the subject; and
(iii) comparing the detected distribution and/or amount of the radioligand that is bound to and/or labels myelin to a control, wherein a decreased distribution and/or amount of the radioligand that is bound to and/or labels myelin compared to the control is indicative of a decrease in myelination of the tissue and the presence of myelination related disorder of the central nervous system.

8. The method of claim 7, wherein the radioligand has the formula:

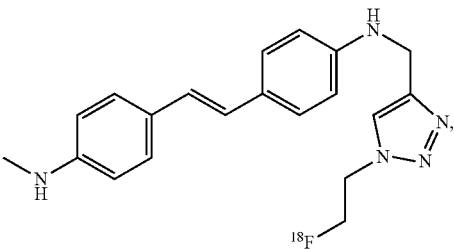 [SMILES: CNc1ccc(/C=C/c2ccc(NCc3cn(CC[18F])nn3)cc2)cc1]

or pharmaceutically acceptable salts thereof.

9. The method of claim 7, wherein the radioligand is detected in vivo using Positron Emission Tomography (PET) or micro Positron Emission Tomography (microPET) imaging modality.

10. The method of claim 7, further comprising the step of administering the radioligand to the subject parenterally.

11. The method of claim 7, wherein the radioligand further comprises a chelating group or a near infrared imaging group.

12. The method of claim 7, wherein the myelin related disorder in the central nervous system is a neurodegenerative autoimmune disease.

13. The method of claim 12, wherein the neurodegenerative autoimmune disease is multiple sclerosis.

14. The method of claim 1, wherein the radioligand has a lipophilicity value of less than about 4.0.

15. The method of claim 7, wherein the radioligand has a lipophilicity value of less than about 4.0.

16. The method of claim 1, wherein the subject has an intact blood brain barrier.

17. The method of claim 7, wherein the subject has an intact blood brain barrier.

* * * * *